United States Patent [19]

Webber et al.

[11] Patent Number: 5,962,487
[45] Date of Patent: Oct. 5, 1999

[54] ANTIPICORNAVIRAL COMPOUNDS AND METHODS FOR THEIR USE AND PREPARATION

[75] Inventors: Stephen E. Webber, San Diego; Peter S. Dragovich, Encinitas; Thomas J. Prins, Cardiff; Ethel S. Littlefield, San Diego; Joseph T. Marakovits, Encinitas; Robert E. Babine, Carlsbad, all of Calif.

[73] Assignee: Agouron Pharmaceuticals, Inc., La Jolla, Calif.

[21] Appl. No.: 08/991,739

[22] Filed: Dec. 16, 1997

[51] Int. Cl.$^6$ ............... A01N 43/80; A01N 43/50; A01N 43/38; A01N 43/08

[52] U.S. Cl. ............... 514/378; 514/385; 514/415; 514/471; 514/513; 514/542; 560/9; 560/16; 560/17; 560/27; 560/32; 544/63; 544/388; 544/383; 544/319; 544/382; 548/201; 548/230; 548/248; 548/331.1

[58] Field of Search ............... 544/63, 388, 383, 544/319, 282; 546/194, 144, 331; 548/201, 230, 248, 331.1, 340.1, 349.1, 469, 538, 540, 550; 549/77, 321; 560/9, 16, 17, 24, 27, 32; 562/623; 514/378, 385, 415, 471, 513, 542

[56] References Cited

FOREIGN PATENT DOCUMENTS

| | | |
|---|---|---|
| 632051 | 1/1995 | European Pat. Off. . |
| WO92/22570 | 12/1992 | WIPO . |
| WO95/23222 | 8/1995 | WIPO . |
| WO95/31433 | 11/1995 | WIPO . |

OTHER PUBLICATIONS

Hanzlik et al., "Vinylogous Amino Acid Esters: A New Class of Inactivators for Thiol Proteases," *J. Med. Chem.*, vol. 27, No. 6 Jun. 1984, pp. 711–712.

Thompson et al., "Carboxyl–Modified Amino Acids and Peptides as Protease Inhibitors," *J. Med. Chem.*, vol. 29, No. 1, 1986, pp. 104–111.

Liu et al., "Structure–Activity Relationships for Inhibition of Papain by Peptide Michael Acceptors," *J. Med. Chem.*, vol. 35, 1992, pp. 1067–1075.

White et al., *Principles of Biochemistry*, 6th Ed., McGraw Hill, 1978, pp. 893–895.

Callahan et al., "Molecular cloning and complete sequence determination of RNA genome of human rhinovirus type 14," *Proc. Natl. Acad. Sci. USA*, vol. 82, Feb. 1985, pp. 732–736.

Olson et al., "Structure of a human rhinovirus complexed with its receptor molecule," *Proc. Natl. Acad. Sci. USA*, vol. 90, Jan. 1993, pp. 507–511.

Hammerle et al., "Site–directed Mutagenesis of the Putative Catalytic Traid of Poliovirus 3C Proteinase," *J. Biol. Chem.*, vol. 266, No. 9, 1991, pp. 5412–5416.

Orr et al., "Hydrolysis of a Series of Synthetic Peptide Substrates by the Human Rhinovirus 14 3C Proteinase, Cloned and Expressed in *Escherichia coli*," *J. Gen. Virol*, vol. 70, 1989, pp. 2931–2942.

Leong et al., "Human Rhinovirus–14 Protease 3C (3C$^{pro}$) Binds Specifically to the 5'–Noncoding Region of the Viral RNA," *J. Biol. Chem.*, vol. 268, 1993, pp. 25735–25739.

*Comprehensive Medicinal Chem.*, vol. 2, C. Hansch, Eds., Pergamon Press, Oxford, 1990, pp. 431–433, 440–441.

Shaw, "Cysteinyl Proteinases and Their Selective Inactivation," *Advance Enz*, vol. 63, 1990, pp. 271–347.

Matthews et al., "Structure of Human Rhinovirus 3C Protease Reveals a Trypsin–like Polypeptide Fold, RNA–Binding Site, and Means for Cleaving Precursor Polyprotein," *Cell*, vol. 77, Jun. 1994, pp. 761–771.

Allaire et al., "Picornaviral 3C cysteine proteinases have a fold similar to chymotrypsin–like serine proteinases," *Nature*, vol. 369, May 1994, pp. 72–76.

Bazan et al., "Viral cysteine proteases are homologous to the trypsin–like family of serine proteases: Structural and functional implications," *Proc. Natl. Acad. Sci. USA*, vol. 85, Nov. 1988, pp. 7872–7876.

Cordingley et al., "Cleavage of Small Peptides In Vitro by Human Rhinovirus 14 3C Protease Expressed in *Escherichia coli*," *Journal of Virology*, vol. 63, No. 12, Dec. 1989, pp. 5037–5045.

Kaldor et al., "Glutamine–Derived Aldehydes for the Inhibition of Human Rhinovirus 3C Protease," *Bioorganic& Medicinal Chemistry Letters*, vol. 5, No. 17, 1995, pp. 2021–2026.

Malcolm et al., "Peptide Aldehyde Inhibitors of Hepatitis A Virus 3C Proteinase," *Biochemistry*, vol. 34, 1995, pp. 8172–8179.

Skiles et al., "Spiro Indolinone Beta–Lactams, Inhibitors of Poliovirus and Rhinovirus 3C–Proteinases," *Tetrahedron Letters*, vol. 31, No. 50, 1990, pp. 7277–7280.

Singh et al., "Structure and Stereochemistry of Thysanone: A Novel Human Rhinovirus 3C–Protease Inhibitor from *Thysanophora penicilloides*," *Tetrahedron Letters*, vol. 32, No. 39, 1991, pp. 5279–5282.

Kadam et al., "Citrinin Hydrate and Radicinin: Human Rhinovirus 3C–Protease Inhibitors Discovered in a Target–Directed Microbial Screen," *The Journal of Antibiotics*, vol. 47, No. 7, Jul. 1994, pp. 836–839.

(List continued on next page.)

*Primary Examiner*—Porfirio Nazario-Gonzalez
*Assistant Examiner*—Brian J. Davis
*Attorney, Agent, or Firm*—Finnegan, Henderson, Farabow, Garrett & Dunner, L.L.P.

[57] ABSTRACT

Picornaviral 3C protease inhibitors, obtainable by chemical synthesis, inhibit or block the biological activity of picornaviral 3C proteases. These compounds, as well as pharmaceutical compositions that contain these compounds, are suitable for treating patients or hosts infected with one or more picornaviruses. Several novel methods and intermediates can be used to prepare the novel picornaviral 3C protease inhibitors of the present invention.

34 Claims, No Drawings

OTHER PUBLICATIONS

Palmer et al., "Vinyl Sulfones as Mechanism–Based Cysteine Protease Inhibitors," *J. Med. Chem.*, vol. 38, 1995, pp. 3913–3196.

Maryanoff et al., "Molecular basis for the inhibition of human α–thrombin by the macrocylic peptide cyclotheonamide A," *Proc. Natl. Acad. Sci. USA*. vol. 90, Sep. 1993, pp. 8048–8052.

Rich et al., "Synthesis of Analogues of the Carboxyl Protease Inhibitor Pepstatin. Effect of Structure on Inhibition of Pepsin and Renin," *J. Med. Chem.*, vol. 23, 1980, pp. 27–33.

Hagihara et al., "Reassignment of Stereochemistry and Total Synthesis of the Thrombin Inhibitor Cyclotheonamide B," *J. Am. Chem. Soc.*, vol. 114, 1992, pp. 6570–6571.

Haberson et al., "Inhibition of Aminopeptidases by Peptides Containing Ketomethylene and Hydroxyethylene Amide Bond Replacements," *J. Med. Chem.*, vol. 32, 1989, pp. 1378–1392.

Barton et al., "Synthesis of Novel α–Amino–Acids and Derivatives using Radical Chemistry: Synthesis of L–and D–α–Amino–Adipic Acids, L–α–Aminopimelic Acid and Appropriate Unsaturated Derivatives," *Tetrahedron*, vol. 43, No. 19, 1987, pp. 4297–4308.

Smith et al., "Synthesis and Renin Inhibitory Activity of Angiotensinogen Analogues Having Dehydrostatine, LeuΨ[$CH_2S$]Val, or LeuΨ[$CH_2SO$]Val at the $P_1$–$P_1'$ Cleavage Site," *J. Med. Chem.*, vol. 31, 1988, pp. 1377–1382.

Meng et al., "Synthetic Approaches toward Glidobamine, the Core Structure of the Glidobactin Antibiotics," *Tetrahedron*, vol. 47, No. 32, 1991, pp. 6251–6264.

Kolter et al., "Configuratively Stable Dipeptide Aldehydes from D–Glucosamine Hydrochloride," *Angew. Chem. Int. Ed. Engl.*, vol. 31, No. 10, 1992, pp. 1391–1392.

Reetz et al., "Stereoselective Nucleophilic Addition Reactions of Reactive Pseudopeptides," *Angew. Chem. Int. Ed. Engl.*, vol. 31, No. 12, 1992, pp. 1626–1629.

Aoyagi et al., "Structures and Activities of Protease Inhibitors of Microbial Origin," Institute of Microbial Chemistry, Tokyo, Japan, 1975, pp. 429–454.

Rich, "Inhibitors of cysteine proteinases," *Proteinase Inhibitors*, Barrett and Salvesen (eds.), Elsvier Science Publishers BV, 1986, pp. 154–178.

Herold et al., "A Versatile and Stereocontrolled Synthesis of Hydroxyethylene Dipeptide Isosteres," *J. Org. Chem.*, vol. 54 (1989), pp. 1178–1185.

Bradbury et al., "An Efficient Synthesis of the γ–Lactone Corresponding to a Hydroxyethylene Dipeptide Isostere Using Stereoselective Bromolactonisation of a Chiral Acyloxazolidinone," *Tetrahedron Letters*, vol. 30, No. 29 (1989), pp. 3845–3848.

Bradbury et al., "1,2,4–Triazolo[4,3–a]pyrazine Derivatives with Human Renin Inhibitory Activity," *J. Med. Chem.*, vol. 33 (1990), pp. 2335–2342.

Wuts et al., "Synthesis of the Hydroxyethylene Isostere of Leu–Val," *J. Org. Chem.*, vol. 57 (1992), pp. 6696–6700.

Jones et al., "A Short Stereocontrolled Synthesis of Hydroxyethylene Dipeptide Isosteres," *J. Org. Chem.*, vol. 58 (1993), pp. 2286–2290.

Pégorier et al., "A General Stereocontrolled Synthesis Hydroxyethylene Dipeptide Isosteres," *Tetrahedron Letters*, vol. 36, No. 16 (1995), pp. 2753–2756.

Dondoni et al., "Thiazole–Based Stereoselective Routes to Leucine and Phenylalanine Hydroxyethylene Dipeptide Isostere Inhibitors of Renin and HIV–1 Aspartic Protease," *J. Org. Chem.*, vol. 60 (1995), pp. 7927–7933.

Weislow et al., "New Soluble–Formazan Assay for HIV–1 Cytopathic Effects: Application to High–Flux Screening of Synthetic and Natural Products for AIDS–Antiviral Activity," *Journal of the National Cancer Institute*, vol. 81, No. 8 (1989), pp. 577–586.

L.A. Carpino, "1–Hydroxy–7–Azabenzotriazole. An Efficient Peptide Coupling Additive," *Journal of the American Chemical Society*, vol. 115, No. 10 (1993), pp. 4397–4398.

J.E. Baldwin, et al., "An Intramolecular Cobalt Cyclisation for the Construction of Substituted Pyrrolidines," *Tetrahedron*, vol. 48, No. 42 (1992), pp. 9373–9384.

J.J. Willard, et al., "New Method of Removing Xanthate Groups from Carbohydrates. Chemical Structure of Methyl α–D–Glucopyranoside Monoxanthate," *Journal of the American Chemical Society*, vol. 82, No. 16 (1960), pp. 4347–4350.

R.M. Freidlinger, et al., "Synthesis of 9–Fluorenylmethyloxycarbonyl–Protected N–Alkyl Amino Acids by Reduction of Oxazolidinones," *Journal of Organic Chemistry*, vol. 48, No. 4 (1983), pp. 77–81.

D.A. Niederer, et al., "Amination with N–Benzyloxycarbonyl–3–Phenyloxasiridine as a Route to Sensitive Chiral α–Hydrazino Acids: Synthesis of L–Hydrazino Serine," *Tetrahedron Letters*, vol. 34, No. 43 (1993), pp. 6859–6862.

C.A. Veale, et al., "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones," *Journal of Medicinal Chemistry*, vol. 38, No. 1 (1995), pp. 98–108.

R.V. Hoffman, et al., "A Simple, Stereoselective Synthesis of Ketomethylene Dipeptide Isosteres," *Tetrahedron*, vol. 53, No. 21 (1997), pp. 7119–7126.

D. Askin, et al., "Highly Diastereoselective Alkylations of Chiral Amide Enolates: New Routes to Hydroxyethylene Dipeptide Isostere Inhibitors of HIV–1 Protease," *Journal of Organic Chemistry*, vol. 57, No. 10 (1992), pp. 2771–2773.

J.C. McWilliams, et al., "Tandem Asymmetric Transformations: An Asymmetric 1,2–Migration from a Higher Order Zincate Coupled with a Stereoselective Homoaldol Reaction," *Journal of the American Chemical Society*, vol. 118, No. 47 (1996), pp. 11970–11971.

J.R. Luly, et al., "A Synthesis of Protected Aminoalkyl Epoxides from α–Amino Acids," *Journal of Organic Chemistry*, vol. 52, No. 8 (1987), pp. 1487–1492.

March, *Advanced Organic Chemistry*, Fourth Edition, John Wiley & Sons, Inc. (New York), 1992, pp. 205,351–356, 642–643, 647, 652–653, 666, 501, 520–521, 569, 579–580, 992–994, 999–1000, 1005, and 1008.

H. Ikuta, et al., "Synthesis and Antiinflammatory Activities of 3–(3,5–Di–tert–butyl–4–hydroxybenzylidene)pyrrolidin–2–ones," *Journal of Medicinal Chemistry*, vol. 30, No. 11 (1987), pp. 1995–1998.

Shcherbina, et al., *Chemical Abstract* No. 68:69376 (1968).

Venkatramam, et al., "Synthesis of Potential Inhibitors for Human Rhinovirus 3 C Protease," *The Second Winter Conference on Medicinal and Bioorganic Chemistry*, Steamboat Springs, Colorado, Jan. 26–31, 1997.

Hellen, et al., "Proteolytic Processing of Polyproteins in the Replication of RNA Viruses," *Biochemistry*, vol. 28, No. 26 (1989), pp. 9881–9890.

Matthews, et al., "Structure of Human Rhinovirus 3C Protease Reveals a Trypsin–like Polypeptide Fold, RNA–Binding Site, and Means for Cleaving Precursor Polyprotein," *Cell*, vol. 77, No. 5 (1994), pp. 761–771.

Cordingley, et al., Substrate Requirements of Human Rhinovirus 3C Protease for Peptide Cleavage in Vitro, *The Journal of Biological Chemistry*, vol. 265, No. 16 (1990), pp. 9062–9065.

Wellink, et al., "Proteases Involved in the Processing of Viral Polyproteins," *Archives of Virology*, vol. 98 (1988), pp. 1–26.-

ANTIPICORNAVIRAL COMPOUNDS AND METHODS FOR THEIR USE AND PREPARATION

RELATED APPLICATION DATA

This application relates to U.S. patent application Ser. Nos. 08/825,331, filed Mar. 28, 1997, and 08/850,398, filed May 2, 1997. Additionally, this application relates to U.S. Provisional Patent Application Ser. No. 60/046,204, filed May 12, 1997. Each of these U.S. patent applications relates to antipicornaviral compounds, compositions containing them, and methods for their production and use. Each of these applications also is entirely incorporated herein by reference. Additionally, this application relates to a concurrently filed U.S. patent application entitled "Antipicornaviral Compounds, Compositions Containing Them, and Methods for Their Use," U.S. patent application Ser. No. 08/991,282, filed in the names of inventors Peter S. Dragovich, Thomas J. Prins, and Ru Zhou (Attorney Docket No. 1074.0176-01). This concurrently filed application also is entirely incorporated herein by reference.

BACKGROUND OF THE INVENTION

The invention pertains to the discovery and use of new compounds that inhibit the enzymatic activity of picornaviral 3C proteases, specifically rhinovirus proteases ("RVPs"), as well as retard viral growth in cell culture.

The picornaviruses are a family of tiny non-enveloped positive stranded RNA containing viruses that infect humans and other animals. These viruses include the human rhinoviruses, human polioviruses, human coxsackieviruses, human echoviruses, human and bovine enteroviruses, encephalomyocarditis viruses, menigovirus, foot and mouth viruses, hepatitis A virus, and others. The human rhinoviruses are a major cause of the common cold. To date, there are no effective therapies to cure the common cold, only treatments that relieve the symptoms.

Picornaviral infections may be treated by inhibiting the proteolytic 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the polyprotein, which in turn can retard the maturation and replication of the viruses by interfering with viral particle production. Therefore, inhibiting the processing of this cysteine protease with selective, small molecules that are specifically recognized, should represent an important and useful approach to treat or cure viral infections of this nature and, in particular, the common cold.

SUMMARY OF THE INVENTION

The present invention is directed to compounds that function as picornaviral 3C protease inhibitors, particularly those that have antiviral activity. It is further directed to the preparation and use of such 3C protease inhibitors. The Inventors demonstrate that the compounds of the present invention bind to rhinovirus 3C proteases and preferably have antiviral cell culture activity. The enzymatic inhibition assays used reveal that these compounds can bind irreversibly, and the cell culture assays demonstrate that these compounds can possess antiviral activity.

The present invention is directed to compounds of the formula (I):

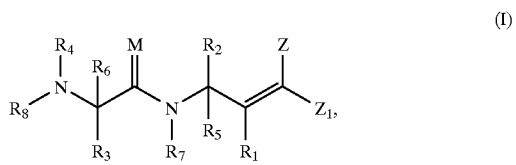

wherein:

M is O or S;

$R_1$ is H, F, an alkyl group, OH, SH, or an O—alkyl group;

$R_2$ and $R_5$ are independently selected from H,

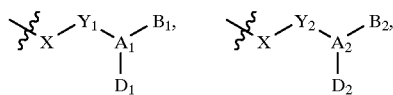

or an alkyl group, wherein the alkyl group is different from

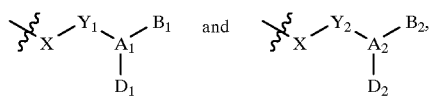

with the proviso that at least one of $R_2$ or $R_5$ must be

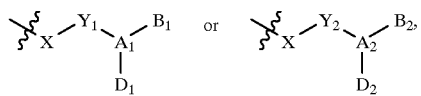

and wherein, when $R_2$ or $R_5$ is

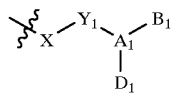

X is =CH or =CF and $Y_1$ is =CH or =CF, or X and $Y_1$ together with Q' form a three-membered ring in which Q' is —C($R_{10}$)($R_{11}$)— or —O—, X is —CH— or —CF—, and $Y_1$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —CH$_2$—, —CF$_2$—, —CHF—, or —S—, and $Y_1$ is —O—, —S—, —NR$_{12}$—, —C($R_{13}$)($R_{14}$)—, —C(O)—, —C(S)—, or —C(C$R_{13}R_{14}$)—, wherein $R_{12}$ is H or alkyl, and $R_{13}$ and $R_{14}$ independently are H, F, or an alkyl group, or, together with the atoms to which they are bonded, form a cycloalkyl group or a heterocycloalkyl group;

$A_1$ is C, CH, CF, S, P, Se, N, NR$_{15}$, S(O), Se(O), P—OR$_{15}$, or P—NR$_{15}R_{16}$, wherein $R_{15}$ and $R_{16}$ independently are an alkyl group, a cycloalkyl group, a heterocycloalkyl group, an aryl group, or a heteroaryl group, or, together with the atom to which they are bonded, form a heterocycloalkyl group;

$D_1$ is a moiety with a lone pair of electrons capable of forming a hydrogen bond; and $B_1$ is H, F, an alkyl group, a cycloalkyl group, a heterocycloalkyl group, an aryl group, a heteroaryl group, $—OR_{17}$, $—SR_{17}$, $—NR_{17}R_{18}$, $—NR_{19}NR_{17}R_{18}$, or $—NR_{17}OR_{18}$,
wherein $R_{17}$, $R_{18}$, and $R_{19}$ independently are H, an alkyl group, a cycloalkyl group, a heterocycloalkyl group, an aryl group, a heteroaryl group, or an acyl group;

and with the provisos that when $D_1$ is the moiety $\equiv$N with a lone pair of electrons capable of forming a hydrogen bond, $B_1$ does not exist; and when $A_1$ is an sp$^3$ carbon, $B_1$ is not $—NR_{17}R_{18}$ when $D_1$ is the moiety $—NR_{25}R_{26}$ with a lone pair of electrons capable of forming a hydrogen bond, wherein $R_{25}$ and $R_{26}$ are independently H, an alkyl group, a cycloalkyl group, a heterocycloalkyl group, an aryl group, or a heteroaryl group;

and wherein $D_1$—$A_1$—$B_1$ optionally forms a nitro group where $A_1$ is N;

and further wherein, when $R_2$ or $R_5$ is

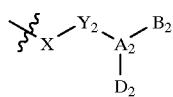

X is =CH or =CF and $Y_2$ is =C, =CH or =CF,
or X and $Y_2$ together with Q' form a three-membered ring in which Q' is —C($R_{10}$)($R_{11}$)— or —O—, X is —CH— or —CF—, and $Y_2$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group,
or X is —CH$_2$—, —CF$_2$—, —CHF—, or —S—, and $Y_2$ is —O—, —S—, —N(R'$_{12}$)—, —C(R'$_{13}$)(R'$_{14}$)—, —C(O)—, —C(S)—, or —C(CR'$_{13}$R'$_{14}$)—,
wherein R'$_{12}$ is H, an alkyl group, a cycloalkyl group, a heterocycloalkyl group, an aryl group, a heteroaryl group, —OR'$_{13}$, —NR'$_{13}$R'$_{14}$, —C(O)—R'$_{13}$, —SO$_2$R'$_{13}$, or —C(S)R'$_{13}$, and R'$_{13}$ and R'$_{14}$ independently are H, F, an alkyl group, a cycloalkyl group, a heterocycloalkyl group, an aryl group, or a heteroaryl group or, together with the atom to which they are attached, form a cycloalkyl group or a heterocycloalkyl group;

$A_2$ is C, CH, CF, S, P, Se, N, NR$_{15}$, S(O), Se(O), P—OR$_{15}$, or P—NR$_{15}$R$_{16}$,
wherein $R_{15}$ and $R_{16}$ independently are an alkyl group, a cycloalkyl group, a heterocycloalkyl group, an aryl group, or a heteroaryl group or, together with the atom to which they are bonded, form a heterocycloalkyl group;

$D_2$ is a moiety with a lone pair of electrons capable of forming a hydrogen bond; and $B_2$ is H, F, an alkyl group, a cycloalkyl group, a heterocycloalkyl group, an aryl group, a heteroaryl group, $—OR_{17}$, $—SR_{17}$, $—NR_{17}R_{18}$, $—NR_{19}NR_{17}R_{18}$, or $—NR_{17}OR_{18}$,
wherein $R_{17}$, $R_{18}$, and $R_{19}$ independently are H, an alkyl group, a cycloalkyl group, a heterocycloalkyl group, an aryl group, a heteroaryl group, or an acyl group;

and further wherein any combination of $Y_2$, $A_2$, $B_2$, and $D_2$ forms a cycloalkyl group, a heterocycloalkyl group, an aryl group, or a heteroaryl group;

$R_3$ and $R_6$ are independently H, F, an alkyl group, a cycloalkyl group, a heterocycloalkyl group, an aryl group, a heteroaryl group, —C(O)R$_{17}$, —OR$_{17}$, —SR$_{17}$, —NR$_{17}$R$_{18}$, —NR$_{19}$NR$_{17}$R$_{18}$, or —NR$_{17}$OR$_{18}$,
wherein $R_{17}$, $R_{18}$, and $R_{19}$ independently are H, an alkyl group, a cycloalkyl group, a heterocycloalkyl group, an aryl group, a heteroaryl group, or an acyl group;

or, $R_3$ and $R_6$, together with the carbon atom to which they are attached, form a cycloalkyl group or a heterocycloalkyl group;

$R_4$ is any suitable organic moiety, or $R_4$ and $R_3$ or $R_6$, together with the atoms to which they are attached, form a heterocycloalkyl group;

$R_7$ is H, an alkyl group, a cycloalkyl group, a heterocycloalkyl group, an aryl group, a heteroaryl group, —OR$_{17}$, —SR$_{17}$, —NR$_{17}$R$_{18}$, —NR$_{19}$NR$_{17}$R$_{18}$, or —NR$_{17}$OR$_{18}$,
wherein $R_{17}$, $R_{18}$, and $R_{19}$ independently are H, an alkyl group, a cycloalkyl group, a heterocycloalkyl group, an aryl group, a heteroaryl group, or an acyl group;

or $R_7$ together with $R_3$ or $R_6$ and the atoms to which they are attached form a heterocycloalkyl group; $R_8$ is H, an alkyl group, a cycloalkyl group, a heterocycloalkyl group, an aryl group, a heteroaryl group, —NR$_{29}$R$_{30}$, —OR$_{29}$, or —C(O)R$_{29}$,
wherein $R_{29}$ and $R_{30}$ each independently are H, an alkyl group, a cycloalkyl group, a heterocycloalkyl group, an aryl group, or a heteroaryl group;

or $R_8$ together with $R_4$ and the nitrogen atom to which they are attached form a heterocycloalkyl group or a heteroaryl group, or $R_8$ and $R_3$ or $R_6$, together with the atoms to which they are attached, form a heterocycloalkyl group;

Z and $Z_1$ are independently H, F, an alkyl group, a cycloalkyl group, a heterocycloalkyl group, an aryl group, a heteroaryl group, —C(O)R$_{21}$, —CO$_2$R$_{21}$, —CN, —C(O)NR$_{21}$, R$_{22}$, —C(O)NR$_{21}$OR$_{22}$, —C(S)R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)(R$_{22}$), —PO(NR$_{21}$R$_{22}$)(OR$_{23}$), —PO(NR$_{21}$R$_{22}$)(NR$_{23}$R$_{24}$), —C(O)NR$_{21}$NR$_{22}$R$_{23}$, or —C(S)NR$_{21}$ NR$_{22}$R$_{23}$,
wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group;

or $Z_1$, as defined above, together with $R_1$, as defined above, and the atoms to which $Z_1$ and $R_1$ are bonded, form a cycloalkyl or heterocycloalkyl group, or Z and $Z_1$, both as defined above, together with the atoms to which they are bonded, form a cycloalkyl or heterocycloalkyl group;

with the proviso that when $R_7$ is H, $R_8$ is a moiety other than H;

and pharmaceutically acceptable prodrugs, salts, active metabolites, and solvates thereof;

and wherein these compounds, pharmaceutically acceptable prodrugs, salts, active metabolites, and solvates preferably have antipicornaviral activity with an EC$_{50}$ less than or equal to 100 μM in the HI-HeLa cell culture assay, and more preferably antirhinoviral activity with an $EC_{50}$ less than or equal to 100 μM in the HI-HeLa cell culture assay and/or anticoxsachieviral activity with an $EC_{50}$ less than or equal to 100 μM in the HI-HeLa cell culture assay.

DETAILED DESCRIPTION OF THE INVENTION

The present invention relates to compounds of the formula I

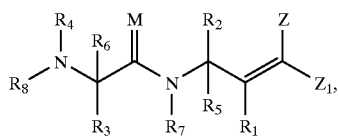
(I)

wherein $R_1$, $R_2$, $R_3$, $R_4$, $R_5$, $R_6$, $R_7$, $R_8$, M, Z, and $Z_1$ are as defined above, and to the pharmaceutically acceptable prodrugs, salts, active metabolites, and solvates thereof, where these compounds, pharmaceutically acceptable prodrugs, salts, active metabolites, and solvates preferably have antipicornaviral activity with an $EC_{50}$ less than or equal to 100 μM in the HI-HeLa cell culture assay, and more preferably antirhinoviral activity with an $EC_{50}$ less than or equal to 100 μM in the HI-HeLa cell culture assay and/or anticoxsachieviral activity with an $EC_{50}$ less than or equal to 100 μM in the HI-HeLa cell culture assay.

The present invention preferably relates to compounds of the formula II:

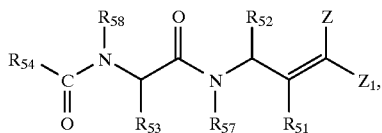
(II)

wherein:

$R_{51}$, is H, F, or an alkyl group;

$R_{52}$ is selected from one of the following moieties:

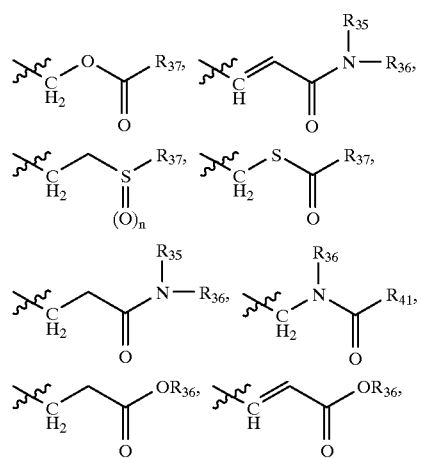

-continued
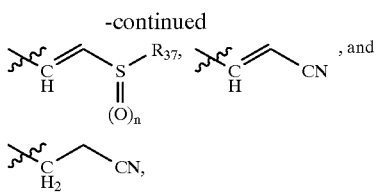
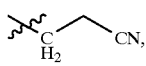
, and wherein:

$R_{35}$ is H, an alkyl group, an aryl group, —$OR_{38}$, or —$NR_{38}R_{39}$,
  wherein $R_{38}$ and $R_{39}$ independently are H, an alkyl group, a cycloalkyl group, a heterocycloalkyl group, an aryl group, a heteroaryl group, or an acyl group; and $R_{36}$ is H or an alkyl group, or $R_{35}$ and $R_{36}$, together with the nitrogen atom to which they are attached, form a heterocycloalkyl group or a heteroaryl group;

$R_{37}$ is an alkyl group, an aryl group, or —$NR_{38}R_{39}$, wherein $R_{38}$ and $R_{39}$ are as defined above;

$R_{41}$ is H, an alkyl group, an aryl group, —$OR_{38}$, —$SR_{39}$, —$NR_{38}R_{39}$, —$NR_{40}NR_{38}R_{39}$, or —$NR_{38}OR_{39}$, or $R_{41}$ and $R_{36}$, together with the atom(s) to which they are attached, form a heterocycloalkyl group;
  wherein $R_{38}$ and $R_{39}$ are as defined above, and $R_{40}$ is H, an alkyl group, a cycloalkyl group, a heterocycloalkyl group, an aryl group, a heteroaryl group, or an acyl group; and n is 0, 1 or 2;

$R_{53}$ is H or an alkyl group;

$R_{54}$ is an alkyl group, a cycloalkyl group, a heterocycloalkyl group, an aryl group, a heteroaryl group, an O—alkyl group, an O—cycloalkyl group, an O—heterocycloalkyl group, an O—aryl group, an O—heteroaryl group, an S—alkyl group, an NH—alkyl group, an NH—aryl group, an N,N—dialkyl group, or an N,N—diaryl group;

or $R_{54}$ together with $R_{58}$ and the nitrogen atom to which they are attached form a heterocycloalkyl group or a heteroaryl group;

$R_{57}$ is H or an alkyl group;

$R_{58}$ is H, an alkyl group, a cycloalkyl group, —$OR_{70}$, or $NR_{70}R_{71}$, wherein $R_{70}$ and $R_{71}$ are independently H or an alkyl group; and Z and $Z_1$ are independently H, F, an alkyl group, a cycloalkyl group, a heterocycloalkyl group, an aryl group, a heteroaryl group, —$C(O)R_{21}$, —$CO_2R_{21}$, —CN, —$C(O)NR_{21}R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$PO(OR_{21})_2$, —$PO(R_{21})(R_{22})$, —PO $(NR_{21}R_{22})(OR_{23})$ —$PO(NR_{21}R_{22})(NR_{23}R_{24})$, —$C(O)$ $NR_{21}NR_{22}R_{23}$, or —$C(S)NR_{21}NR_{22}R_{23}$,
  wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group, or wherein Z and $Z_1$, together with the atoms to which they are bonded, form a heterocycloalkyl group;

with the proviso that when $R_{57}$ is H, $R_{58}$ is a moiety other than H; and pharmaceutically acceptable prodrugs, salts, active metabolites, and solvates thereof.

As used in the present application, the following definitions apply:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynl, hexynyl, and the like, which may be unsubstituted (i.e., containing only carbon and hydrogen) or substituted by one or more suitable substituents as defined below.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, the following moieties:

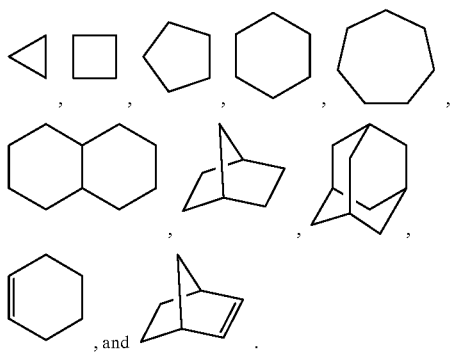

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen, and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to the following moieties:

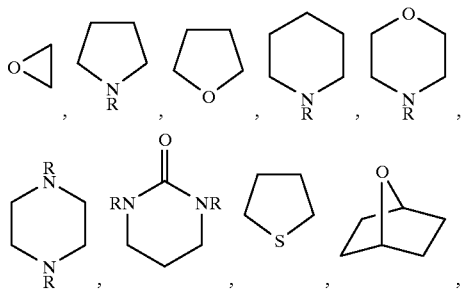

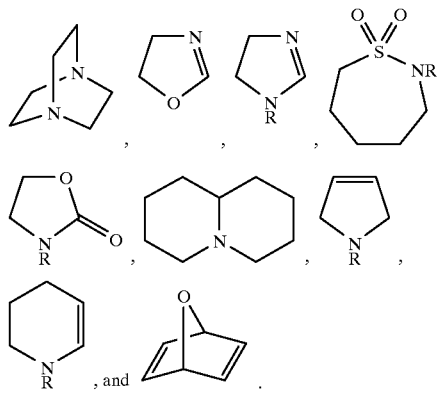

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, the following moieties:

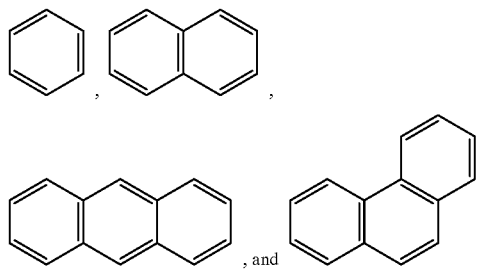

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, the following moieties:

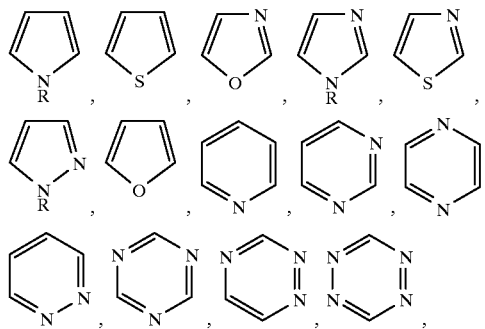

-continued

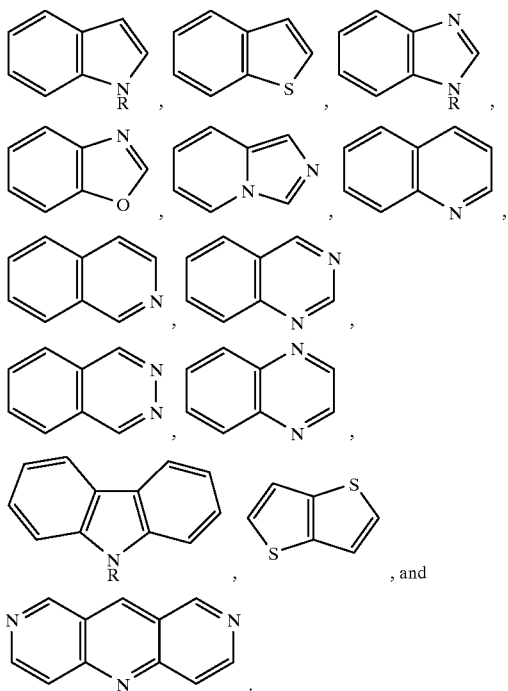

, and

An "acyl group" is intended to mean a —C(O)—R radical, wherein R is any suitable substituent as defined below.

A "thioacyl group" is intended to mean a —C(S)—R radical, wherein R is any suitable substituent as defined below.

A "sulfonyl group" is intended to mean a —SO$_2$R radical, wherein R is any suitable substituent as defined below.

The term "suitable substituent" is intended to mean any of the substituents recognizable, such as by routine testing, to those skilled in the art as not adversely affecting the inhibitory activity of the inventive compounds. Illustrative examples of suitable substituents include, but are not limited to, hydroxy groups, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroarlyoxy groups, arylthio groups, heteroarylthio groups, and the like.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

A "hydroxy group" is intended to mean the radical —OH.

An "amino group" is intended to mean the radical —NH$_2$.

An "alkylamino group" is intended to mean the radical —NHR where R is an alkyl group as defined above.

An "dialkylamino group" is intended to mean the radical —NR$_a$R$_b$ where R$_a$ and R$_b$ are each independently an alkyl group as defined above.

An "alkoxy group" is intended to mean the radical —OR where R is an alkyl group as defined above, for example, methoxy, ethoxy, propoxy, and the like.

An "alkoxycarbonyl group" is intended to mean the radical —C(O)OR where R is an alkyl group as defined above.

An "alkylsulfonyl group" is intended to mean the radical —SO$_2$R where R is an alkyl group as defined above.

An "alkylaminocarbonyl group" is intended to mean the radical —C(O)NHR where R is an alkyl group as defined above.

A "dialkylaminocarbonyl group" is intended to mean the radical —C(O)NR$_a$R$_b$ where R$_a$ and R$_b$ are each independently an alkyl group as defined above.

A "mercapto group" is intended to mean the radical —SH.

An "alkylthio group" is intended to mean the radical —SR where R is an alkyl group as defined above.

A "carboxy group" is intended to mean the radical —C(O)OH.

A "carbamoyl group" is intended to mean the radical —C(O)NH$_2$.

An "aryloxy group" is intended to mean the radical —OR$_c$ where R$_c$ is an aryl group as defined above.

A "heteroarlyoxy group" is intended to mean the radical —OR$_d$ where R$_d$ is a heteroaryl group as defined above.

An "arylthio group" is intended to mean the radical —SR$_c$ where R$_c$ is an aryl group as defined above.

A "heteroarylthio group" is intended to mean the radical —SR$_d$ where R$_d$ is a heteroaryl group as defined above.

A "pharmaceutically acceptable prodrug" is intended to mean a compound that may be converted under physiological conditions or by solvolysis to a compound of formula I.

A "pharmaceutically acceptable active metabolite" is intended to mean a pharmacologically active product produced through metabolism in the body of a compound of formula I.

A "pharmaceutically acceptable solvate" is intended to mean a solvate that retains the biological effectiveness and properties of the biologically active components of compounds of formula I.

Examples of pharmaceutically acceptable solvates include, but are not limited to, water, isopropanol, ethanol, methanol, DMSO, ethyl acetate, acetic acid, and ethanolamine.

A "pharmaceutically acceptable salt" is intended to a mean a salt that retains the biological effectiveness and properties of the free acids and bases of compounds of formula I and that is not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2- sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention.

The inventive compounds may exist as single stereoisomers, racemates and/or mixtures of enantiomers and/or diastereomers. All such single stereoisomers, racemates and mixtures thereof are intended to be within the scope of the present invention. Preferably, the inventive compounds are used in optically pure form.

As generally understood by those skilled in the art, an optically pure compound is one that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.).

Preferably in the above formulas I and II, $R_1$ and $R_{51}$ are H or F. Preferably in the compounds of formula I, at least one of $R_4$ and $R_8$ is an acyl group or a sulfonyl group. Preferably in the above formulas I and II, $D_1$ and $D_2$ are —$OR_{25}$, =O, =S, ≡N, =$NR_{25}$, or —$NR_{25}R_{26}$, wherein $R_{25}$ and $R_{26}$ are independently H, an alkyl group, a cycloalkyl group, a heterocycloalkyl group, an aryl group, or a heteroaryl group, or, together with the nitrogen atom to which they are bonded, form a heterocycloalkyl group, and more preferably $D_1$ and $D_2$ are =O. Preferably $A_1$ and $A_2$ are C, CH, S, or S(O), and more preferably $A_1$ and $A_2$ are C.

Preferably $B_1$ and $B_2$ are $NR_{17}R_{18}$, wherein $R_{17}$ and $R_{18}$ are independently H, an alkyl group, a cycloalkyl group, a heterocycloalkyl group, an aryl group, a heteroaryl group, or an acyl group, or wherein $R_{17}$ and $R_{18}$, together with the atom(s) to which they are bonded, form a heterocycloalkyl group.

Preferably Z and $Z_1$ are independently H, an aryl group, or a heteroaryl group, —$C(O)R_{21}$, —$CO_2R_{21}$, —CN, —$C(O)NR_{21}$, $R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$C(O)NR_{21}NR_{22}R_{23}$, or —$C(S)NR_{21}NR_{22}R_{23}$; wherein $R_{21}$, $R_{22}$, and $R_{23}$ are independently H, an alkyl group, a cycloalkyl group, a heterocycloalkyl group, an aryl group, a heteroaryl group, or an acyl group, or wherein any two of $R_{21}$, $R_{22}$, and $R_{23}$, together with the atom(s) to which they are bonded, form a heterocycloalkyl group, or Z and $Z_1$, together with the atoms to which they are attached, form a heterocycloalkyl group. Preferably M is O.

Preferably $R_{52}$ is one of the following moieties:

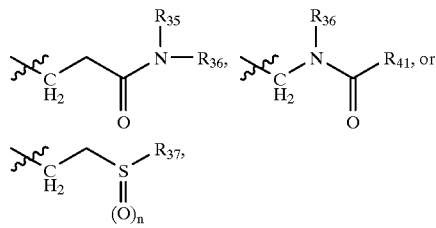

wherein $R_{35}$, $R_{36}$, $R_{37}$, $R_{41}$, and n are as defined above.

Compounds according to formula I include those described below, where * indicates the point of attachment. For example, the invention includes compounds 1–17 having the formula Ia:

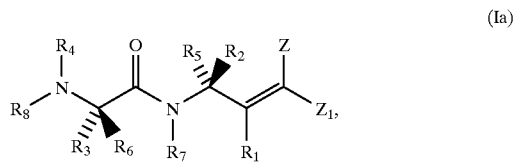

(Ia)

wherein $R_1$, $R_5$, $R_6$, and $R_7$ are H, $R_2$ is $CH_2CH_2C(O)NH_2$, $R_4$ is $CH_3$, and $R_3$, Z, $Z_1$, and $R_8$ are selected from one of the following groups:

1. $R_3$ is $CH_2Ph$, Z is H, $Z_1$ is $CO_2CH_2CH_3$, and $R_8$ is

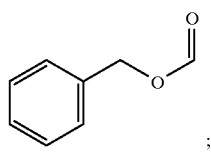

;

2. $R_3$ is $CH_2Ph$, Z is H, $Z_1$ is $CO_2CH_2CH_3$, and $R_8$ is

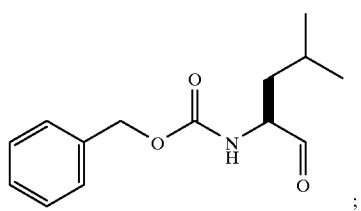

;

3. Z is H, $Z_1$ is $CO_2CH_2CH_3$, $R_3$ is

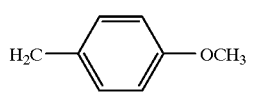

and R$_8$ is

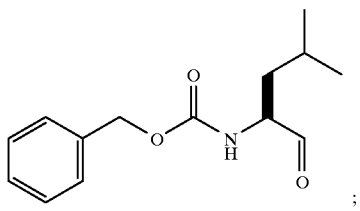

4. R$_3$ is

Z is H, Z$_1$ is CO$_2$CH$_2$CH$_3$, and R$_8$ is

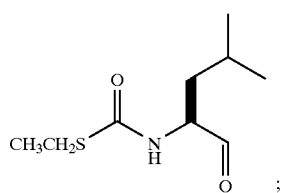

5. R$_3$ is CH$_2$Ph, Z is H, Z$_1$ is CO$_2$CH$_2$CH$_3$, and R$_8$ is

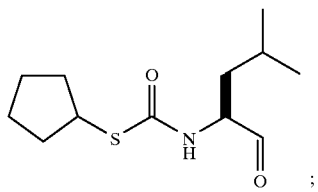

6. R$_3$ is CH$_2$Ph, Z and Z$_1$ together form

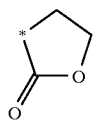

(where the C=O group is preferably cis to the R$_1$ group), and R$_8$ is

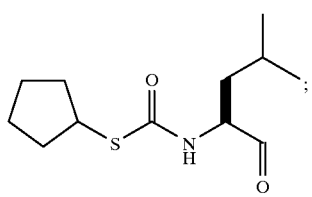

7. R$_3$ is CH$_2$Ph, Z is H, Z$_1$ is

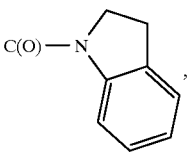

and R$_8$ is

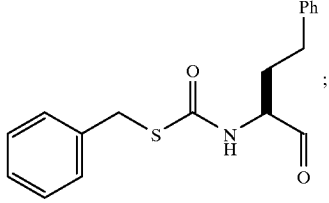

8. R$_3$ is CH$_2$Ph, Z and Z$_1$ together form

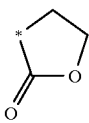

(where the C=O group is preferably cis to the R$_1$ group), and R$_8$ is

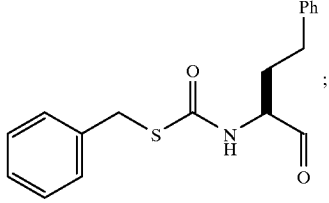

9. R$_3$ is CH$_2$Ph, Z is H, Z$_1$ is CO$_2$CH$_2$CH$_3$, and R$_8$ is

10. R$_3$ is CH$_2$Ph, Z and Z$_1$ together form

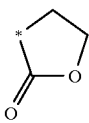

(where the C=O group preferably is cis to the R$_1$ group), and R$_8$ is

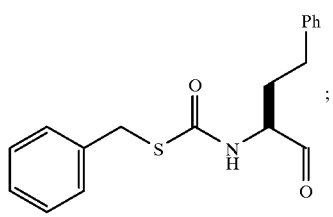

11. $R_3$ is $CH_2Ph$, Z is H, $Z_1$ is $CO_2CH_2CH_3$, and $R_8$ is

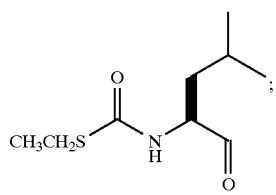

12. $R_3$ is $CH_2Ph$, Z and $Z_1$ together form

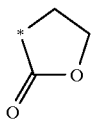

(where the C=O group preferably is cis to the $R_1$ group), and $R_8$ is

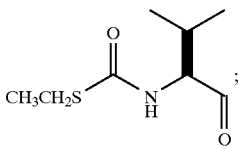

13. $R_3$ is

Z is H, $Z_1$ is $CO_2CH_2CH_3$, and $R_8$ is

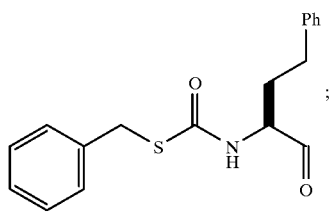

14. $R_3$ is

Z is $CH_3$, $Z_1$ is $CO_2CH_2CH_3$, and $R_8$ is

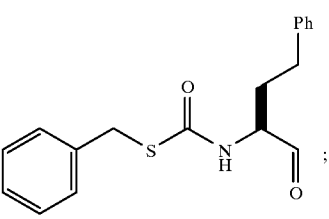

15. $R_3$ is $CH_2Ph$, Z is H, $Z_1$ is $CO_2CH_2CH_3$, and $R_8$ is

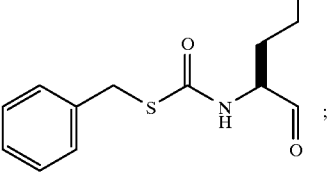

16. $R_3$ is $CH_2Ph$, Z is $CH_3$, $Z_1$ is $CO_2CH_2CH_3$, and $R_8$ is

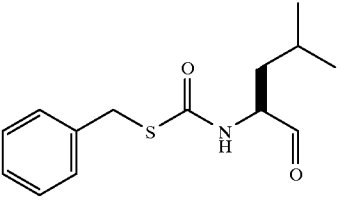

and

17. $R_3$ is $CH_2Ph$, Z is H, $Z_1$ is

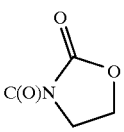

and $R_8$ is

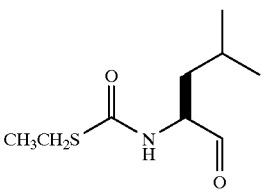

Additional compounds according to the invention include compounds 18–24 having the formula Ib:

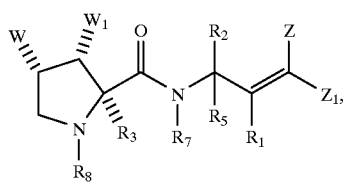

wherein $R_1$, $R_3$, $R_5$, $R_7$, and Z are H, $R_2$ is $CH_2CH_2C(O)NH_2$, and $Z_1$, W, $W_1$, and $R_8$ are selected from one of the following groups:

18. $Z_1$ is $CO_2CH_2CH_3$, W is H, $W_1$ is Ph, and $R_8$ is

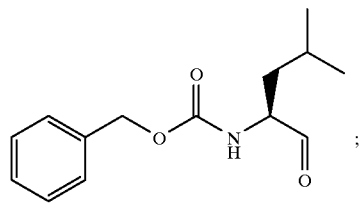

19. $Z_1$ is $CO_2CH_2CH_3$, W is H, $W_1$ is H, and $R_8$ is

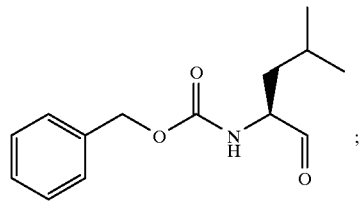

20. $Z_1$ is $CO_2CH_2CH_3$, W is $OCH_2Ph$, $W_1$ is H, and $R_8$ is

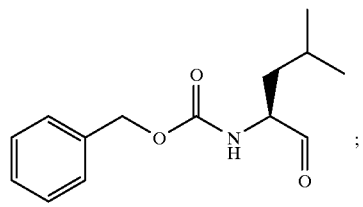

21. $Z_1$ is $CO_2CH_2CH_3$, W is H, $W_1$ is $CH_3$, and $R_8$ is

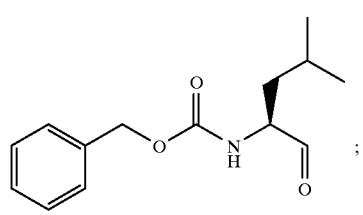

22. $Z_1$ is $C(O)N(CH_3)OCH_3$, W is H, $W_1$ is Ph, and $R_8$ is

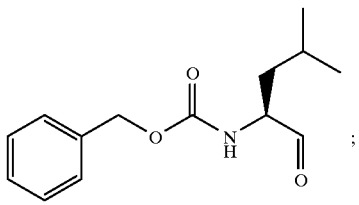

23. $Z_1$ is $CO_2CH_2CH_3$, W is $OC(CH_3)_3$, $W_1$ is H, and $R_8$ is

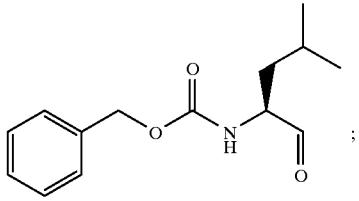

and

24. $Z_1$ is $CO_2CH_2CH_3$, W is H, $W_1$ is H, and $R_8$ is

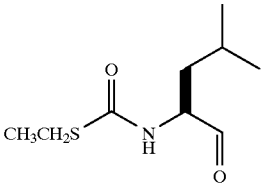

The invention further includes compounds 25–29 having the formula Ic:

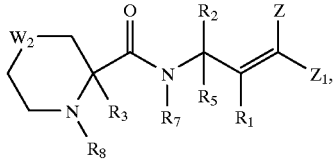

wherein $R_1$, $R_3$, $R_5$, $R_7$, and Z are H, $R_2$ is $CH_2CH_2C(O)NH_2$, $R_8$ is

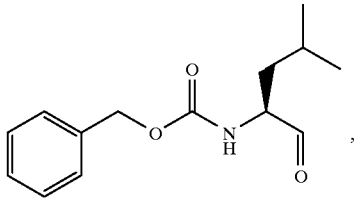

and $W_2$ and $Z_1$ are selected from one of the following groups:

25. $W_2$ is $CH_2$ and $Z_1$ is $CO_2CH_2CH_3$;
26. $W_2$ is $CH_2$ and $Z_1$ is

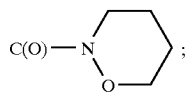

27. $W_2$ is NH and $Z_1$ is $CO_2CH_2CH_3$;
28. $W_2$ is $NCH_2Ph$ and $Z_1$ is $CO_2CH_2CH_3$; and
29. $W_2$ is $NSO_2Ph$ and $Z_1$ is $CO_2CH_2CH_3$.

Additionally, the invention includes compounds 30 and 31 according to formula Id:

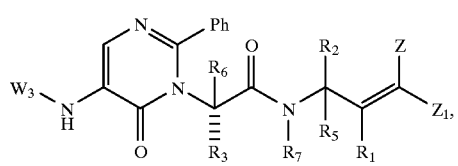

wherein $R_1$, $R_3$, $R_5$, $R_6$, $R_7$, and Z are H, $R_2$ is $CH_2CH_2C(O)NH_2$, $Z_1$ is $CO_2CH_2CH_3$, and $W_3$ is

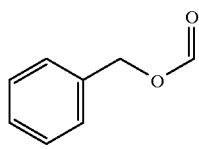

in Compound 30, and $W_3$ is H in Compound 31.

The invention also includes compounds 32 and 33 according to formula Ie:

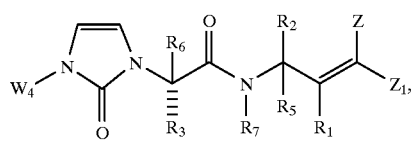

wherein $R_1$, $R_5$, $R_6$, $R_7$, and Z are each H, $R_2$ is $CH_2CH_2C(O)NH_2$, $R_3$ is $CH_2Ph$, $Z_1$ is $CO_2CH_2CH_3$, and $W_4$ is H in Compound 32, and $W_4$ is

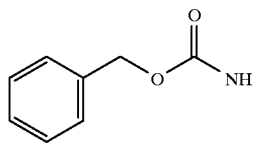

in Compound 33.

The invention further includes compounds 34–36, 38–49, and 56–58 also according to formula Ia above, wherein $R_1$, $R_5$, $R_6$, and $R_7$ are each H, $R_2$ is $CH_2CH_2C(O)NH_2$, $R_4$ is $CH_3$, and $R_3$, Z, $Z_1$, and $R_8$ are selected from one of the following groups:

34. $R_3$ is $CH_2Ph$, Z is H, $Z_1$ is $CO_2CH_2CH_3$, and $R_8$ is

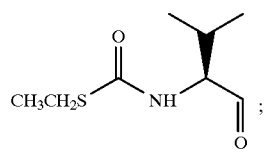

35. $R_3$ is $CH_2Ph$, Z is H, $Z_1$ is $CO_2CH_2CH_3$, and $R_8$ is

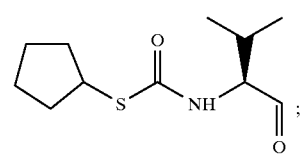

36. $R_3$ is $CH_2Ph$, Z is H, $Z_1$ is $C(O)N(CH_3)OCH_3$, and $R_8$ is

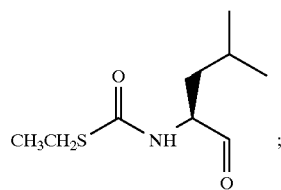

38. $R_3$ is $CH_2Ph$, Z is H, $Z_1$ is $CO_2CH_2CH_3$, and $R_8$ is

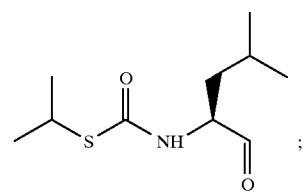

39. $R_3$ is $CH_2Ph$, Z is $CH_3$, $Z_1$ is $CO_2CH_2CH_3$, and $R_8$ is

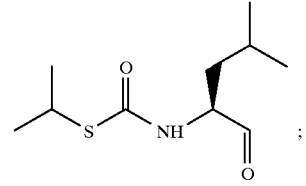

40. $R_3$ is $CH_2Ph$, Z is H, $Z_1$ is $CO_2CH_2CH_3$, and $R_8$ is

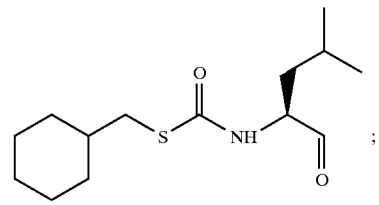

41. $R_3$ is $CH_2Ph$, Z is $CH_3$, $Z_1$ is $CO_2CH_2CH_3$, and $R_8$ is

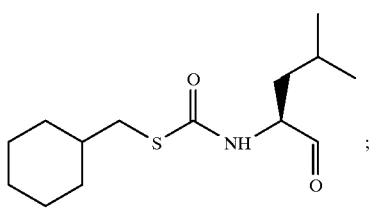

42. $R_3$ is $CH_2Ph$, Z is H, $Z_1$ is $CO_2CH_2CH_3$, and $R_8$ is

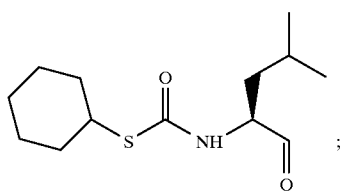

43. $R_3$ is $CH_2Ph$, Z is $CH_3$, $Z_1$ is $CO_2CH_2CH_3$, and $R_8$ is

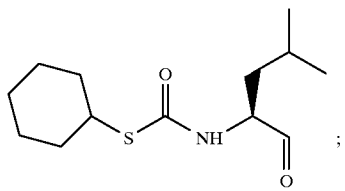

44. $R_3$ is $CH_2Ph$, Z is H, $Z_1$ is $CO_2CH_2CH_3$, and $R_8$ is

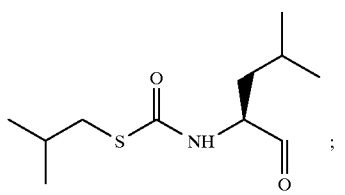

45. $R_3$ is $CH_2Ph$, Z is $CH_3$, $Z_1$ is $CO_2CH_2CH_3$, and $R_8$ is

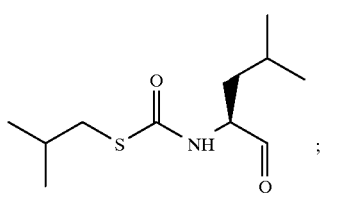

46. $R_3$ is $CH_2Ph$, Z is H, $Z_1$ is $CO_2CH_2CH_3$, and $R_8$ is

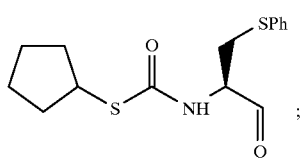

47. $R_3$ is $CH_2Ph$, Z is $CH_3$, $Z_1$ is $CO_2CH_2CH_3$, and $R_8$ is

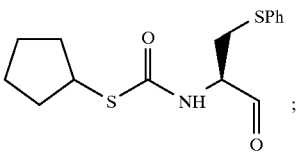

48. $R_3$ is

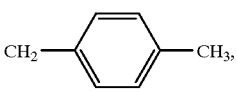

Z is H, $Z_1$ is $CO_2CH_2CH_3$, and $R_8$ is

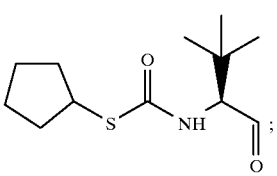

49. $R_3$ is

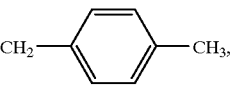

Z is $CH_3$, $Z_1$ is $CO_2CH_2CH_3$, and $R_8$ is

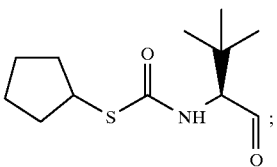

56. $R_3$ is $CH_2Ph$, Z is H, $Z_1$ is $CO_2CH_2Ph$, and $R_8$ is

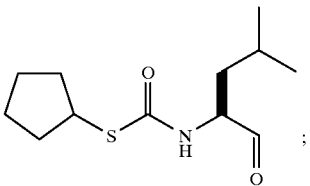

57. $R_3$ is $CH_2Ph$, Z is H, $Z_1$ is $CO_2CH_2CH_2CH_3$, and $R_8$ is

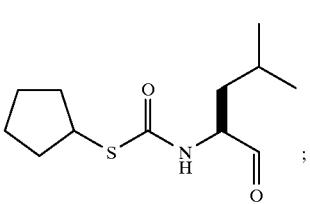

and

58. $R_3$ is $CH_2Ph$, Z is H, $Z_1$ is $CO_2CH_2CH_2OCH_3$, and $R_8$ is

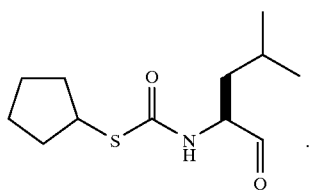

The invention also includes compounds 37 and 50–52 having the formula Ig:

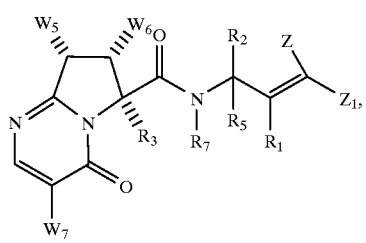
(Ig)

wherein $R_1$, $R_3$, $R_5$, $R_7$, $W_5$, $W_6$, and Z are H, $R_2$ is $CH_2CH_2C(O)NH_2$, $Z_1$ is $CO_2CH_2CH_3$, and $W_7$ is

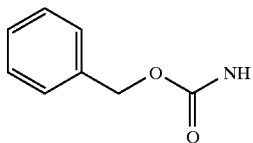

in Compound 37, $W_7$ is

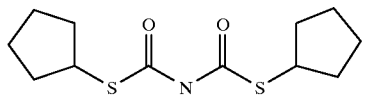

in Compound 50, $W_7$ is

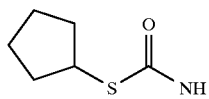

in Compound 51, and $W_7$ is

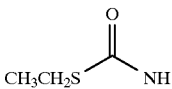

in Compound 52.

Compound 53 also corresponds to this invention. This compound has the formula Ih:

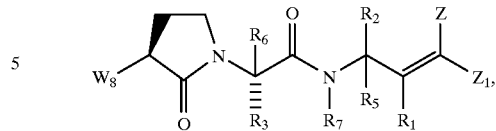
(Ih)

wherein $R_1$, $R_5$, $R_6$, and $R_7$ are H, $R_2$ is $CH_2CH_2C(O)NH_2$, $R_3$ is $CH_2Ph$, Z is H, $Z_1$ is $CO_2CH_2CH_3$, and $W_8$ is

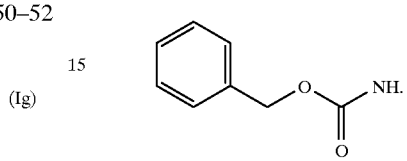

The invention also relates to compounds 54 and 55 having the formula (Ij):

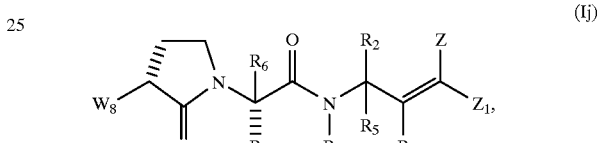
(Ij)

wherein $R_1$, $R_5$, $R_6$, and $R_7$ are H, $R_2$ is $CH_2CH_2C(O)NH_2$, $R_3$ is $CH_2Ph$, Z is H, $Z_1$ is $CO_2CH_2CH_3$, and $W_8$ is

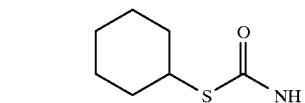

in Compound 54, and $W_8$ is

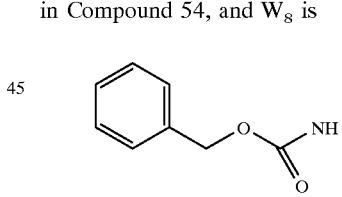

in Compound 55.

Other compounds according to the invention include the following compounds of formula X:

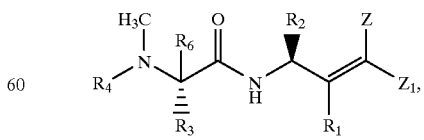
(X)

wherein $R_1$, $R_6$, and Z are H, $R_2$ is $CH_2CH_2C(O)NH_2$, $R_3$ is $CH_2Ph$, $Z_1$ is $CO_2CH_2CH_3$, and $R_4$ is from one of the following:

59. R4 is 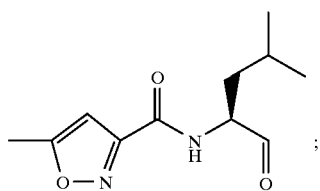;
60. R4 is 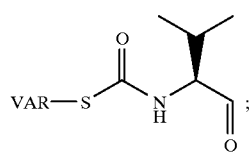;
61. R4 is 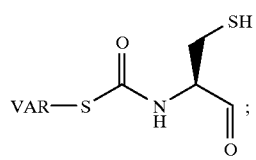;
62. R4 is 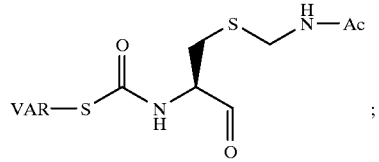;
63. R4 is 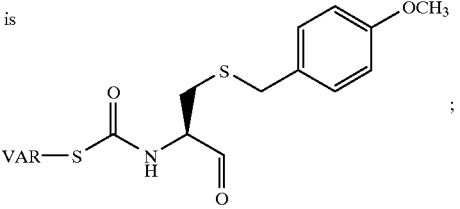;
64. R4 is 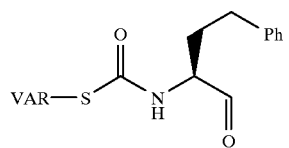;
65. R4 is 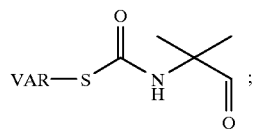;
66. R4 is 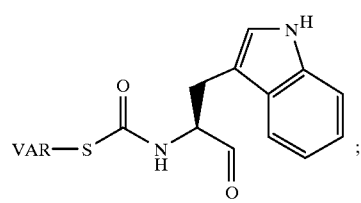;
67. R4 is 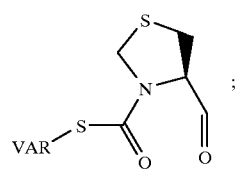;
68. R4 is 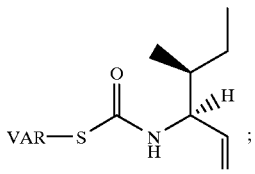;
69. R4 is 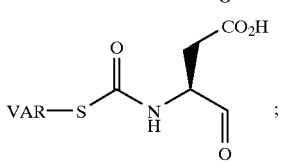;
70. R4 is 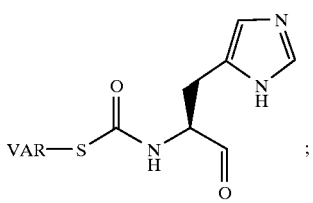;
71. R4 is 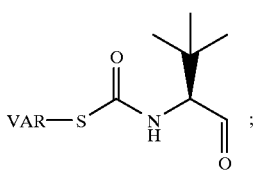;
72. R4 is 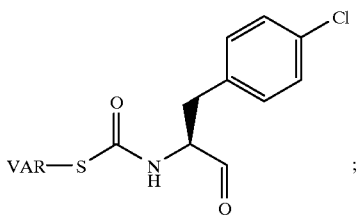;
73. R4 is 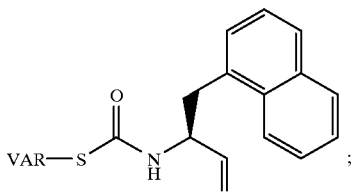;
74. R4 is 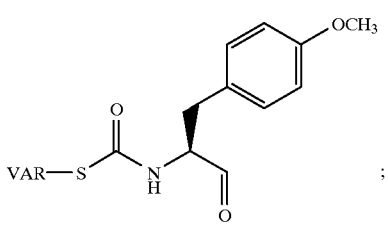;
75. R4 is 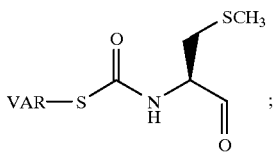;
76. R4 is 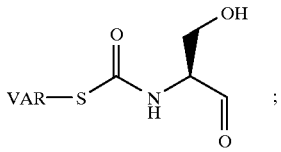;

77. R₄ is 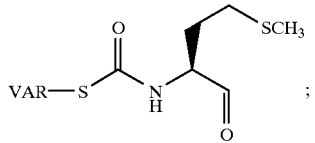;
78. R₄ is 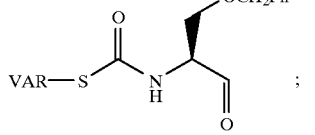;
79. R₄ is 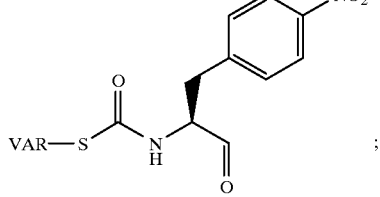;
80. R₄ is 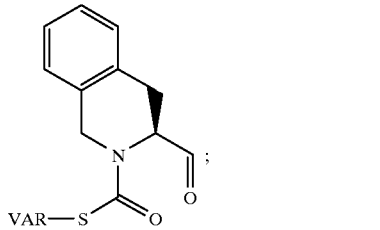;
81. R₄ is 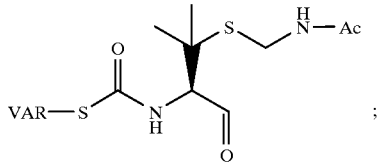;
82. R₄ is 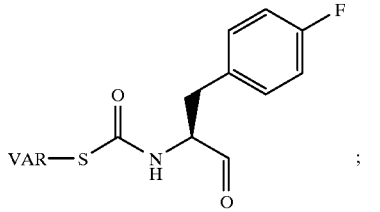;
83. R₄ is 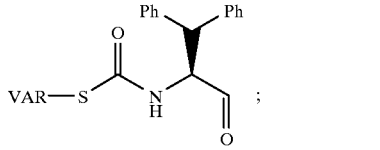;
84. R₄ is 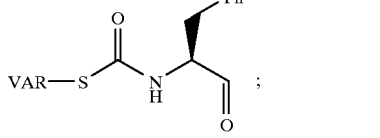;
85. R₄ is 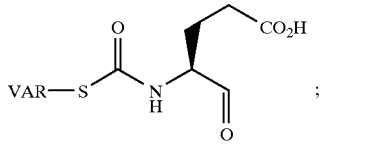;
86. R₄ is 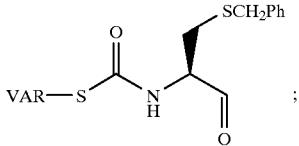;
87. R₄ is 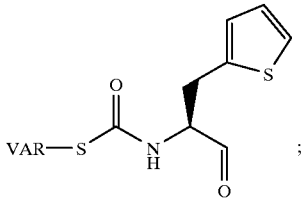;
88. R₄ is 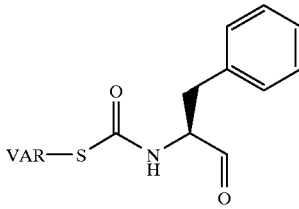;
89. R₄ is 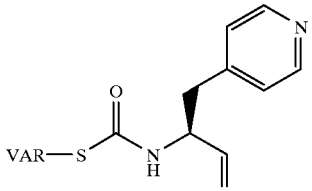;
90. R₄ is 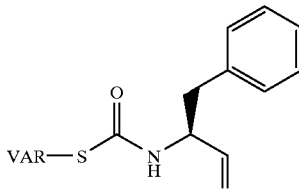;
91. R₄ is 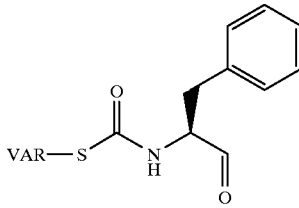;
92. R₄ is 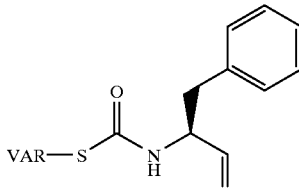;
93. R₄ is 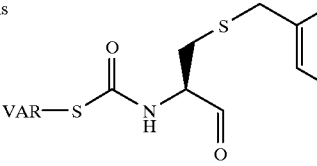;

94. $R_4$ is 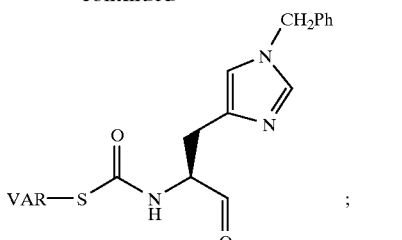;

95. $R_4$ is 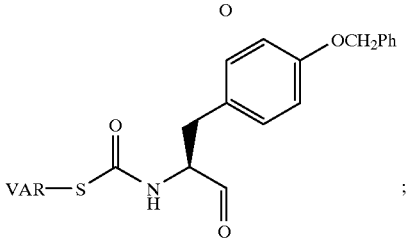;

96. $R_4$ is 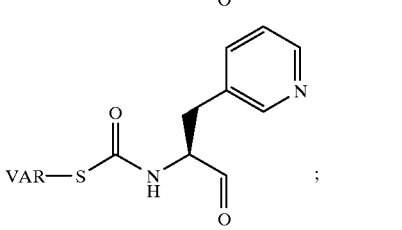;

97. $R_4$ is 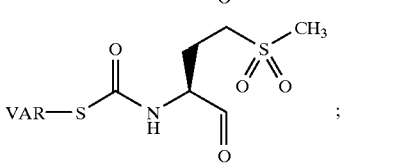;

98. $R_4$ is 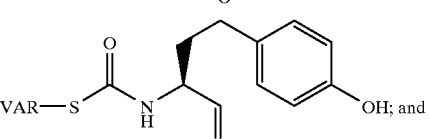 OH; and

99. $R_4$ is 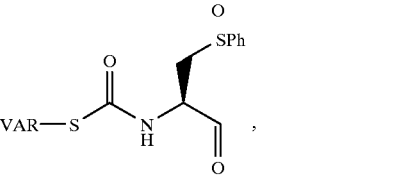, wherein VAR is selected from the group consisting of —$CH_2CH_3$, —$CH(CH_3)_2$,

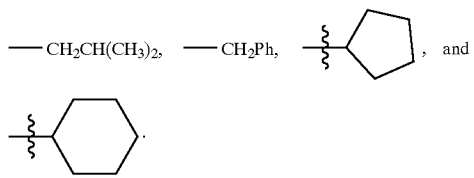

The present invention is further directed to methods of inhibiting picornaviral 3C protease activity that comprises contacting the protease for the purpose of such inhibition with an effective amount of a compound of formula I or a pharmaceutically acceptable prodrug, salt, active metabolite, or solvate thereof. For example, one can inhibit picornaviral 3C protease activity in mammalian tissue by administering a compound of formula I or a pharmaceutically acceptable prodrug, salt, active metabolite, or solvate thereof. More particularly, the present invention is directed to methods of inhibiting rhinoviral protease activity.

The activity of the inventive compounds as inhibitors of picornaviral 3C protease activity may be measured by any of the methods available to those skilled in the art, including in vivo and in vitro assays. Examples of suitable assays for activity measurements include the Antiviral HI-HeLa Cell Culture Assay and the Normal Human Bronchial Epithelial Cell Assay, both described herein.

Administration of the compounds of formula I, or their pharmaceutically acceptable prodrugs, salts, active metabolites, and solvates, may be performed according to any of the accepted modes of administration available to those skilled in the art. Illustrative examples of suitable modes of administration include, but are not limited to, oral, nasal, parenteral, topical, transdermal, and rectal.

The inventive compounds of formula I and their pharmaceutically acceptable prodrugs, salts, active metabolites, and solvates, may be administered as a pharmaceutical composition in any suitable pharmaceutical form recognizable to the skilled artisan. Suitable pharmaceutical forms include, but are not limited to, solid, semisolid, liquid, or lyopholized formulations, such as tablets, powders, capsules, suppositories, suspensions, and aerosols. The pharmaceutical composition may also include suitable excipients, diluents, vehicles, and carriers, as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraural, and/or rectal administration.

Solid or liquid pharmaceutically acceptable carriers, diluents, vehicles, or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers may include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of formula I or a pharmaceutically acceptable prodrug, salt, active metabolite, or solvate thereof) and preferably is made up of one or more pharmaceutical dosage units. The selected dose may be administered to a mammal, for example, a human patient, in need of treatment mediated by inhibition of 3C protease activity, by any known method of administering the dose including topical, for example, as an ointment or cream; orally; rectally, for example, as a suppository; parenterally by injection; or continuously by intravaginal, intranasal, intrabronchial, intraaural, or intraocular infusion.

A "therapeutically effective amount" is intended to mean that amount of a compound of formula I that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of formula I that will correspond to a "therapeutically effective amount" will vary depending upon factors such as the particular compound, the disease condition and the severity thereof, and the identity of the mammal in need thereof, but can nevertheless be readily determined by one of skill in the art.

"Treating" or "treatment" is intended to mean at least the mitigation of a disease condition in a mammal, such as a human, that is alleviated by the inhibition of the activity of one or more picornaviral 3C proteases, such as human rhinoviruses, human poliovirus, human coxsackieviruses, encephalomyocarditis viruses, menigovirus, and hepatitis A virus, and includes:

(a) prophylactic treatment in a mammal, particularly when the mammal is found to be predisposed to having the disease condition but not yet diagnosed as having it;

(b) inhibiting the disease condition; and/or (c) alleviating, in whole or in part, the disease condition.

The inventive compounds, and their salts, solvates, crystal forms, active metabolites, and prodrugs, may be prepared by employing the techniques available in the art using starting materials that are readily available. Certain novel and exemplary methods of preparing the inventive compounds are described below.

Preferably, the inventive compounds of formula I are prepared by the novel methods of the present invention, including the four general methods shown below. In each of these general methods, $R_1$, $R_2$, $R_3$, $R_4$, $R_5$, $R_6$, $R_7$, $R_8$, Z, and $Z_1$ are as defined above (for formula I).

General Method I:

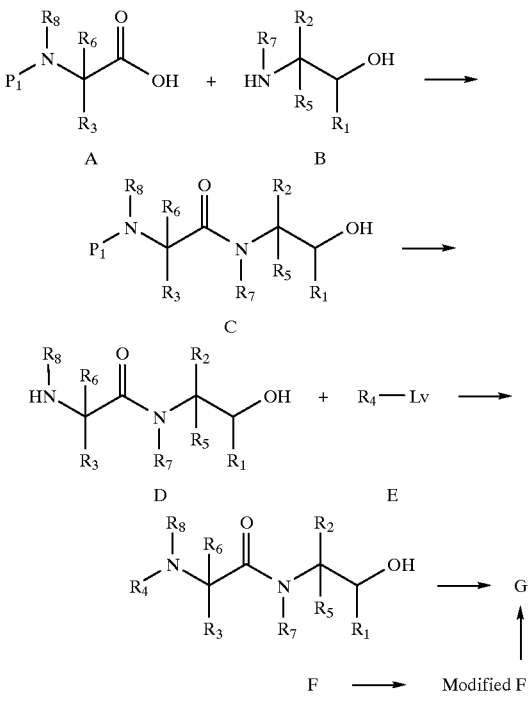

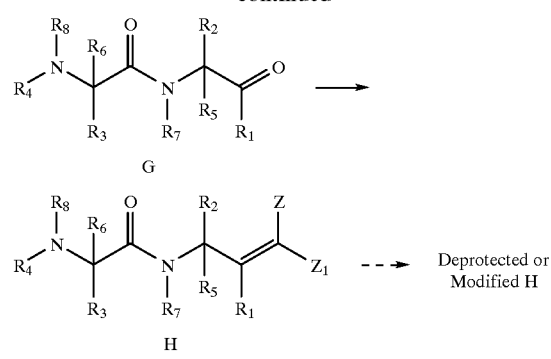

In General Method I, protected amino acid A, where $P_1$ is an appropriate protecting group for nitrogen, is subjected to an amide forming reaction with amino alcohol (or salt thereof) B to produce amide C. Amide C is then deprotected to give free amine (or salt thereof) D. Amine D and compound E, where "Lv" is an appropriate leaving group, are subjected to a bond forming reaction generating compound F. Compound F is oxidized to intermediate G, or modified at $R_4$ and/or $R_8$, to give one or more modified F compounds. Modified F compounds are oxidized to intermediate G. Intermediate G is then transformed into unsaturated product H. If protecting groups are used on any R groups ($R_1$–$R_8$) and/or on Z and/or $Z_1$, product H is deprotected and/or further modified to yield "deprotected or modified H."

An alternative method to prepare intermediate F is described as follows:

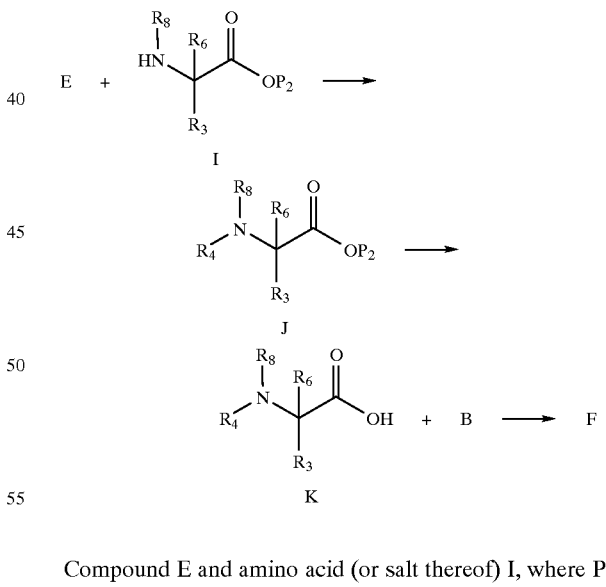

Compound E and amino acid (or salt thereof) I, where $P_2$ is an appropriate protecting group for oxygen, are subjected to a bond forming reaction to produce intermediate J. Intermediate J is deprotected to yield free carboxylic acid K, which is subsequently subjected to an amide forming reaction with amino alcohol (or salt thereof) B to generate intermediate F.

Amino alcohol B can be prepared as follows:

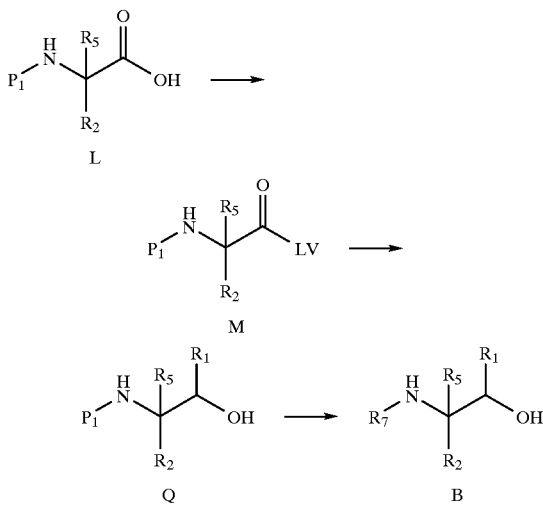

Amino acid L, where $P_1$ is an appropriate protecting group for nitrogen, is converted to carbonyl derivative M, where "Lv" is a leaving group. Compound M is subjected to a reaction where "Lv" is reduced to protected amino alcohol Q. Amino alcohol Q is deprotected to give amino alcohol B.

General Method II:

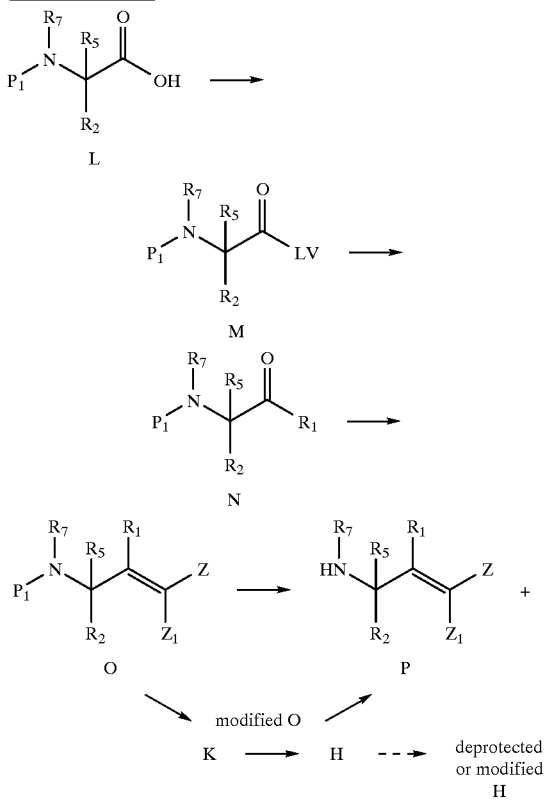

In General Method II, amino acid L, where $P_1$ is an appropriate protecting group for nitrogen, is converted to a carbonyl derivative M, where "Lv" is a leaving group. Compound M is subjected to a reaction where "Lv" is replaced by $R_1$ to give derivative N. Derivative N is then transformed into unsaturated product O. Unsaturated compound O is deprotected to give free amine (or salt thereof) P, or modified one or more times at $R_2$, $R_5$, $R_7$, Z, and/or $Z_1$ to give one or more modified O compounds.

Modified O is then deprotected to give amine (or salt thereof) P. Amine P is subsequently subjected to an amide forming reaction with carboxylic acid K, prepared as described in General Method I, to give final product H. If protecting groups were used on any R group ($R_1$–$R_8$) and/or on Z and/or $Z_1$, product H is deprotected and/or further modified to yield "deprotected or modified H." An alternative method to prepare intermediate N is described as follows:

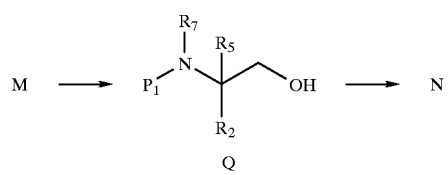

Compound M is subjected to a reaction where "Lv" is reduced to protected amino alcohol Q. Amino alcohol Q is subsequently oxidized to derivative N. General Method III:

General Method III:

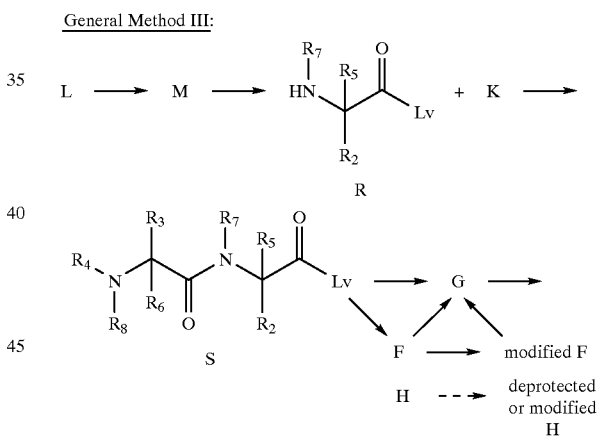

In General Method III, amino acid L, where $P_1$ is an appropriate protecting group for nitrogen, is converted to a carbonyl derivative M, where "Lv" is a leaving group. Derivative M is deprotected to give free amine (or salt thereof) R, which subsequently is subjected to an amide forming reaction with carboxylic acid K to give intermediate S. Intermediate S is then either converted directly to carbonyl intermediate G, or successively reduced to alcohol F, which is then oxidized to G. Intermediate G is subjected to a reaction to yield the unsaturated final product H. If protecting groups were used on any R groups ($R_1$–$R_8$) and/or on Z and/or $Z_1$, product H is deprotected and/or further modified to yield "deprotected or modified H."

General Method IV:

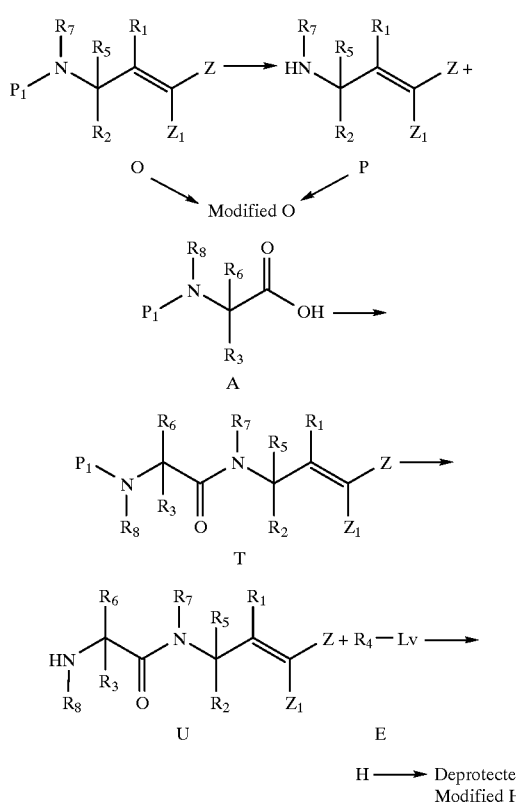

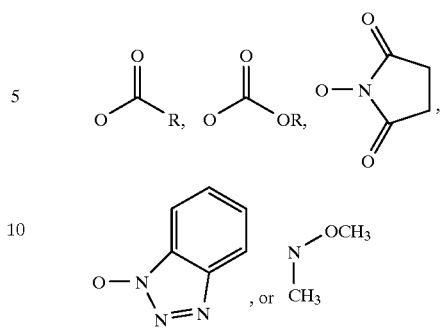

wherein "R" is any suitable substituent, such as an alkyl group or an aryl group. Other examples of suitable leaving groups are described in J. March, *Advanced Organic Chemistry, Reactions, Mechanisms, and Structure* (4th ed. 1992) at pages 205, 351–56, 642–43, 647, 652–53, 666, 501, 520–21, 569, 579–80, 992–94, 999–1000, 1005, and 1008, which are incorporated herein by reference.

EXAMPLES

Proton magnetic resonance spectra (NMR) were determined using a Tech-Mag spectrometer operating at a field strength of 300 megahertz (MHZ) or Varian UNITYplus 300. Chemical shifts are reported in parts per million ($\delta$) and setting the references such that in $CDCl_3$ the $CHCl_3$ is at 7.26 ppm, in $CD_3OD$ the $CH_3OH$ is at 4.9 ppm, in $C_6D_6$ the $C_6H_6$ is at 7.16 ppm, in acetone-$d_6$ the acetone is at 2.02 ppm, and in DMSO-$d_6$ the DMSO is at 2.49 ppm. Standard and peak multiplicities are designated as follows: s, singlet; d, doublet; dd, doublet of doublets; ddd, doublet of doublet of doublets; t, triplet; q, quartet; bs, broad singlet; bt, broad triplet; m, multiplet. Mass spectra (FAB; fast atom bombardment) were determined at the Scripps Research Institute Mass Spectometry Facility, San Diego, Calif. Infrared absorption (IR) spectra were taken on a MIDAC Corporation FTIR or a Perkin-Elmer 1600 series FTIR spectrometer. Elemental microanalyses were performed by Atlantic Microlab Inc. Norcross, Ga. and gave results for the elements stated with ±0.4% of the theoretical values. Flash chromatography was performed using Silica gel 60 (Merck Art 9385). Thin layer chromatographs ("TLC") were performed on precoated sheets of silica 60 $F_{254}$ (Merck Art 5719). Melting points were determined on a Mel-Temp apparatus and are uncorrected. Anhydrous N,N-dimethylformamide (DMF), N,N-dimethylacetamide (DMA), dimethysulfoxide (DMSO), were used as is. Tetrahydrofuran (THF) was distilled from sodium benzophenone ketyl under nitrogen. "$Et_2O$" refers to diethyl ether. "Pet. ether" refers to petroleum ether with a boiling range of 36–53° C. "TFA" refers to trifluoroacetic acid. "$Et_3N$" refers to triethylamine. Other abbreviations include: methanol (MeOH), ethanol (EtOH), ethyl acetate (EtOAc), acetyl (Ac), methyl (Me), triphenylmethyl (Tr), benzyloxycarbonyl (CBZ), tert-butoxycarbonyl (BOC), m-chloroperoxybenzoic acid (m-CPBA), alanine (Ala), glutamine (Gln), proline (Pro), leucine (Leu), methionine (Met), phenylalanine (Phe), and homophenylalanine (hPhe), where "L" represents natural amino acids and "D" unnatural amino acids. "DL" represents racemic mixtures. A simplified naming system was used to identify intermediates and final products: Amino In General Method IV, free amine (or salt thereof) P, prepared from intermediate O as described in General Method II, is converted to amide T by reaction with amino acid A, where $P_1$ is an appropriate protecting group for nitrogen. Compound T is further deprotected to free amine (or salt thereof) U, which is subsequently converted to H with reactive intermediate E. If protecting groups were used on any R groups ($R_1$–$R_8$) and/or on Z and/or $Z_1$, product H is deprotected and/or further modified to yield "deprotected or modified H."

Suitable protecting groups for nitrogen are recognizable to those skilled in the art and include, but are not limited to benzyloxycarbonyl, t-butoxycarbonyl, 9-fluorenylmethoxycarbonyl, p-methoxybenxyloxycarbonyl, trifluoroacetamide, and p-toluenesulfonyl. Suitable protecting groups for oxygen are recognizable to those skilled in the art and include, but are not limited to —$CH_3$, —$CH_2CH_3$, tBu, —$CH_2Ph$, —$CH_2CH=CH_2$, —$CH_2OCH_2CH_2Si(CH_3)_3$, and —$CH_2CCl_3$. Other examples of suitable protecting groups for nitrogen or oxygen can be found in T. Green & P. Wuts, *Protective Groups in Organic Synthesis* (2nd ed. 1991), which is incorporated herein by reference.

Suitable leaving groups are recognizable to those skilled in the art and include, but are not limited to, Cl, Br, I, sulfonates, O—alkyl groups, acid and peptide alcohols are given the suffix 'ol' (for example "methionol"). Amino acid and peptide aldehydes are given the suffix 'al' (for example "methional"). When naming final products, italicized amino acid abbreviations represent modifications at the C-terminus of that residue where the following apply:

1. acrylic acid esters are reported as either "E" (trans) or "Z" (cis) propenoates.
2. lactones 6, 8, 10, and 12 are reported as E-α-vinyl-γ-butyrolactones.
3. acrylamides are reported as either E or Z propenamides except in the case of compound 7, which is reported as 1-(2',3'-Dihydroindolin-1-yl)-3-[ethylthiocarbonyl-L-Leu-L-N-Me-Phe-L-(Tr-Gln)]-E-propenone and compound 26, which is reported as 1-[1',2'-oxazin-2'-yl]-3-(CBZ-L-Leu-L-Pip-L-Gln)-E-propenone.
4. acryloxazolidone 17 is reported as 1-[2'-oxazolidon-3'-yl]-3-(ethylthiocarbonyl-L-Leu-L-N-Me-Phe-Gln)-E-propenone.

Example 1

Preparation of Compound 1: Ethyl-3-(CBZ-L-N-Me-Phe-L-Gln)-E-Propenoate.

Preparation of Intermediate BOC-L-(Tr-Gln)-N(OMe)Me.

Isobutyl chloroformate (4.77 mL, 36.8 mmol, 1.0 equiv) was added to a solution of BOC-L-(Tr-Gln) (18.7 g, 36.7 mmol, 1 equiv) and 4-methylmorpholine (8.08 mL, 73.5 mmol, 2.0 equiv) in $CH_2Cl_2$ (250 mL) at 0° C. The reaction mixture was stirred at 0° C. for 20 min, then N,O-dimethylhydroxylamine hydrochloride (3.60 g, 36.7 mmol, 1.0 equiv) was added. The resulting solution was stirred at 0° C. for 20 min and at 23° C. for 2 h, and then it was partitioned between water (150 mL) and $CH_2Cl_2$ (2×150 mL). The combined organic layers were dried over $Na_2SO_4$ and concentrated. Purification of the residue by flash column chromatography (gradient elution, 20–40% hexanes in EtOAc) provided BOC-L-(Tr-Gln)-N(OMe)Me (16.1 g, 82%) as a white foam: IR (KBr) 3411, 3329, 3062, 1701, 1659 $cm^{-1}$; $^1H$ NMR ($CDCl_3$) δ 1.42 (s, 9 H), 1.63–1.77 (m, 1 H), 2.06–2.17 (m, 1 H), 2.29–2.43 (m, 2 H), 3.17 (s, 3 H), 3.64 (s, 3 H), 4.73 (s, bs, 1 H), 5.38–5.41 (m, 1 H), 7.20–7.31 (m, 15 H); Anal. ($C_{31}H_{37}N_3O_5$) C, H, N.

Preparation of Intermediate BOC-L-(Tr-Glutaminal).

Diisobutylaluminum hydride (50.5 mL of a 1.5 M solution in toluene, 75.8 mmol, 2.5 equiv) was added to a solution of [BOC-L-(Tr-Gln)]-N(OMe)Me (16.1 g, 30.3 mmol, 1 equiv) in THF at −78° C., and the reaction mixture was stirred at −78° C. for 4 h. Methanol (4 mL) and 1.0 M HCl (10 mL) were added sequentially, and the mixture was warmed to 23° C. The resulting suspension was diluted with $Et_2O$ (150 mL) and was washed with 1.0 M HCl (3×100 mL), half-saturated $NaHCO_3$ (100 mL), and water (100 mL). The organic layer was dried over $MgSO_4$, filtered, and was concentrated to give crude BOC-L-(Tr-Glutaminal) (13.8 g, 97%) as a white solid: mp=114–116° C.; IR (KBr) 3313, 1697, 1494 $cm^{-1}$; $^1H$ NMR ($CDCl_3$) δ 1.44 (s, 9 H), 1.65–1.75 (m, 1 H), 2.17–2.23 (m, 1 H), 2.31–2.54 (m, 2 H), 4.11 (bs, 1 H), 5.38–5.40 (m, 1 H), 7.11 (s, 1 H), 7.16–9.45 (s, 1 H).

Preparation of Intermediate Ethyl-3-[BOC-L-(Tr-Gln)]-E-Propenoate.

Sodium bis(trimethylsilyl)amide (22.9 mL of a 1.0 M solution in THF, 22.9 mmol, 1.0 equiv) was added to a solution of triethyl phosphonoacetate (5.59 g, 22.9 mmol, 1.0 equiv) in THF (200 mL) at −78° C., and the resulting solution was stirred for 20 min at that temperature. Crude [BOC-L-(Tr-Glutaminal)]-H (10.8 g, 22.9 mmol, 1 equiv) in THF (50 mL) was added via cannula, and the reaction mixture was stirred for 2 h at −78° C., warmed to 0° C. for 10 min, and partitioned between 0.5 M HCl (150 mL) and a 1:1 mixture of EtOAc and hexanes (2×150 mL). The organic layers were dried over $Na_2SO_4$ and were concentrated. Purification of the residue by flash column chromatography (40% EtOAc in hexanes) provided ethyl-3-[BOC-L-(Tr-Gln)]-E-propenoate (10.9 g, 88%) as a white foam: IR (thin film) 3321, 1710 $cm^{-1}$; $^1H$ NMR ($CDCl_3$) δ 1.27 (t, 3 H, J=7.2), 1.42 (s, 9 H), 1.70–1.78 (m, 1 H), 1.80–1.96 (m, 1 H), 2.35 (t, 2 H, J=7.0), 4.18 (q, 2 H, J=7.2), 4.29 (bs, 1 H), 4.82–4.84 (m, 1 H), 5.88 (dd, 1 H, J=15.7, 1.6), 6.79 (dd, 1 H, J=15.7, 5.3), 6.92 (s, 1 H), 7.19–7.34 (m, 15 H); Anal. ($C_{33}H_{38}N_2O_5$) C, H, N.

Preparation of Intermediate Ethyl-3-[BOC-L-N-Me-Phe-L-(Tr-Gln)]-E-Propenoate.

Ethyl-3-[BOC-L-(Tr-Gln)]-E-Propenoate (0.751 g, 1.38 mmol) was dissolved in 1,4-dioxane (5 mL). A solution of HCl in 1,4-dioxane (4.0 M, 5 mL) was added dropwise. The reaction solution was stirred for 2 h and then the solvent was evaporated to provide the amine salt as a foam which was used without purification. The crude amine salt was dissolved in dry $CH_2Cl_2$ (12 mL) under argon. 4-Methylmorpholine (1.05 mL, 9.55 mmol), hydroxybenzotriazole hydrate (0.280 g, 2.07 mmol), BOC-L-N-Me-Phe (0.386 g, 1.38 mmol) and 1-(3-dimethylaminopropyl)-3-ethylcarbodiimide hydrochloride (0.397 g, 2.07 mmol) were added successively. The reaction mixture was stirred overnight and poured into water (25 mL). The resulting mixture was extracted with $CH_2Cl_2$ (3×75 mL). The combined organic phases were dried over $Na_2SO_4$ and evaporated. The residue was purified by chromatography (25% acetone in hexanes, then 3% MeOH in $CH_2Cl_2$) to provide ethyl-3-[BOC-L-N-Me-Phe-L-(Tr-Gln)]-E-propenoate (0.450 g, 46%) as a foam: IR (thin film) 3318, 1708, 1667 $cm^{-1}$; $^1H$ NMR ($CDCl_3$) (major rotamer) δ 1.28 (t, 3H, J=7.2 Hz), 1.37 (s, 9H), 1.63–1.87 (m, 1H), 1.94–2.06 (m, 1H), 2.26–2.37 (m, 2H), 2.66 (s, 3H), 3.00 (dd, 1H, J=13.5, 9.2 Hz), 3.29 (dd, 1H, J=13.5, 6.4 Hz), 4.18 (q, 2H, J=7.2 Hz), 4.51–4.70 (m, 2H), 5.71 (d, 1H, J=15.6 Hz), 6.40 (d, 1H, J=8.1 Hz), 6.73 (dd, 1H, J=15.6, 4.8 Hz), 6.97 (s, 1H), 7.12–7.36 (m, 20H); Anal. ($C_{43}H_{49}N_3O_6$) C, H, N.

Preparation of Intermediate Ethyl-3-[CBZ-L-N-Me-Phe-L-(Tr-Gln)]-E-Propenoate.

Ethyl-3-[BOC-L-N-Me-Phe-L-(Tr-Gln)]-E-propenoate (0.433 g, 0.615 mmol) was dissolved in 1,4-dioxane (2.5 mL) and treated dropwise with a solution of hydrogen chloride in 1,4-dioxane (4.0 M, 2.5 mL). After stirring for 2 hours, the solvent was evaporated to provide ethyl-3-[L-N-Me-Phe-L-(Tr-Gln)]-E-propenoate hydrochloride which was used without purification. One half of the crude amine salt formed was dissolved in dry $CH_2Cl_2$ (3 mL). 4-Methylmorpholine (0.169 mL, 1.54 mmol) and benzyl chloroformate (0.088 mL, 0.62 mmol) were added sequentially. After stirring overnight, the solvent was evaporated. The residue was purified by chromatography (20% to 25% acetone in hexanes) to provide ethyl-3-[CBZ-L-N-Me-Phe-L-(Tr-Gln)]-E-propenoate (0.112 g, 49%) as a foam: IR (thin film) 3316, 1708, 1684, 1664 $cm^{-1}$; $^1H$ NMR ($CDCl_3$) (major rotamer) δ 1.29 (t, 3H, J=7.2 Hz), 1.59–1.72 (m, 1H), 1.82–2.01 (m, 1H), 2.19–2.26 (m, 2H), 2.73 (s, 3H), 2.99 (dd, 1H, J=14.2, 9.2 Hz), 3.29 (dd, 1H, J=14.2, 6.8 Hz), 4.18 (q, 2H, J=7.2 Hz), 4.48–4.60 (m, 1H), 4.66 (dd, 1H, J=9.2, 6.8 Hz), 4.93 (d, 1H, J=12.3 Hz), 5.02 (d, 1H, J=12.3 Hz), 5.71 (dd, 1H, J=15.6, 1.6 Hz), 6.48 (d, 1H, J=8.1 Hz), 6.70 (dd, 1H, J=15.6, 5.4 Hz), 6.87 (s, 1H), 7.05–7.37 (m, 25H); Anal. ($C_{46}H_{47}N_3$·0.5 $H_2O$) C, H, N.

Preparation of Product-Ethyl-3-(CBZ-L-N-Me-Phe-L-Gln)-E-Propenoate.

Ethyl-3-[CBZ-L-N-Me-Phe-L-(Tr-Gln)]-E-propenoate (0.096 g, 0.13 mmol) was dissolved in dry $CH_2Cl_2$ (4 mL). Triisopropylsilane (0.077 mL, 0.376 mmol) and trifluoroacetic acid (2 mL) were added sequentially to give a bright yellow solution. After stirring for 30 min, no yellow color remained. The solvents were evaporated to give a semi-solid residue which was purified by chromatography (5% methanol in $CH_2Cl_2$) to provide ethyl-3-(CBZ-L-N-Me-Phe-L-Gln)-E-propenoate (0.061 g, 95%) as a colorless glass: IR (thin film) 3412, 3336, 3213, 1696, 1684, 1655 cm$^{-1}$; $^1$H NMR (CDCl$_3$) (major isomer) δ 1.28 (t, 3H, J=7.2 Hz), 1.63–2.03 (m, 2H), 2.11–2.18 (m, 2H), 2.88 (s 3H), 3.05 (dd, 1H, J=14.0, 9.3 Hz), 3.31 (dd, 1H, J=14.0, 6.8 Hz), 4.18 (q, 2H, J=7.2 Hz), 4.51–4.63 (m, 1H), 4.71–4.80 (m, 1H), 4.95–5.16 (m, 2H), 5.73 (d, 1H, J=15.9 Hz), 5.77–5.92 (m, 1H), 6.10 (s, 1H), 6.65–6.78 (m, 2H), 7.09–7.38 (m, 10H); Anal. ($C_{27}H_{33}N_3O_6 \cdot 0.75\ H_2O$) C, H, N.

Example 2

Preparation of Compound 2: Ethyl-3-(CBZ-L-Leu-L-N-Me-Phe-L-Gln)-E-Propenoate.

Preparation of Intermediate Ethyl-3-[CBZ-L-Leu-L-N-Me-Phe-L-(Tr-Gln)]-E-Propenoate.

Ethyl-3-[BOC-L-N-Me-Phe-L-(Tr-Gln)]-E-propenoate (0.216 g, 0.308 mmol) was deprotected and coupled with CBZ-L-Leu (0.082 g, 0.309 mmol) using the procedure described for the formation of ethyl-3-[BOC-L-N-Me-Phe-L-(Tr-Gln)]-E-propenoate to provide ethyl-3-[CBZ-L-Leu-L-N-Me-Phe-L-(Tr-Gln)]-E-propenoate after two chromatographies (30% acetone/hexanes, then 2% methanol/$CH_2Cl_2$) as a glass (0.095 g, 36%): IR (thin film) 3304, 1708, 1659 cm$^{-1}$; $^1$H NMR (CDCl$_3$) (mixture of rotamers) δ 0.63 (d, 3H, J=6.7 Hz), 0.66 (d, 3H, J=6.8 Hz), 0.83–0.89 (m, 6H), 1.12–1.48 (m, 3H, J=7.2 Hz), 1.28 (t, 3H, J=7.2 Hz), 1.51–1.66 (m, 2H), 1.69–1.80 (m, 1H), 188–204 (m, 2H), 2.16–2.32 (m, 4H), 2.90 (s, 6H), 2.95–3.17 (m, 2H), 3.25 (dd, 1H, J=14.6, 3.4 Hz), 3.37 (dd, 1H, J=13.7, 6.5 Hz), 4.11–4.25 (m, 2H), 4.17 (q, 4H, J=7.2 Hz), 4.38–4.51 (m, 2H), 4.53–4.67 (m, 3H), 4.85–5.16 (m, 7H), 5.72 (d, 1H, J=15.9 Hz), 5.95 (dd, 1H, J=15.9, 1.2 Hz), 6.43 (d, 1H, J=8.4 Hz), 6.74 (dd, 1H, J=15.9, 5.3 Hz), 6.80 (s, 1H), 6.84 (dd, 1H, J=15.9, 6.5 Hz), 7.09–7.38 (m, 50H), 8.00 (d, 1H, J=7.8 Hz); Anal. ($C_{52}H_{58}N_4O_7 \cdot 0.5\ H_2O$) C, H, N.

Preparation of Product-Ethyl-3-(CBZ-L-Leu-L-N-Me-Phe-L-Gln)-E-Propenoate.

Ethyl-3-[CBZ-L-Leu-L-N-Me-Phe-L-(Tr-Gln)]-E-propenoate (0.056 g, 0.066 mmol) was deprotected using the procedure described in Example 1 for the formation of ethyl-3-(CBZ-L-N-Me-Phe-L-Gln)-E-propenoate to provide ethyl-3-[CBZ-L-Leu-L-N-Me-Phe-L-Gln]-E-propenoate (after chromatography, 5% MeOH in $CH_2Cl_2$) as a glass (0.029 g, 73%): IR (thin film) 3401, 3298, 3225, 1678, 1652 cm$^{-1}$; $^1$H NMR (CDCl$_3$) (mixture of isomers) δ 0.62–0.69 (m, 6H), 0.87–0.94 (m, 6H), 1.15–1.32 (m, 8H), 1.37–1.49 (m, 2H), 1.61–1.86 (m, 4H), 1.90–2.03 (m, 2H), 2.10–2.20 (m, 4H), 2.93 (s, 3H), 2.95 (s, 3H), 2.97–3.11 (m, 1H), 3.17–3.28 (m, 2H), 3.41–3.49 (m, 1H), 4.16–4.29 (m, 5H), 4.42–4.52 (m, 2H), 4.55–4.71 (m, 3H), 4.95–5.12 (m, 4H), 5.39–5.52 (m, 4H), 5.78 (d, 1H, J=15.9 Hz), 5.89 (s, 1H), 6.00 (dd, 1H, J=15.9, 1.2 Hz), 6.08 (s, 1H), 6.73–6.91 (m, 3H), 7.12–7.37 (m, 20H), 7.98 (d, 1H, J=8.1 Hz); Anal. ($C_{33}H_{44}N_4O_7 \cdot 0.5\ H_2O$) C, H, N.

Example 3

Preparation of Compound 3: Ethyl-3-[CBZ-L-Leu-L-N-Me-(OMe)-Tyr-L-Gln]-E-Propenoate.

Preparation of Intermediate Ethyl-3-[BOC-L-N-Me-(OMe)-Tyr-L-(Tr-Gln)]-E-Propenoate.

Ethyl-3-[BOC-L-(Tr-Gln)]-E-propenoate (0.545 g, 1.00 mmol) was deprotected and coupled with the dicyclohexylamine salt of BOC-L-N-Me-(OMe)-Tyr (0.630 g, 1.28 mmol) using the procedure described in Example 1 for the formation of ethyl-3-[BOC-L-N-Me-Phe-L-(Tr-Gln)]-E-propenoate to provide ethyl-3-[BOC-L-N-Me-(OMe)-Tyr-L-(Tr-Gln)]-E-propenoate (after chromatography, 33% EtOAc in hexanes) as a white foam (0.380 g, 52%): IR (thin film) 3307, 1708, 1672 cm$^{-1}$; $^1$H NMR (CDCl$_3$) δ 1.28 (t, 3H, J=7.2 Hz), 1.38 (s, 9H), 1.60–1.77 (m, 1H), 1.94–207 (m, 1H), 2.27–2.36 (m, 2H), 2.67 (s, 3H), 2.89–2.99 (m, 1H), 3.18–3.27 (m, 1H), 3.78 (s, 3H), 4.18 (q, 2H, J=7.2 Hz), 4.44–4.65 (m, 2H), 5.73 (d, 1H, J=15.6 Hz), 6.35 (d, 1H, J=8.7 Hz), 6.69–6.84 (m, 3H), 6.94 (s, 1H), 7.04–7.12 (m, 2H), 7.17–7.34 (m, 15H); Anal. ($C_{44}H_{51}N_3O_7$) C, H, N.

Preparation of Intermediate Ethyl-3-[CBZ-L-Leu-L-N-Me-(OMe)-Tyr-L-(Tr-Gln)]-E-Propenoate.

Ethyl-3-[BOC-L-N-Me-(OMe)-Tyr-L-(Tr-Gln)]-E-propenoate (0.360 g, 0.491 mmol) was dissolved in 1,4-dioxane (2 mL). A solution of HCl in 1,4-dioxane (4.0 M, 2 mL) was added dropwise. The reaction solution was stirred for 2 h, and then the solvent was evaporated to provide the amine salt as a foam which was used without purification. The crude amine salt was dissolved in dry $CH_2Cl_2$ (12 mL) under argon. 4-Methylmorpholine (0.208 mL, 1.89 mmol), CBZ-L-Leu (0.125 g, 0.471 mmol), hydroxybenzotriazole hydrate (0.096 g, 0.71 mmol), and 1-(3-dimethylaminopropyl)-3-ethylcarbodiimide hydrochloride (0.136 g, 0.709 mmol) were added successively. After stirring overnight, 4-methylmorpholine (0.208 mL, 1.89 mmol), hydroxybenzotriazole hydrate (0.096 g, 0.71 mmol), CBZ-L-Leu (0.125 g, 0.471 mmol), and 1-(3-dimethylaminopropyl)-3-ethylcarbodiimide hydrochloride (0.136 g, 0.709 mmol) were added again. Then 4-dimethylaminopyridine (0.010 g, 0.082 mmol) was added. After stirring 48 h more, the reaction mixture was poured into water (15 mL). The resulting mixture was extracted with $CH_2Cl_2$ (3×75 mL). The combined organic phases were dried over Na2SO$_4$ and evaporated. The residue was purified by chromatography (38% to 50% EtOAc in hexanes) to provide ethyl-3-[CBZ-L-Leu-L-N-Me-(OMe)-Tyr-L-(Tr-Gln)]-E-propenoate (0.210 g, 51%) as a colorless glass: IR (thin film) 3295, 1708, 1660 cm$^{-1}$; $^1$H NMR (CDCl$_3$) (mixture of rotamers) δ 0.65 (d, J=6.5 Hz), 0.68 (d, J=6.8 Hz), 0.82–0.91 (m), 1.14–1.50 (m), 1.52–1.66 (m), 1.68–1.81 (m), 1.87–2.02 (m), 2.16–2.28 (m), 2.89 (s), 2.92 (s), 2.95–3.09 (m), 3.14–3.23 (m), 3.24–3.33 (m), 3.76 (s), 3.76 (s), 4.08–4.25 (m), 4.41–4.49 (m), 4.54–4.63 (m), 4.83–5.16 (m), 5.73 (d, J=15.6 Hz), 5.95 (dd, J=15.7, 1.1 Hz), 6.40 (d, J=8.4 Hz), 6.74 (dd, J=15.6, 5.0 Hz), 6.78–6.87 (m), 6.99–7.06 (m), 7.16–7.34 (m), 7.97 (d, J=7.8 Hz); Anal. ($C_{53}H60N_4O_8 \cdot 0.5\ H_2O$) C, H, N.

Preparation of Product-Ethyl-3-[CBZ-L-Leu-L-N-Me (OMe)-Tyr-L-Gln]-E-Propenoate.

Ethyl-3-[CBZ-L-Leu-L-N-Me-(OMe)-Tyr-L-(Tr-Gln)]-E-propenoate (0.128 g, 0.145 mmol) was deprotected using the procedure described in Example 1 for the formation of ethyl-3-(CBZ-L-N-Me-Phe-L-Gln)-E-propenoate to provide ethyl-3-[CBZ-L-Leu-L-N-Me-(OMe)-Tyr-L-Gln]-E-propenoate (after chromatography, 5% MeOH in $CH_2Cl_2$) as a colorless glass (0.083 g, 89%): IR (thin film) 3401, 3295, 3201, 1708, 1666, 1637 cm$^{-1}$; $^1$H NMR (CDCl$_3$) (mixture of rotamers) δ 0.64–0.71 (m), 0.87–0.94 (m), 1.27 (t, J=7.2 Hz), 1.28 (t, J=7.2 Hz), 1.38–1.51 (m), 1.61–1.85 (m), 1.87–2.02 (m), 2.07–2.21 (m), 2.80–2.92 (m), 2.94 (s), 2.96 (s), 2.97–3.06 (m), 3.08–3.21 (m), 3.36 (dd, J=14.0, 6.2 Hz), 3.76 (s), 4.16–4.28 (m), 4.18 (q, J=7.2 Hz), 4.45–4.66 (m), 4.94–5.12 (m), 5.52 (d, J=7.8 Hz), 5.58 (d, J=7.8 Hz), 5.69 (s), 5.77 (d, J=15.9 Hz), 5.99 (s), 6.00 (dd, J=15.9, 1.2 Hz), 6.21 (s), 6.76 (dd, J=15.9, 5.3 Hz), 6.79–6.91 (m), 7.02–7.10 (m), 7.26–7.37 (m), 7.97 (d, J=8.1 Hz); ($C_{34}H_{46}N_4O_8 \cdot 0.5 H_2O$) C, H, N.

Example 4

Preparation of Compound 5: Ethyl-3-(Cyclopentylthiocarbonyl-L-Leu-L-N-Me-Phe-L-Gln)-E-Propenoate.

Preparation of Cyclopentyl Chlorothiolformate.

Cyclopentanethiol (10.7 mL, 0.1 mol) was dissolved in 200 mL of $CH_2Cl_2$. Triphosgene (11.13 g, 37.5 mmol) was added, and the reaction mixture was cooled to 0° C. $Et_3N$ (14.1 mL, 0.1 mol) was added dropwise, and the reaction was allowed to warm to room temperature over a period of one hour. The solvent was carefully removed under reduced pressure at 20° C. due to the volatility of the product. The resulting residue was taken up in $Et_2O$, and the solids were filtered and washed with more $Et_2O$. The solvent was again carefully removed under reduced pressure, and the product was purified by distillation (85% yield): colorless liquid (bp 70–74° C.; 1 torr): IR(neat) 1756, 830 cm$^{-1}$; $^1$H NMR (benzene-$d_6$) δ 1.01–1.23 (m, 6H), 1.49–1.60 (m, 2H), 3.20–3.29 (m, 1H).

Preparation of Intermediate Cyclopentylthiocarbonyl-L-Leu-OBn.

The p-toluenesulfonic acid salt of L-Leu-OBn (3.14 g, 8.0 mmol) was dissolved in 70 mL of $CH_2Cl_2$, followed by 2.25 mL (16 mmol) of $Et_3N$. Cyclopentyl chlorothiolformate (1.32 g, 8.0 mmol) was dissolved in 10 mL of $CH_2Cl_2$ and added dropwise to the reaction. The reaction was stiffed one hour, and the solvent was removed in vacuo. The product was purified by flash silica gel chromatography eluting with 5% EtOAc/hexanes to give 2.48 g (71%) of a clear oil; IR(KBr) 3318, 2959, 2870, 1744, 1649, 1516, 1186, 854, 746, 696 cm$^{-1}$; $^1$H NMR (DMSO-$d_6$) δ 0.82 (d, 3H, J=6.0 Hz), 0.86 (d, 3H, J=6.0 Hz), 1.39–1.70 (m, 9H), 1.97 (m, 2H), 3.55 (quint, 1H, J=7.0 Hz), 4.23 (m, 1H), 5.09 (d, 1H, J=12.5 Hz), 5.13 (d, 1H, J=12.5 Hz), 7.35 (m, 5H), 8.48 (d, 1H, J=7.7 Hz). Anal. ($C_{19}H_{27}NO_3S$) C, H, N.

Preparation of Intermediate Cyclopentylthiocarbonyl-L-Leu.

Cyclopentylthiocarbonyl-L-Leu-OBn (2.42 g, 6.92 mmol) was dissolved in 35 mL of $CH_2Cl_2$, followed by 4.51 mL (41.5 mmol) of anisole. The reaction was cooled to 0° C., and $AlCl_3$ (2.88 g, 21.6 mmol), dissolved in 35 mL of nitromethane, was added dropwise via pipet. The ice bath was removed, and the reaction was allowed to stir at rt for 5 h. The reaction was diluted with EtOAc and washed with 10% HCl. The organic phase was washed with a sat. $NaHCO_3$ solution. The basic solution was then reacidified to a pH=1 with 10% HCl, and the product was extracted with EtOAc. The organic layer was dried ($MgSO_4$), filtered, and concentrated under reduced pressure to give 0.23 g (93%) of an opaque oil: IR(neat) 3302–2473 (bs), 1715, 1652, 1532, 1202, 925, 852, 673, 563 cm$^{-1}$; $^1$H NMR (DMSO-$d_6$) δ 0.82 (d, 3H, J=6.6 Hz), 0.86 (d, 3H, J=6.6 Hz), 1.40–1.70 (m, 9H), 1.98 (m, 2H), 3.53 (quint, 1H, J=7.0 Hz), 4.18 (m, 1H), 8.29 (d, 1H, J=8.0 Hz), 12.58 (bs). Anal. ($C_{12}H_{21}NO_3S$) C, H, N.

Preparation of Intermediate CBZ-L-(Tr-Gln).

CBZ-L-Gln (28.03 g, 100 mmol) was dissolved in 300 mL of glacial acetic acid. To this solution was added triphenyl-methanol (26.83 g, 100 mmol), acetic anhydride (18.87 mL, 200 mmol), and 0.5 mL of conc. sulfuric acid. The reaction was heated to 55° C. and stirred for one hour. After cooling to room temperature, the mixture was concentrated under reduced pressure to one-third the original volumne. Ice water was added, and the product extracted with EtOAc. The organic layer was washed with water and brine, dried over $MgSO_4$, and concentrated. The crude product was recrystallized from $CH_2Cl_2$/hexane, and the resulting crystals washed with $Et_2O$, yielding 37.27 g (71%) as a white solid: IR (KBr) 3418, 3295, 3059, 3032, 2949, 2515, 1699, 1628, 1539, 1504, 1447, 1418, 1341, 1242, 1209, 1061, 748, 696 cm$^{-1}$; $^1$H NMR(DMSO-$d_6$) δ 1.71 (m, 1 H), 1.88 (m, 1 H), 2.38 (m, 2 H), 3.97 (m, 1 H), 5.04 (s, 2 H), 7.14–7.35 (m, 20H), 7.52 (d, 1 H, J=7.7 Hz), 8.60 (s, 1 H).

Preparation of Intermediate CBZ-L-(Tr-Gln)OMe.

CBZ-L-(Tr-Gln) (0.26 g, 0.5 mmol) was added to a stirring solution of 0.25 mL of acetyl chloride in 5 mL of MeOH, and stirring was continued at room temperature for 1 h. The solvent was removed in vacuo, and the residue dissolved in 100 mL $CH_2Cl_2$. The organic layer was washed with water, saturated $NaHCO_3$, and brine, followed by drying over $Na_2SO_4$. The crude product was purified on a short flash silica gel column, eluting with 20% EtOAc/hexane. The product (0.23 g, 84%) was obtained as a white solid: IR (KBr) 3405, 3277, 3057, 3034, 2953, 1724, 1643, 1532, 1493, 1447, 1207, 1042, 750, 698 cm$^{-1}$; $^1$H NMR (DMSO-$d_6$) δ 1.16 (t, 1 H, J=7.0 Hz), 1.77 (m, 1 H), 1.97 (m, 1H), 3.61 (s, 3H), 4.99 (m, 1H), 5.03 (s, 2H), 7.02–7.55 (m, 20H), 7.69 (d, 1H, J=7.7 Hz), 8.59 (s, 1H). Anal. ($C_{33}H_{32}N_2O_5$) C, H, N.

Preparation of Intermediate CBZ-L-(Tr-Glutaminol).

CBZ-L-(Tr-Gln)OMe (1.50 g, 2.79 mmol) was dissolved in 20 mL of THF and 10 mL of EtOH. LiCl (0.24 g, 5.6 mmol) was added, and the mixture stirred for 10 minutes until all solids had dissolved. $NaBH_4$ (0.21 g, 5.6 mmol) was added, and the reaction was stirred overnight at room temperature. The solvents were removed in vacuo, the residue taken up in water, and the pH was adjusted to 2–3 with 10% HCl. The product was extracted with EtOAc, and the organic layer was washed with water and brine before drying over $MgSO_4$. The crude product was purified on a short flash silica gel column, eluting with an increasing gradient of EtOAc/benzene, yielding 1.02 g (72%) of a white glassy solid: IR (KBr) 3408, 3318, 3057, 3032, 2947, 1699, 1674, 1516, 1447, 1240, 1059, 752, 698 cm$^{-1}$; $^1$H NMR (DMSO-$d_6$) δ 1.40 (m, 1H), 1.72 (m, 1H), 2.26 (m, 2H), 3.17–3.50 (m, 3H), 4.64 (t, 1H, J=5.0 Hz), 5.00 (s, 2H), 7.00–7.40 (m, 20H), 6.96 (d, 1H, J=8.5 Hz), 8.54 (s, 1H). Anal. ($C_{32}H_{32}N_2O_4$) C, H, N.

Preparation of Intermediate L-(Tr-Glutaminol).

10% Pd on carbon (0.03 g) was added to a solution of CBZ-L-(Tr-Glutaminol) (0.51 g, 1.0 mmol) in 20 mL MeOH, with stirring, and under an argon atmosphere. The reaction vessel was evacuated under vacuum and then put under an atmosphere of hydrogen using a balloon. The mixture was stirred for 4 h. At this time the hydrogen gas was evacuated and the catalyst was removed by filtration. The solvent was removed under vacuum to give a white solid in 98% yield which was used without further purification: IR (KBr) 3255, 3057, 3016, 2916, 1642, 1527, 1491, 1446, 1057, 1036, 750, 700, 636 cm$^{-1}$; $^1$H NMR (DMSO-$d_6$) δ 1.29 (m, 1H), 1.53 (m, 1H), 2.29 (m, 2H), 3.08 (m, 1H), 3.18 (m, 2H), 3.38 (bs, 2H), 4.43 (bs, 1H), 7.14–7.28 (m, 15H), 8.62 (s, 1H). Anal. ($C_{24}H_{26}N_2O_2$) C, H, N.

Preparation of Intermediate CBZ-L-N-Me-Phe-L-(Tr-Glutaminol).

CBZ-N-Me-L-Phe (2.24 g, 7.14 mmol) was dissolved in 70 mL of THF. Carbonyldiimidazole (1.16 g, 7.14 mmol) was added, and the reaction was stirred for one hour at rt. L-(Tr-Glutaminol) (2.80 g, 7.5 mmol) was added, and the reaction was stirred overnight. At this time the solvent was removed in vacuo, and the product was purified by column chromatography on silica gel using a gradient solvent system (0–2% MeOH/CHCl$_3$) to give 3.37 g (70%) of a white amorphous solid: IR(KBr) 3304, 3057, 3028, 2949, 1668, 1495, 1447, 1142, 750, 698 cm$^{-1}$; $^1$H NMR (DMSO-d$_6$) δ 1.51 (m, 1H), 1.73 (m, 1H), 2.23 (m, 2H), 2.79 (s, 3H), 2.84 (m, 1H), 3.29 (m, 3H), 3.70 (m, 1H), 4.66 (m, 1H) 4.88 (m, 3H), 7.15–7.28 (m, 25H), 7.69 (m, 1H), 8.55 (m, 1H). MS calcd for C$_{42}$H$_{43}$N$_3$O$_5$+H 670, found 670.

Preparation of Intermediate L-N-Me-Phe-L-(Tr-Glutaminol).

CBZ-L-N-Me-Phe-L-(Tr-glutaminol) (3.33 g, 4.97 mmol) was dissolved in 35 mL of MeOH. The reaction was placed under slight vacuum, and then under an argon atmosphere. With care, 10% Pd/C (0.33 g) was added. The flask was purged of argon which was replaced by hydrogen gas using a balloon. The reaction mixture was stirred at room temperature for 4.5 h, at which time the flask was purged of hydrogen and the catalyst was filtered off. Solvent was removed in vacuo to give 2.36 g (89%) of a white amorphous solid: IR(KBr) 3302, 3057, 3024, 2937, 1655, 1522, 1493, 1447, 750, 700 cm$^{-1}$; $^1$H NMR (DMSO-d$_6$) δ 1.44 (m, 1H), 1.67 (m, 1H), 2.13 (m, 1H), 2.16 (s, 3H), 2.24 (m, 1H), 2.68 (dd, 1H, J=13.5, 7.3 Hz), 2.82 (dd, 1H, J =13.5, 5.8 Hz), 3.10 (m, 2H), 3.25 (m, 1H), 3.67 (m, 1H), 4.63 (t, 1H, J=5.5 Hz), 7.13–7.28 (m, 21H), 7.54 (d, 1H, J=8.8 Hz), 8.54 (s, 1H). Anal. (C$_{34}$H$_{37}$N$_3$O$_3$) C, H, N.

Preparation of Intermediate Cyclopentylthiocarbonyl-L-Leu-L-N-Me-Phe-L-(Tr-Glutaminol).

This preparation was carried out following the procedure of L. A. Carpino, *J. Am. Chem. Soc.* 1993, 115, 4397, the disclosure of which is entirely incorporated herein by reference. Cyclopentylthiocarbonyl-L-Leu (0.27 g, 1.05 mmol) was dissolved in 3.5 mL of DMF. Diisopropylethylamine (0.37 mL, 2.10 mmol) was added, followed by 0.56 g (1.05 mmol) of L-N-Me-Phe-L-(Tr-glutaminol). The reaction was cooled to 0° C. and O-(7-azabenzotriazol-1-yl)-1,1,3,3-tetramethyluronium hexafluorophosphate (HATU) (0.398 g, 1.05 mmol) was added. The reaction mixture was allowed to warm to room temperature whereupon the DMF was removed in vacuo. The residue was dissolved with EtOAc, and the organic phase washed consecutively with 10% HCl solution, saturated NaHCO$_3$ solution, H$_2$O, and brine. The solvent was dried (MgSO$_4$), filtered, and concentrated to give a residue which was subjected to flash column chromatography on silica gel (gradient; 0–1% MeOH/CHCl$_3$) to give 0.49 g (60%) of a white amorphous solid: IR(KBr) 3293, 3057, 3024, 2955, 2868, 1634, 1493, 1447, 1205, 752, 700 cm$^{-1}$; $^1$H NMR (DMSO-d$_6$) (mixture of rotamers) δ −0.18 (m), 0.62 (m), 0.79 (d, J=6.3 Hz), 1.00–2.05 (m), 2.08–2.40 (m), 2.81 (s), 2.88 (m), 2.95 (s), 3.05–3.53 (m), 3.65 (m), 3.79 (m), 4.27 (m), 4.61 (m), 5.11 (m), 7.14–7.28 (m), 7.43 (d, J=8.0 Hz), 7.64 (d, J=8.8 Hz), 8.17 (d, J=8.0 Hz), 8.43 (d, J=7.0 Hz), 8.51 (s). MS calcd for C$_{46}$H$_{56}$N$_4$O$_5$S+Cs 909, found 909.

Preparation of Intermediate Cyclopentylthiocarbonyl-L-Leu-L-N-Me-Phe-L-(Tr-Glutaminal).

To cyclopentylthiocarbonyl-L-Leu-L-N-Me-Phe-L-(Tr-glutaminol) (0.57 g, 0.73 mmol) dissolved in 7 mL of DMSO was added o-iodoxybenzoic acid (0.61 g, 2.19 mmol). The reaction mixture was stirred at rt for 1.5 h. The DMSO was then removed under reduced pressure, and the residue was diluted with CH$_2$Cl$_2$ and reconcentrated to remove any residual DMSO. Dilution with CH$_2$Cl$_2$ and reconcentration was repeated, and the residue was diluted with EtOAc to give a white precipitate which was filtered off. The solvent was washed with a 5% Na$_2$S$_2$O$_3$/5% NaHCO$_3$ solution, water, and brine before drying over MgSO$_4$. Removal of the solvent under vacuum gave 0.41 g (72%) of a white glassy solid which was used immediately without further purification: $^1$H NMR (DMSO-d$_6$) (mixture of rotamers) δ −0.03 (m), 0.62 (m), 1.04–2.10 (m), 2.20–2.45 (m), 2.82 (s), 2.90 (m), 2.94 (s), 3.21 (m), 4.00 (m), 4.14 (m), 4.34 (m), 4.62 (m), 4.81 (m), 5.17 (m), 7.14–7.28 (m), 8.15 (d, J=7.0 Hz), 8.25 (d, J=7.0 Hz), 8.35 (d, J=7.0 Hz), 8.41 (d, J=7.0 Hz), 8.57 (s), 8.62 (s), 9.27 (s), 9.43 (s).

Preparation of Intermediate Ethyl-3-[Cyclopentylthiocarbonyl-L-Leu-L-N-Me-Phe-L-(Tr-Gln)]-E-Propenoate.

Cyclopentylthiocarbonyl-L-Leu-N-Me-L-Phe-L-(Tr-glutaminal) (0.19 g, 0.25 mmol) was dissolved in 5 mL of THF. (Carbethoxymethylene)triphenylphosphorane (0.10 g, 0.30 mmol) was added, and the reaction was stirred overnight at rt. The solvent was removed in vacuo, and the residue purified by flash column chromatography on silica gel (gradient; 0–0.75 % MeOH/CHCl$_3$) to give 0.25 g of material that was contaminated by triphenylphosphine oxide. This material was used without further purification: $^1$H NMR (DMSO-d$_6$) (mixture of rotamers) δ −0.16 (m), 0.62 (m), 0.79 (d, J=6.3 Hz), 1.10 (m), 1.20 (t, J=7.0 Hz), 1.30–1.78 (m), 1.95 (m), 2.10–2.42 (m), 2.80 (s), 2.88 (m), 2.95 (s), 3.16 (m), 3.48 (m), 4.10 (q, J=7.0 Hz), 4.11 (q, J=7.0 Hz), 4.37 (m), 4.53 (m), 4.63 (m), 4.81 (m), 5.06 (m), 5.66 (d, J=16.0 Hz), 5.93 (d, J=16.0 Hz), 6.71 (dd, J=16.0, 6.0 Hz), 6.80 (d, J=16.0, 6.0 Hz), 7.13–7.28 (m), 7.97 (d, J=8.0 Hz), 8.07 (d, J=8.0 Hz), 8.16 (d, J=7.0 Hz), 8.49 (d, J=6.0 Hz), 8.55 (s), 8.60 (s).

Preparation of Product Ethyl-3-(Cyclopentylthiocarbonyl-L-Leu-L-N-Me-Phe-L-Gln)-E-Propenoate.

Ethyl-3-[cyclopentylthiocarbonyl-L-Leu-L-N-Me-Phe-L-(Tr-Gln)]-E-propenoate (0.25 g) was dissolved in 5 mL of CH$_2$Cl$_2$. Trifluoroacetic acid (0.5 mL) was added, and the reaction was stirred at rt for 4 h. The solvent was removed in vacuo, and the residue purified by flash column chromatography on silica gel (gradient; 0–2 % MeOH/CHCl$_3$) to give 0.11 g (74% for two steps from the aldehyde intermediate) as a white amorphous solid: mp=68–72° C.; IR(KBr) 3283, 2955, 1634, 1531, 1277, 1205 cm$^{-1}$; $^1$H NMR (DMSO-d$_6$) (mixture of rotamers) δ −0.26 (m), 0.61 (m), 0.82 (d, J=6.3 Hz), 0.83 (d, J=6.3 Hz), 1.13 (m), 1.20 (t,J=7.0 Hz), 1.30–2.12 (m), 2.77 (s), 2.90 (m), 2.94 (s), 3.11 (m), 3.47 (m), 4.10 (q, J=7.0 Hz), 4.11 (q, J=7.0 Hz), 4.38 (m), 4.50 (m), 4.67 (m), 4.81 (m), 5.04 (m), 5.69 (d, J=15.0 Hz), 5.99 (d, J=15.0 Hz), 6.72 (dd, J=15.0, 5.5 Hz), 6.76 (bs), 6.83 (d, J=15.0, 5.5 Hz), 7.12–7.30 (m), 7.99 (d, J=8.0 Hz), 8.04 (d, J=8.0 Hz), 8.19 (d, J=8.0 Hz), 8.52 (d, J=6.0 Hz). HRMS calcd for C$_{31}$H$_{46}$N$_4$O$_6$S+Cs 735.2192, found 735.2174. Anal. (C$_{31}$H$_{46}$N$_4$O$_6$S) C, H, N.

Example 5

Preparation of Compound 6: 2-(Cyclopentylthiocarbonyl-L-Leu-L-N-Me-Phe-L-Gln)-E(α-Vinyl-γ-Butyrolactone).

Preparation of Intermediate 2-[Cyclopentylthiocarbonyl-L-Leu-L-N-Me-Phe-L-L-(Tr-Gln)]-E-(α-Vinyl-γ-Butyrolactone).

Using the procedure described in Example 4 for the preparation of ethyl-3-[cyclopentylthiocarbonyl-L-Leu-L-N-Me-Phe-L-(Tr-Gln)]-E-propenoate, this intermediate was synthesized from cyclopentylthiocarbonyl-L-Leu-L-N-Me-L-Phe-L-(Tr-glutaminal) (0.205 g, 0.264 mmol) and α-(triphenylphosphoranylidene)-γ-butyrolactone (0.12 g, 0.343 mmol) (prepared from α-bromo-γ-butyrolactone according to the procedure of J. E. Baldwin, et al., *Tetrahedron*; 1992, 48, 9373, the disclosure of which is entirely incorporated herein by reference) in 5 mL THF to give 0.28 g of product contaminated with triphenylphosphine oxide which was used without further purification: $^1$H NMR (DMSO-d$_6$) (mixture of rotamers) δ −0.12 (m), 0.60 (m), 0.79 (d, J=6.3 Hz), 1.10–2.18 (m), 2.10–2.49 (m), 2.80 (s), 2.89 (m), 2.94 (s), 3.09–3.57 (m), 4.30 (m), 4.42 (m), 4.85 (m), 5.01 (m), 6.26 (m), 6.42 (m), 7.10–7.29 (m), 8.01 (d, J=8.0 Hz), 8.06 (d, J=8.0 Hz), 8.18 (d, J=7.0 Hz), 8.48 (d, J=7.0 Hz), 8.53 (s), 8.59 (s).

Preparation of Product-2-(Cyclopentylthiocarbonyl-L-Leu-L-N-Me-Phe-L-Gln)-E-(α-Vinyl-γ-Butyrolactone).

Using the procedure described in Example 4 for the preparation of ethyl-3-(cyclopentylthiocarbonyl-L-Leu-L-N-Me-Phe-L-Gln)-E-propenoate, 2-(cyclopentylthiocarbonyl-L-Leu-L-N-Me-Phe-L-Gln)-E-(α-vinyl-γ-butyrolactone) was synthesized from 2-[cyclopentylthiocarbonyl-L-Leu-L-N-Me-Phe-L-Tr-Gln)]-E-(α-vinyl-γ-butyrolactone) in 49% yield (two steps from the aldehyde): white amorphous solid: mp=87–91° C.: IR(KBr) 3286, 2963, 1749, 1668, 1634, 1531, 1452, 1205, 1138 cm$^{-1}$; $^1$H NMR (DMSO-d$_6$) (mixture of rotamers) δ −0.12 (m), 0.58 (m), 0.83 (m), 1.08 (m), 1.20–1.79 (m), 2.01 (m), 2.77 (s), 2.84 (m), 2.94 (s), 3.12 (m), 3.53 (m), 4.26–4.43 (m), 4.68 (m), 4.96 (m), 6.26 (m), 6.39 (m), 6.76 (bs), 7.12–7.27 (m), 8.04 (m), 8.19 (d, J=8.0 Hz), 8.50 (d, J=7.0 Hz). HRMS calcd for $C_{31}H_{44}N_4O_6S$+Cs 733.2036, found 733.2053. Anal. ($C_{31}H_{44}N_4O_6S$·0.75 CHCl$_3$) C, H, N.

Example 6

Preparation of Compound 7: 1-(2',3'-Dihydroindolin-1-yl)-3-(Ethylthiocarbonyl-L-Leu-L-N-Me-Phe-L-Gln)-E-Propenone.

Preparation of Intermediate BOC-L-Leu-L-N-Me-Phe-OMe.

N-Me-Phe-OMe.HCl (1.4 g) was dissolved in CH$_2$Cl$_2$ (50 mL) and poured into a combination of 1 N NaOH (aq, 7 mL) and sat. NaHCO$_3$ (25 mL). After mixing, the organic phase was separated, and the aqueous phase was washed with CH$_2$Cl$_2$ (3×50 mL). The combined organic phases were dried over Na$_2$SO$_4$ and evaporated to give the free amine as a clear colorless oil (1.14 g, 5.90 mmol). A solution of this amine and diisopropylethylamine (1.13 mL, 6.49 mmol) in DMF (10 mL) was added dropwise to a 0° C. solution of BOC-L-Leu (1.50 g, 6.49 mmol) and hydroxybenzotriazole hydrate (0.877 g, 6.49 mmol) in DMF (10 mL). Dicyclohexylcarbodiimide (1.47 g, 7.12 mmol) was added. The reaction mixture was stirred at 0° C. for 1 h, and was then stirred at rt for 48 h. The mixture was filtered to remove the precipitate, and the filtrate was evaporated. The residue was dissolved in CH$_2$Cl$_2$ (200 mL), washed with sat. NaHCO$_3$ (40 mL), dried over Na$_2$SO$_4$, and evaporated. The residue was purified by chromatography (25% EtOAc in hexanes) to give BOC-L-Leu-L-N-Me-Phe-OMe as a white solid (2.04 g, 85%): mp=126–127° C.; IR (thin film) 3401, 3319, 1743, 1708, 1649 cm$^{-1}$; $^1$H NMR (CDCl$_3$) (major rotamer) δ 0.92 (d, 3H, J=6.8 Hz), 0.95 (d, 3H, J=6.5 Hz), 1.32–1.48 (m, 2H), 1.41 (s, 9H), 1.61–1.77 (m, 1H), 2.90 (s, 3H), 3.04 (dd, 1H, J=14.5, 10.5 Hz), 3.37 (dd, 1H, J=14.5, 5.5 Hz), 3.72 (s, 3H), 4.48–4.57 (m, 1H), 4.98–5.04 (m, 1H), 5.20 (dd, 1H, J=10.5, 5.5 Hz), 7.16–7.32 (m 5H); Anal. ($C_{22}H_{34}N_2O_5$) C, H, N.

Preparation of Intermediate BOC-L-Leu-L-N-Me-Phe.

BOC-L-Leu-L-N-Me-Phe-OMe (0.625 g, 1.54 mmol) was dissolved in MeOH (20 mL) and cooled to 0° C. A solution of 2 N NaOH (aq, 6.15 mL, 12.3 mmol) was added dropwise. The reaction mixture was stirred for 3 h at rt and poured into 10% aq KHSO$_4$ (150 mL). This mixture was extracted with CH$_2$Cl$_2$ (3×100 mL), and the combined organic phases were dried over Na$_2$SO$_4$ and evaporated to give BOC-L-Leu-L-N-Me-Phe as a white foam (0.617 g, quantitative yield) which was used without purification.

Preparation of Intermediate [2-(2,3-Dihydroindol-1-yl)-2-oxo-ethyl]-Phosphonic Acid Diethyl Ester.

Oxalyl chloride (5.96 mL, 68.3 mmol) was added to a solution of diethylphosphonoacetic acid (12.8 g, 65.0 mmol) and DMF (0.03 mL, 0.39 mmol) in benzene (150 mL) at 23° C. The reaction mixture was stirred at 23° C. for 1 h and then was concentrated under reduced pressure. The resulting oil was dissolved in THF (30 mL) and was added via cannula to a solution of indoline (7.38 g, 61.9 mmol) and triethylamine (10.9 mL, 78.0 mmol) in THF (200 mL) at 0° C. The reaction mixture was stirred at 0° C. for 15 min, and then it was partitioned between 0.5 M HCl (150 mL) and EtOAc (2×150 mL). The combined organic layers were dried over Na$_2$SO$_4$ and concentrated to afford a tan solid. Recrystallization from Et$_2$O provided [2-(2,3-dihydroindol-1-yl)-2-oxo-ethyl]-phosphonic acid diethyl ester (12.2 g, 63%) as a light brown solid: mp=97–99° C.; IR (KBr) 3460, 1657, 1597, 1482 cm$^{-1}$; $^1$H NMR (CDCl$_3$) δ 1.35 (t, 6H, J=7.2), 3.14 (d, 2H, J=22.4), 3.22 (d, 2H, J=8.4), 4.15–4.30 (m, 6H), 7.04 (t, 1H, J=7.0), 7.17–7.82 (m, 2H), 8.21 (d, 1H, J=9.0); Anal. ($C_{14}H_{20}NO_4P$) C, H, N.

Preparation of Intermediate 1-(2',3'-Dihydroindolin-1-yl)-3-[BOC-L-(Tr-Gln)]-E-Propenone.

Sodium bis(trimethylsilyl)amide (11.9 mL of a 1.0 M solution in THF, 11.9 mmol, 1.0 equiv) was added to a solution of [2-(2,3-dihydroindol-1-yl)-2-oxo-ethyl]-phosphonic acid diethyl ester (3.54 g, 11.9 mmol, 1.0 equiv) in THF (150 mL) at −78° C., and the resulting solution was stirred for 20 min at that temperature. Crude BOC-L-(Tr-Glutaminal) (5.63 g, 11.9 mmol, 1 equiv) in THF (40 mL) was added via cannula, and the reaction mixture was stirred for 1 h at −78° C., warmed to 0° C. for 10 min, and partitioned between 0.5 M HCl (150 mL) and EtOAc (2×150 mL). The organic layers were dried over Na$_2$SO$_4$ and concentrated. Purification of the residue by flash column chromatography (50% EtOAc in hexanes) provided 1-(2',3'-dihydroindolin-1-yl)-3-[BOC-L-(Tr-Gln)]-E-propenone as an off-white foam: IR (thin film) 3401, 3307, 1690, 1665 cm$^{-1}$; $^1$H NMR (CDCl$_3$) δ 1.44 (s, 9H), 1.76–2.05 (m, 2H), 2.37–4.06 (m, 2H), 3.11–3.22 (m, 2H), 4.02–4.16 (m, 2H), 4.27–4.40 (m, 1H), 4.91–4.97 (m, 1H), 6.29 (d, 1H, J=14.9), 6.77–6.96 (m, 2H), 6.98–7.05 (m, 1H), (m, 17H), 8.25 (d, 1H, J=7.5); Anal. ($C_{39}H_{41}N_3O_4$) C, H, N.

Preparation of Intermediate 1-(2',3'-Dihydroindolin-1-yl)-3-[BOC-L-Leu-L-N-Me-Phe-L-(Tr-Gln)]-E-Propenone.

1-(2',3'-Dihydroindolin-1-yl)-3-[BOC-L-(Tr-Gln)]-E-propenone (0.420 g, 0.682 mmol) was dissolved in 1,4-dioxane (3 mL). A solution of HCl in 1,4-dioxane (4.0 M, 3 mL) was added dropwise. After stirring for 2 h, the solvent was evaporated to give the amine salt which was used without purification. This crude amine salt was coupled to BOC-L-Leu-L-N-Me-Phe (0.302 g, 0.769 mmol) using the procedure described in Example 6 for the formation of BOC-L-Leu-L-N-Me-Phe-OMe to give 1-(2',3'-Dihydroindolin-1-yl)-3-[BOC-L-Leu-L-N-Me-Phe-L-(Tr-Gln)]-E-propenone (after chromatography, 43% EtOAc in hexanes to 100% EtOAc) as an off-white foam (0.323 g, 53%): IR (thin film) 3401, 3295, 1660 cm$^{-1}$; $^1$H NMR (CDCl$_3$) (mixture of isomers) δ 0.65 (d, J=6.5 Hz), 0.85 (d, J=6.8 Hz), 0.88 (d, J=6.5 Hz), 1.04–1.21 (m), 1.23–1.48 (m), 1.34 (s), 1.41 (s), 1.56–1.67 (m), 1.82–1.94 (m), 1.95–2.09 (m), 2.26–2.36 (m), 2.90 (s), 2.99 (dd, J=14.3, 10.4 Hz), 3.13–3.22 (m), 3.30 (dd, J=14.3, 3.6 Hz), 3.97–4.18 (m), 4.38–4.47 (m), 4.55–4.77 (m), 4.83–4.90 (m), 6.18 (d, J=14.0 Hz), 6.35–6.46 (m), 6.72 (s), 6.82–6.91 (m), 6.99–7.35 (m), 8.17 (d, J=8.4 Hz), 8.25 (d, J=8.1 Hz); Anal. (C$_{55}$H$_{63}$N$_5$O$_6$.0.75 H$_2$O) C, H, N.

Preparation of Intermediate 1-(2',3'-Dihydroindolin-1-yl)-3-[Ethylthiocarbonyl-L-Leu-L-N-Me-Phe-L-(Tr-Gln)]-E-Propenone.

1-(2',3'-Dihydroindolin-1-yl)-3-[BOC-L-Leu-L-N-Me-Phe-L-(Tr-Gln)]-E-propenone (0.315 g, 0.355 mmol) was dissolved in 1,4-dioxane (6 mL). A solution of HCl in 1,4-dioxane (4.0 M, 4 mL) was added dropwise. After stirring for 2 h, the solvent was evaporated to give the amine salt which was used without purification. This crude amine salt was dissolved in dry CH$_2$Cl$_2$ (8 mL) under argon, and diisopropylethylamine (0.136 mL, 0.781 mmol) was added. Ethyl chlorothiolformate (0.044 mL, 0.422 mmol) was added. The reaction solution was stirred 2 h and then poured into water (15 mL). The resulting mixture was extracted with CH$_2$Cl$_2$ (3×50 mL). The combined organic phases were dried over Na$_2$SO$_4$ and evaporated. The residue was purified by chromatography (50%–67% EtOAc in hexanes) to give 1-(2',3'-Dihydroindolin-1-yl)-3-[Ethylthiocarbonyl-L-Leu-L-N-Me-Phe-L-(Tr-Gln)]-E-Propenone as a white foam (0.127 g, 41%): IR (thin film) 3284, 1660, 1637, 1596 cmf$^{-1}$; $^1$H NMR (CDCl$_3$) (mixture of isomers) δ 0.59–0.76 (m), 0.82–0.89 (m), 1.15 (t, J=7.3 Hz), 1.24 (t, J=7.3 Hz). 1.32–1.44 (m), 1.52–1.76 (m), 1.83–2.11 (m), 2.04 (s), 2.25–2.36 (m), 2.63–3.41 (m), 2.88 (s), 2.89 (s), 3.94–4.19 (m), 4.34–4.44 (m), 4.50–4.72 (m), 5.82 (d, J=7.5 Hz), 5.92 (d, J=7.5 Hz), 6.22 (d, J=14.6 Hz), 6.38 (d, J=15.0 Hz), 6.65 (d, J=8.4 Hz), 6.72–6.95 (m), 6.99–7.06 (m), 7.08–7.34 (m), 8.03 (d, J=7.8 Hz), 8.22–8.28 (m); Anal. (C$_{53}$H$_{59}$N$_5$O$_5$S) C, H, N.

Preparation of Product 1-(2',3'-Dihydroindolin-1-yl)-3-(Ethylthiocarbonyl-L-Leu-L-N-Me-Phe-L-Gln)-E-Propenone.

1-(2',3'-Dihydroindolin-1-yl)-3-[ethylthiocarbonyl-L-Leu-L-N-Me-Phe-L-(Tr-Gln)]-E-propenone (0.110 g, 0.125 mmol) was deprotected using the procedure described in Example 1 for the formation of ethyl-3-(CBZ-L-N-Me-Phe-L-Gln)-E-propenoate to give 1-(2',3'-dihydroindolin-1-yl)-3-(ethylthiocarbonyl-L-Leu-L-N-Me-Phe-L-Gln)-E-propenone (after chromatography, 8% MeOH in CH$_2$Cl$_2$, and evaporation from Et2O) as a white waxy material (0.044 g, 55%): IR (thin film) 3389, 3284, 3213, 1660, 1631 cm$^{-1}$; $^1$H NMR (CDCl$_3$) (mixture of isomers) δ 0.61–0.78 (m), 0.91 (d, J=6.5 Hz), 0.92 (d, J=6.2 Hz), 1.18–1.34 (m), 1.39–1.57 (m), 1.58–1.85 (m), 1.87–2.11 (m), 2.15–2.33 (m), 2.72–3.31 (m), 2.96 (s), 3.41–3.50 (m), 4.03–4.20 (m), 4.42–4.77 (m), 5.78 (d, J=12.4 Hz), 6.01 (s, bs), 6.26–6.49 (m), 6.57 (d, J=7.2 Hz), 6.80–6.97 (m), 6.99–7.35 (m), 7.91 (d, J=8.1 Hz), 8.22–8.30 (m); Anal. (C$_{34}$H$_{45}$N$_5$O$_5$S) C, H, N.

Example 7

Preparation of Compound 8: 2-(Ethylthiocarbonyl-L-Leu-L-N-Me-Phe-L-Gln)-E-(α-Vinyl-γ-Butyrolactone).

Preparation of Intermediate 2-[BOC-L-(Tr-Gln)]-E-(α-Vinyl-γ-Butyrolactone).

BOC-L-(Tr-glutaminal) (290 mg, 0.614 mmol) and α-(triphenylphosphoranylidene)-γ-butyrolactone (255 mg, 0.737 mmol) (prepared from α-bromo-γ-butyrolactone according to the procedure of J. E. Baldwin, et al., *Tetrahedron*; 1992, 48, 9373, the disclosure of which is entirely incorporated herein by reference) were refluxed in DME (15 mL)/DMF (2 mL) for 2 h. Solvents were removed under vacuum, and the residue was purified by flash chromatography eluting with 50% EtOAc/hexane on silica gel to give 235 mg of 2-[BOC-L-(Tr-Gln)]-E-(α-vinyl-γ-butyrolactone) as a white solid in 71% yield: IR (KBr) 3399, 3059, 2976, 2926, 1752, 1688, 1493, 1366, 1248, 1169 cm$^{-1}$; $^1$H NMR (CDCl$_3$) δ 1.41 (s, 9 H), 1.84 (m, 2 H), 2.38 (q, 2 H, J=6.4 Hz) 2.80 (m, 1 H), 2.97 (m, 1 H), 4.22 (m, 1 H), 4.33 (t, 2 H, J=7.2 Hz), 4.81 (m, 1 H), 6.43 (m, 1 H), 6.80 (s, 1 H), 7.19–7.32 (m, 15 H). Anal. (C$_{33}$H$_{36}$N$_2$O$_5$.H$_2$O) C, H, N.

Preparation of Intermediate 2-[BOC-L-Leu-L-N-Me-Phe-L-(Tr-Gln)]-E-(α-Vinyl-γ-Butyrolactone).

2-[BOC-L-(Tr-Gln)]-E-(α-vinyl-γ-butyrolactone) (0.577 g, 1.03 mmol) was dissolved in 1,4-dioxane (3 mL). A solution of HCl in 1,4-dioxane (4.0 M, 3 mL) was added dropwise. The solution was stirred at rt for 2 h, at which time the solvent was evaporated to provide the amine HCl salt which was used without purification. The crude salt and BOC-L-Leu-L-N-Me-Phe (0.288 g, 1.03 mmol) were dissolved in dry CH$_2$Cl$_2$ (15 mL). Hydroxybenzotriazole-hydrate (0.209 g, 1.55 mmol), 4-methylmorpholine (0.34 mL, 3.09 mmol), and 1-(3-dimethylaminopropyl)-3-ethylcarbarbodiimide hydrochloride (0.296 g, 1.55 mmol) were added successively. The reaction mixture was stirred at rt overnight and poured into water (50 mL). The resulting mixture was extracted with CH$_2$Cl$_2$ (2×50 mL). The combined organic layers were dried over Na$_2$SO$_4$, concentrated, and purified by flash column chromatography (2% MeOH in CH$_2$Cl$_2$) to afford 2-[BOC-L-Leu-L-N-Me-Phe-L-(Tr-Gln)]-E-(α-vinyl-γ-butyrolactone) (0.691 g, 82%/O) as white foam: IR (thin film) 3301, 2958, 1753, 1675, 1494, 1173, 728 cm$^{-1}$; $^1$H NMR (mixture of rotamers) (CDCl$_3$) δ 0.63–0.66 (m), 0.71–0.75 (m), 1.03–1.13 (m), 1.37 (s), 1.38 (s), 1.41 (s), 1.42 (s), 1.81–2.00 (m), 2.26–2.29 (m), 2.73–3.06 (m), 3.27 (d, J=3.3 Hz), 3.32 (d, J=3.3 Hz), 3.60–3.68 (m), 4.27–4.38 (m), 4.87 (d, J=7.2 Hz), 6.50 (d, J=3.3 Hz), 6.53 (t, J=3.3 Hz), 6.70 (s), 7.09–7.13 (m), 7.19–7.34 (m), 7.44–7.50 (m), 7.64–7.71 (m), 8.21 (d, J=3.6 Hz). Anal. (C$_{49}$H$_{58}$N$_4$O$_7$.0.45 H$_2$O) C, H, N.

Preparation of Intermediate 2-[Ethylthiocarbonyl-L-Leu-L-N-Me-Phe-L-(Tr-Gln)]-E-(α-Vinyl-γ-Butyrolactone).

2-[BOC-L-Leu-L-N-Me-Phe-L-(Tr-Gln)]-E-(α-vinyl-γ-butyrolactone) (0.652 g, 0.8 mmol) was dissolved in 1,4-dioxane (3 mL). A solution of HCl in 1,4-dioxane (4.0 M, 3 mL) was added dropwise. The solution was stirred at rt for 2 h, and the solvent was evaporated to provide the amine HCl salt which was used without purification. The crude amine HCl salt was dissolved in dry CH$_2$Cl$_2$ (10 mL), and Et$_3$N (0.335 mL, 2.4 mmol) was added. The reaction mixture was cooled to 0° C., and ethyl chlorothiolformate (0.083 mL, 0.8 mmol) was added. The reaction mixture was stirred at 0° C. for 2 h and then poured into H$_2$O(25 mL) and extracted with CH$_2$Cl$_2$ (3×25 mL). The combined organic layers were dried over Na$_2$SO$_4$, concentrated, and purified by flash column chromatography (2% MeOH in CH$_2$Cl$_2$) to afford 2-[ethylthiocarbonyl-L-Leu-L-N-Me-Phe-L-(Tr-Gln)]-E-(α-vinyl-γ-butyrolactone) as a white foam (0.389 g, 60%): IR (thin film) 3294, 2361, 1752, 1636, 1522, 1206 cm$^{-1}$; $^1$H NMR (mixture of rotamers) (CDCl$_3$): δ 0.62–0.68 (m), 0.87 (d, 6.6 Hz), 1.19–1.29 (m), 1.37–1.42 (m), 1.89–1.94 (m), 2.28–2.31 (m), 2.71–3.12 (m), 3.65–3.78 (m), 4.31–4.34 (m), 4.55–4.58 (m), 5.66 (d, J=6.3 Hz), 5.72 (d, J=7.5 Hz), 6.40–6.43 (m), 6.51 (t, J=3.0 Hz), 5.54 (t, J=3.0 Hz), 6.75 (s), 7.09–7.12 (m), 7.21–7.34 (m), 7.44–7.50

(m), 7.53–7.58 (m), 7.64–7.71 (m), 8.06 (d, J=7.5 Hz). Anal. ($C_{47}H_{54}N_4O_6S$) C, H, N.

Preparation of Product 2-(Ethylthiocarbonyl-L-Leu-L-N-Me-Phe-L-Gln)-E-(α-Vinyl-γ-Butyrolactone).

2-[Ethylthiocarbonyl-L-Leu-L-N-Me-Phe-L-(Tr-Gln)]-E-(α-vinyl-γ-butyrolactone) (202 mg, 0.25 mmol) was dissolved in 5 mL of dry $CH_2Cl_2$. Trifluoroacetic acid (4 mL) and triisopropylsilane (2 drops) were added sequentially to give a bright yellow solution. After stirring for 20 min, no yellow color remained. The reaction mixture was concentrated, and the residue was purified by flash column chromatography (2% MeOH in $CH_2Cl_2$) to afford 2-(ethylthiocarbonyl-L-Leu-L-N-Me-Phe-L-Gln)-E-(α-vinyl-γ-butyrolactone) as a white solid (0.62 g, 42%): IR (thin film) 3239, 1638, 1526, 1209 cm$^{-1}$; $^1$H NMR (mixture of rotamers) (DMSO-$d_6$) δ 0.57–0.65 (m), 0.82–0.85 (m), 1.11–1.17(m), 1.35–1.50 (m), 1.68–1.80 (m), 1.98–2.06 (m), 2.71–2.97 (m), 3.10–3.17 (m), 4.26–4.46 (m), 4.69–4.71 (m), 5.00 (t, J=7.5 Hz), 5.75 (s), 6.25–6.28 (m), 6.38–6.41 (m), 6.77 (s), 7.16–7.27 (m), 7.94 (d, J=8.1 Hz), 8.03 (d, J=7.5 Hz), 8.26 (d, J=7.5 Hz), 8.54 (d, 6.9 Hz). Anal. ($C_{28}H_{40}N_4O_6S.0.75\ H_2O$) C, H, N. HRMS calcd for $C_{28}H_{40}N_4O_6S$+Cs 693.1723, found 693.1739.

Example 8

Preparation of Compound 9: Ethyl-3-(Benzylthiocarbonyl-L-hPhe-L-N-Me-Phe-L-Gln)-E-Propenoate.

Preparation of Intermediate CBZ-L-hPhe-L-N-Me-Phe-L-(Tr-Glutaminol).

Using the procedure described in Example 4 for the preparation of cyclopentylthiocarbonyl-L-Leu-L-N-Me-L-Phe-L-(Tr-glutaminol), CBZ-L-hPhe-L-N-Me-Phe-L-(Tr-Glutaminol) was synthesized from CBZ-L-hPhe and L-N-Me-Phe-L-(Tr-Glutaminol) in 71% yield: white amorphous solid: IR(KBr) 3295, 3061, 3027, 2936, 1659, 1495, 1447, 1261, 1043, 750, 698 cm$^{-1}$; $^1$H NMR (DMSO-$d_6$) (mixture of rotamers) δ 0.51 (m), 1.47 (m), 1.77 (m), 2.10–2.70 (m), 2.78 (s), 2.85 (s), 2.89 (m), 3.20 (m), 3.78 (m), 3.83 (m), 4.22 (m), 4.60–5.10 (m), 7.03–7.36 (m), 7.48 (m), 7.72 (d, J=9.0 Hz), 7.84 (d, J=7.0 Hz), 8.49 (s), 8.51 (s). Anal. ($C_{52}H_{54}N_4O_6$) C, H, N.

Preparation of Intermediate L-hPhe-L-N-Me-Phe-L-(Tr-Glutaminol).

Using the procedure described in Example 4 for the preparation of L-N-Me-Phe-L-(Tr-glutaminol), L-hPhe-L-N-Me-Phe-L-(Tr-Glutaminol) was synthesized from CBZ-L-hPhe-L-N-Me-Phe-L-(Tr-Glutaminol) in 96% yield: white amorphous solid: IR(KBr) 3331, 3057, 3029, 2936, 1657, 1493, 1449, 752, 700 cm$^{-1}$; $^1$H NMR (DMSO-$d_6$) δ (mixture of rotamers) 1.38–1.60 (m), 1.73 (m), 2.05–2.40 (m), 2.58 (m), 2.70 (s), 2.78 (s), 2.90 (m), 3.10–3.33 (m), 3.51(m), 3.72 (m), 4.63 (m), 4.74 (m), 4.95 (m), 7.02–7.28 (m), 7.51 (d, J=8.0 Hz), 8.50 (m), 8.55 (s). Anal. ($C_{44}H_{48}N_4O_4$) C, H, N.

Preparation of Intermediate Benzyl chlorothioformate.

Using the procedure described in Example 4 for the preparation of cyclopentyl chlorothiolformate, benzyl chlorothiolformate was synthesized from benzylmercaptan in 71% yield: colorless liquid (bp 95–100° C.; 8 torr): IR(neat) 1755 cm$^{-1}$; $^1$H NMR (CDCl$_3$) δ 4.19 (s, 2H), 7.30–7.34 (m, 5H). This compound is reported in the literature, for example, in J. J Willard et al., *J. Am. Chem. Soc.* 1960, 82, 4347, the disclosure of which is entirely incorporated herein by reference.

Preparation of Intermediate Benzylthiocarbonyl-L-hPhe-L-N-Me-Phe-L-(Tr-Glutaminol).

L-hPhe-L-N-Me-Phe-L-(Tr-Glutaminol) (0.62 g, 0.88 mmol) was dissolved in 7 mL of $CH_2Cl_2$. Benzyl chlorothiolformate (0.134 mL, 0.88 mmol) dissolved in 2 mL of $CH_2Cl_2$ was added dropwise followed by 0.13 mL (0.90 mmol) of Et$_3$N. The reaction mixture was stirred for 15 minutes at rt, and the solvent was removed in vacuo. The residue was purified by flash column chromatography on silica gel (gradient: 0–1.5% MeOH/CHCl$_3$) to give 0.70 g (94%) of a white amorphous solid: IR(KBr) 3287, 3061, 3026, 2936, 1641, 1495, 1449, 1213, 750, 698 cm$^{-1}$; $^1$H NMR (DMSO-$d_6$) (mixture of rotamers) δ 0.56 (m), 1.30–1.90 (m), 2.10–2.44 (m), 2.79 (s), 2.84 (s), 2.95 (m), 3.15 (m), 3.83 (d, J=13,6 Hz), 3.98 (d, J=13.6 Hz), 4.04 (m), 4.41 (m), 4.57–4.70 (m), 4.82 (m), 5.07 (m), 7.02–7.29 (m), 7.48 (d, J=8.0 Hz), 7.64 (d, J=8.0 Hz), 8.47 (m), 8.52 (s), 8.76 (d, J=7.0 Hz). Anal. ($C_{52}H_{54}N_4O_5S.0.5\ H_2O$) C, H, N.

Preparation of Intermediate Benzylthiocarbonyl-L-hPhe-L-N-Me-Phe-L-(Tr-Glutaminal).

Using the procedure described in Example 4 for the preparation of cyclopentylthiocarbonyl-L-Leu-L-N-Me-L-Phe-L-(Tr-glutaminal), benzylthiocarbonyl-L-hPhe-L-N-Me-Phe-L-(Tr-glutaminal) was synthesized from benzylthiocarbonyl-L-hPhe-L-N-Me-Phe-L-(Tr-glutaminol) in 75% yield and used without further purification: white amorphous solid: $^1$H NMR (DMSO-$d_6$) (mixture of rotamers) δ 0.60 (m), 2.20–2.49 (m), 2.81 (s), 2.84 (s), 2.95 (m), 3.24 (m), 3.80–4.05 (m), 4.17 (m), 4.42 (m), 4.59 (m), 4.95 (m), 5.24 (m), 7.03–7.29 (m), 8.29 (d, J=9.0 Hz), 8.34 (d, J=8.0 Hz), 8.47 (d, J=8.0 Hz), 8.55 (s), 8.63 (s), 8.75 (d, J=7.0 Hz), 9.26 (s), 9.39 (s).

Preparation of Intermediate Ethyl-3-[Benzylthiocarbonyl-L-hPhe-L-N-Me-Phe-L-(Tr-Gln)]-E-Propenoate.

Using the procedure described in Example 4 for the preparation of ethyl-3-[cyclopentylthiocarbonyl-L-Leu-L-N-Me-Phe-L-(Tr-Gln)]-E-propenoate, ethyl-3-[benzylthiocarbonyl-L-hPhe-L-N-Me-Phe-L-(Tr-Gln)]-E-propenoate was synthesized from benzylthiocarbonyl-L-hPhe-L-N-Me-Phe-L-(Tr-glutaminal) to give material contaminated with triphenyphosphine oxide after chromatography which was used without further purification: $^1$H NMR (DMSO-$d_6$) (mixture of rotamers) δ 0.46 (m), 1.19 (t, J=7.0 Hz), 1.63–1.91 (m), 2.26 (m), 2.44 (m), 2.80 (s), 2.82 (s), 2.94 (m), 3.17 (m), 3.82 (d, J=14.0 Hz), 3.97 (d, J=13.6 Hz), 4.09 (q, J=7.0 Hz), 4.10 (q, J=7.0 Hz), 4.45 (m), 4.98 (m), 5.12 (m), 5.67 (d, J=14.0 Hz), 5.93 (d, J=15.5 Hz), 6.71 (dd, J=16.0, 5.5 Hz), 6.83 (dd, J=15.5, 5.0 Hz), 7.02–7.29 (m), 8.05 (m), 8.44 (d, J=8.0 Hz), 8.54 (s), 8.62 (s), 8.84 (d, J=6.0 Hz).

Preparation of Product -Ethyl-3-(Benzylthiocarbonyl-L-hPhe-L-N-Me-Phe-L-Gln)-E-Propenoate.

Using the procedure described in Example 4 for the preparation of ethyl-3 -(cyclopentylthiocarbonyl-L-Leu-L-N-Me-Phe-L-Gln)-E-propenoate, ethyl-3-(benzylthiocarbonyl-L-hPhe-L-N-Me-Phe-L-Gln)-E-propenoate was synthesized from ethyl-3-[benzylthiocarbonyl-L-hPhe-L-N-Me-Phe-L-(Tr-Gln)]-E-propenoate in 81% yield as a white amorphous solid (two steps from the aldehyde intermediate): mp=64–67° C.: IR(KBr) 3285, 1641, 1537, 1454, 1208, 700 cm$^{-1}$, $^1$H NMR (DMSO-$d_6$) (mixture of rotamers) δ 0.42 (m), 1.19 (t, J=7.0 Hz), 1.60–2.70 (m), 2.79 (s), 2.80 (s), 2.87 (m), 3.20 (m), 3.94–4.14 (m), 4.36–4.60 (m), 4.99 (m), 5.07 (m), 5.69 (d, J=15.5 Hz), 5.99 (d, J=15.5 Hz), 6.72 (dd, J=15.5, 5.5 Hz), 6.76 (bs), 6.86 (dd, J=15.5, 5.5 Hz), 6.98–7.30 (m), 8.03 (m), 8.50 (d, J=8.0 Hz), 8.85 (d, J=6.0 Hz). HRMS calcd for $C_{37}H_{44}N_4O_6S$+Cs 805.2036, found 805.2054. Anal. ($C_{37}H_{44}N_4O_6S.0.45\ CHCl_3$) C, H, N.

Example 9

Preparation of Compound 10: 2-(Bezylthiocarbonyl-L-hPhe-L-N-Me-Phe-L-Gln)-E-(α-Vinyl-γ-Butyrolactone).

Preparation of Intermediate 2-[Benzylthiocarbonyl-L-hPhe-L-N-Me-Phe-L-(Tr-Gln)]-E-(α-Vinyl-γ-Butyrolactone).

Using the procedure described in Example 5 for the preparation of 2-[cyclopentylthiocarbonyl-L-Leu-L-N-Me-Phe-L-(Tr-Gln)]-E-(α-vinyl-γ-butyrolactone), 2-[benzylthiocarbonyl-L-hPhe-L-N-Me-Phe-L-(Tr-Gln)]-E-(α-vinyl-γ-butyrolactone) was synthesized from benzylthiocarbonyl-L-hPhe-L-N-Me-Phe-L-(Tr-glutaminal) and (triphenylphosphoranylidene)-γ-butyrolactone to give material contaminated with triphenyphosphine oxide after column chromatography which was used without further purification: $^1$H NMR (DMSO-$d_6$) (mixture of rotamers) δ 0.63 (m), 1.39 (m), 1.62–1.90 (m), 2.80 (s), 2.82 (s), 2.10–2.95 (m), 3.10–3.28 (m), 3.85–4.05 (m), 4.24–4.40 (m), 4.45 (m), 4.62 (m), 4.82 (m), 5.07 (m), 6.26 (m), 6.39 (m), 7.02–7.30 (m), 8.05 (m), 8.49 (d, J=8.0 Hz), 8.51 (s), 8.60 (s), 8.82 (d, J=6.0 Hz).

Preparation of Product-2-(Benzylthiocarbonyl-L-hPhe-L-N-Me-Phe-L-Gln)-E-(α-Vinyl-γ-Butyrolactone).

Using the procedure described in Example 5 for the preparation of 2-(cyclopentylthiocarbonyl-L-Leu-L-N-Me-Phe-L-Gln)-E-(α-vinyl-γ-butyrolactone), 2-(benzylthiocarbonyl-L-hPhe-L-N-Me-Phe-L-Gln)-E-(α-vinyl-γ-butyrolactone) was synthesized in 70% overall yield based on two steps from benzylthiocarbonyl-L-hPhe-L-N-Me-Phe-L-(Tr-glutaminal): white amorphous solid (mp= 75–79° C.): IR(KBr) 3289, 1751, 1638, 1528, 1208, 700 cm$^{-1}$; $^1$H NMR (DMSO-$d_6$) (mixture of rotamers) δ 0.54 (m), 1.32 (m), 1.80 (m), 2.01–2.46 (m), 2.60 (m), 2.79 (s), 2.80 (s), 2.72–2.98 (m), 3.14 (m), 4.01 (d, J=13.6 Hz), 4.05 (s), 4.12 (d, J=13.6 Hz), 4.30–4.57 (m), 4.62 (m), 4.82 (m), 5.01 (m), 6.27 (m), 6.40 (m), 6.77 (m), 6.98–7.30 (m), 8.02 (d, J=8.0 Hz), 8.08 (d, J=9.0 Hz), 8.49 (d, J=8.0 Hz), 8.83 (d, J=6.0 Hz). HRMS calcd for $C_{37}H_{42}N_4O_6S$+Cs 803.1879, found 803.1863. Anal. ($C_{37}H_{42}N_4O_6S$.0.35CHCl$_3$) C, H, N.

Example 10

Preparation of Compound 11: Ethyl-3-(Ethylthiocarbonyl-L-Leu-L-N-Me-Phe-L-Gln)-E-Propenoate.

Preparation of Intermediate Ethyl-3-[BOC-L-Leu-L-N-Me-Phe-L-(Tr-Gln)]-E-Propenoate.

This material was prepared from ethyl-3-[BOC-L-(Tr-Gln)]-E-propenoate (0.397 g, 0.732 mmol) and BOC-L-Leu-L-N-Me-Phe (0.287 g, 0.731 mmol) as described in Example 6 for the formation of 1-(2',3'-dihydroindol-1-yl)-3-[BOC-L-Leu-L-N-Me-Phe-L-(Tr-Gln)]-E-propenone to give ethyl-3-[BOC-L-Leu-L-N-Me-Phe-L-(Tr-Gln)]-E-propenoate (after chromatography, 44% EtOAc in hexanes) as a white foam (0.412 g, 69%): IR (thin film) 3295, 1713, 1672, 1649 cm$^{-1}$; $^1$H NMR (CDCl$_3$) (mixture of isomers) δ 0.65 (d, J=6.2 Hz), 0.66 (d, J=6.5 Hz), 0.84 (d, J=6.5 Hz), 0.88 (d, J=6.5 Hz), 1.02–1.22 (m), 1.23–1.38 (m), 1.33 (s), 1.41 (s), 1.55–1.82 (m), 1.89–2.07 (m), 2.23–2.30 (m), 2.90 (s), 2.94 (s), 3.01 (dd, J=14.6, 10.9 Hz), 3.03–3.13 (m), 3.26–3.37 (m), 3.27 (dd, J=14.6, 3.4 Hz), 3.42–3.54 (m), 4.00–4.22 (m), 4.37–4.73 (m), 4.82–4.89 (m), 5.63–5.70 (m), 5.95 (dd, J=15.9, 1.2 Hz), 6.23–6.28 (m), 6.66–6.75 (m), 6.79–6.89 (m), 7.09–7.34 (m), 8.14 (d, J=8.7 Hz); Anal. ($C_{49}H_{60}N_4O_7$) C, H, N.

Preparation of Intermediate Ethyl-3-[Ethylthiocarbonyl-L-Leu-L-N-Me-Phe-L-(Tr-Gln)]-E-Propenoate.

Ethyl-3-[BOC-L-Leu-L-N-Me-Phe-L-(Tr-Gln)]-E-propenoate (0.390 g, 0.477 mmol) was deprotected and coupled with ethyl chlorothiolformate (0.063 mL, 0.60 mmol) as described in Example 6 for the formation of 2,3-dihydroindole-3-[ethylthiocarbonyl-L-Leu-L-N-Me-Phe-L-(Tr-Gln)]-E-propenamide to give ethyl-3-[ethylthiocarbonyl-L-Leu-L-N-Me-Phe-L-(Tr-Gln)]-E-propenoate (after chromatography, 44% EtOAc in hexanes) as a white foam (0.261 g, 68%): IR (thin film) 3295, 1708, 1648 cm$^{-1}$; $^1$H NMR (CDCl$_3$) (mixture of isomers) δ 0.61–0.75 (m), 0.92 (d, J=6.8 Hz), 0.68 (d, J=6.5 Hz), 0.82–0.98 (m), 0.86 (d, J-=6.5 Hz), 0.87 (d, J=6.2 Hz), 1.04–1.43 (m), 1.51–1.84 (m), 1.88–2.08 (m), 2.21–2.32 (m), 2.66–3.53 (m), 2.86 (s), 2.89 (s), 4.08–4.24 (m), 4.28–4.53 (m), 4.54–4.68 (m), 4.83–4.89 (m), 5.65–5.76 (m), 5.74 (d, J=15.7 Hz), 5.96 (d, J=15.7 Hz), 6.35–6.40 (m), 6.75 (dd, J=15.7, 5.3 Hz), 6.80–6.89 (m), 7.09–7.35 (m), 8.03 (d, J=7.5 Hz); Anal. ($C_{47}H_{56}N_4O_6S$) C, H, N.

Preparation of Product Ethyl-3-(Ethylthiocarbonyl-L-Leu-L-N-Me-Phe-L-Gln)-E-Propenoate.

Ethyl-3-[ethylthiocarbonyl-L-Leu-L-N-Me-Phe-L-(Tr-Gln)]-E-propenoate (0.220 g, 0.273 mmol) was deprotected using the procedure described in Example 1 for the formation of ethyl-3-(CBZ-L-N-Me-Phe-L-Gln)-E-propenoate to give ethyl-3-(ethylthiocarbonyl-L-Leu-L-N-Me-Phe-L-Gln)-E-propenoate (after chromatography, 50% acetone in hexanes) as a white foam (0.111 g, 72%): IR (thin film) 3284, 1660 cm$^{-1}$; $^1$H NMR (CDCl$_3$) (mixture of isomers) δ 0.62 (d, J=6.5 Hz), 0.67 (d, J=6.5 Hz), 0.89 (d, J=6.5 Hz), 0.93 (d, J=6.5 Hz), 1.22 (t, J=7.2 Hz), 1.29 (t, J=7.2 Hz), 1.37–2.04 (m), 2.13–2.44 (m), 2.58–3.36 (m), 2.93 (s), 3.12 (s), 4.17 (q, J=7.2 Hz), 4.19 (q, J=7.2 Hz), 4.37–4.90 (m), 4.96–5.15 (m), 5.67 (d, J=15.6 Hz), 6.00 (d, J=15.6 Hz), 6.12 (s, bs), 6.62–6.72 (m), 6.87 (dd, J=15.6, 5.9 Hz), 6.95 (bs), 7.12–7.35 (m), 7.47 (bs), 7.83 (d, J=7.2 Hz); Anal. ($C_{28}H_{42}N_4S$.0.5 H$_2$O) C, H, N.

Example 11

Preparation of Compound 12: 2-(Ethylthiocarbonyl-L-Val-L-N-Me-Phe-L-Gln)-E-(α-Vinyl-γ-Butyrolactone).

Preparation of Intermediate BOC-L-Val-L-N-Me-Phe-OMe.

N-Me-Phe-OMeHCl (2.0 g) was dissolved in 50 mL of CH$_2$Cl$_2$ and poured into a combination of 1N NaOH (aq. 7 mL) and sat. NaHCO$_3$ (25 mL). After mixing, the organic phase was separated, and the aqueous phase was extracted with CH$_2$Cl$_2$ (3×50 mL). The combined organic phases were dried over Na$_2$SO$_4$ and concentrated to give the free base of the amine as a clear colorless oil (1.69 g, 8.75 mmol). A solution of this amine and diisopropylethylamine (1.68 mL, 9.62 mmol) in 10 mL of DMF was added dropwise to a solution of BOC-L-Val (2.09 g, 9.62 mmol) and hydroxybenzotriazole-hydrate (1.30 g, 9.62 mmol) in 10 mL DMF cooled to 0° C. 1,3-Dicyclohexylcarbodiimide (2.18 g, 10.59 mmol) was then added. The reaction mixture was stirred at 0° C. for 1 h, and then stirred at rt. for 48 h. The mixture was filtered to remove the precipitate, and the filtrate was evaporated. The residue was dissolved in CH$_2$Cl$_2$ (200 mL), washed with sat. NaHCO$_3$ (100 mL), dried over Na$_2$SO$_4$, concentrated, and purified by flash column chromatography (15 % EtOAc in hexane) to give BOC-L-Val-L-N-Me-Phe-OMe as a white solid (2.56 g, 75%). IR (thin film) 2972, 1743, 1710, 1646, 1497, 1172 cm$^{-1}$; $^1$H NMR (mixture of rotamers) (CDCl$_3$): δ 0.34 (d, J=6.9 Hz), 0.66 (d, J=6.9 Hz), 0.89 (d, J=6.9 Hz), 0.95 (d, J=6.9 Hz), 1.41 (s), 1.87–1.98 (m), 2.92 (s), 2.94 (s), 2.99–3.01 (m), 3.37 (d, J=5.7 Hz), 3.42 (d, J=5.7 Hz), 3.72 (s), 3.73 (s), 4.35 (dd, J=9.3, 6.0 Hz); 4.94–5.02 (m), 5.07 (d, J=9.3 Hz), 5.34 (dd, J=9.9, 3.0 Hz), 7.17–7.32 (m). Anal. ($C_{21}H_{32}N_2O_5$) C, H, N.

Preparation of Intermediate BOC-L-Val-L-N-Me-Phe.

BOC-L-Val-L-N-Me-Phe-OMe (0.396 g, 1.01 mmol) was dissolved in 10 mL of MeOH and cooled to 0° C. A solution of 2 N NaOH (aq 4.04 mL, 8.08 mmol) was added dropwise. The reaction mixture was stirred for 2 h at rt. and poured into 10% aq $KHSO_4$ (80 mL) and extracted with $CH_2Cl_2$ (2×100 mL). The combined organic layers were dried over $Na_2SO_4$ and concentrated to give BOC-L-Val-L-N-Me-Phe (0.38 g, quant.) which was used without purification.

Preparation of Intermediate 2-[BOC-L-Val-L-N-Me-Phe-L-(Tr-Gln)]-E-(α-Vinyl-γ-Butyrolactone).

2-[BOC-L-(Tr-Gln)]-E-(α-vinyl-γ-butyrolactone) (0.546 g, 1.01 mmol) was deprotected and coupled with BOC-L-Val-L-N-Me-Phe (0.38 g, 1.01 mmol) using the procedure described in Example 7 for the formation of the 2-[BOC-L-Leu-L-N-Me-Phe-L-(Tr-Gln)]-E-(α-vinyl-γ-butyrolactone) to give 2-[BOC-L-Val-L-N-Me-Phe-L-(Tr-Gln)]-E-(α-vinyl-γ-butyrolactone) as a white foam (0.613 g, 76%): IR (thin film) 3307, 2965, 1752, 1677, 1493, 1171 cm$^{-1}$; $^1$H NMR (mixture of rotamers) (CDCl$_3$) δ 0.68 (d, J=8.1 Hz), 0.81 (d, J=6.6 Hz), 0.86 (d, J=6.9 Hz), 1.38–1.45 (m), 1.78–2.00 (m), 2.25–2.27 (m), 2.64–2.99 (m), 3.28–3.47 (m), 3.55 (s), 3.59–3.76 (m), 4.04–4.07 (m), 4.24–4.31 (m), 4.42–4.46 (m), 4.74–4.80 (m), 4.90 (d, J=6.9 Hz), 4.94–5.03 (m), 6.27–6.31 (m), 6.46–6.49 (m), 6.84 (s), 6.96 (s), 7.02 (s), 7.12–7.33 (m), 7.46–7.49 (m), 7.53–7.55 (m), 7.64–7.70 (m), 7.93 (d, J=8.1 Hz); Anal. ($C_{48}H_{56}N_4O_7$.0.5 $H_2O$)C, H, N.

Preparation of Intermediate 2-[Ethylthiocarbonyl-L-Val-L-N-Me-Phe-L-(Tr-Gln)]-E-(α-Vinyl-γ-Butyrolactone).

2-[BOC-L-Val-L-N-Me-Phe-L-(Tr-Gln)]-E-(α-vinyl-γ-butyrolactone) (0.376, 0.47 nmmol) was deprotected and coupled with ethyl chlorothiolformate (0.06 mL, 0.47 mmol) as described in Example 7 for the formation of 2-[ethylthiocarbonyl-L-Leu-L-N-Me-Phe-L-(Tr-Gln)]-E-(α-vinyl-γ-butyrolactone) to give 2-[ethylthiocarbonyl-L-Val-L-N-Me-Phe-L-(Tr-Gln)]-E-(α-vinyl-γ-butyrolactone) as a white foam (0.150 mg, 40%): IR (thin film) 3299, 2965, 2360, 1751, 1493, 1205 cm$^{-1}$; $^1$H NMR (mixture of rotamers) (CDCl$_3$) δ 0.36 (d, J=6.9 Hz), 0.54 (d, J=6.6 Hz), 0.71 (d, J=6.9 Hz), 0.85 (d, J=6.3 Hz), 1.21–1.31 (m), 1.82–1.84 (m), 2.28–2.30 (m), 2.64–3.03 (m), 3.31–3.41 (m), 3.62–3.78 (m), 4.24–4.33 (m), 4.45–4.52 (m), 4.60–4.66 (m), 5.81–5.89 (m), 6.33–6.36 (m), 6.41–6.49 (m), 6.86(s), 7.06 (s), 7.11–7.33 (m), 7.46–7.50 (m), 7.54–7.55 (m), 7.64–7.70 (m), 7.79 (d, J=7.5 Hz). Anal. ($C_{46}H_{52}N_4O_6S$.0.5 $H_2O$) C, H, N.

Preparation of Product-2-(Ethylthiocarbonyl-L-Val-L-N-Me-Phe-L-Gln)-E-(α-Vinyl-γ-Butyrolactone).

2-[Ethylthiocarbonyl-L-Val-L-N-Me-Phe-L-(Tr-Gln)]-E-(α-vinyl-γ-butyrolactone) was deprotected using the procedure described in Example 7 for the formation of 2-(ethylthiocarbonyl-L-Leu-L-N-Me-Phe-L-Gln)-E-(α-vinyl-γ-butyrolactone) to give 2-(ethylthiocarbonyl-L-Val-L-N-Me-Phe-L-Gln)-E-(α-vinyl-γ-butyrolactone) as a white solid (0.068 g, 96%): IR (thin film) 3748, 1625, 1541, 1200 cm$^{-1}$; $^1$H NMR (mixture of rotamers) (DMSO-d$_6$) δ 0.27 (d, J=6.6 Hz), 0.38 (d, J=6.3 HZ), 0.55–0.59 (m), 0.79–0.84 (m), 1.11–1.17 (m), 1.70–1.83 (m), 1.88–1.95 (m), 1.98–2.07 (m), 2.72–3.26 (m), 4.05–4.10 (m), 4.25–4.44 (m), 4.64–4.66 (m), 5.12–5.18 (m), 5.33–5.36 (m), 6.23–6.26 (m), 6.34–6.39 (m), 6.75–6.78 (m), 7.12–7.26 (m), 7.78–7.84 (m), 8.13 (d, J=7.5 Hz), 8.24–8.30 (m). HRMS calcd. for (M+Cs), 679.1566, found 679.1591. Anal. ($C_{27}H_{38}N_4O_6S$.0.3 $H_2O$) C,H,N.

Example 12

Preparation of Compound 13: Ethyl-3-[Benzylthiocarbonyl-L-hPhe-L-N-Me-(4-Me-Phe)-L-Gln] -E-Propenoate Preparation of Intermediate FMOC-L-N-Me-(4-Me)-Phe.

This N-protected amino acid was prepared in approximately 80% yield from FMOC-L-(4-Me)-Phe, purchased from Neosystem Laboratories, Strasbourg, France, using the procedure described by R. M. Friedinger, et al.; *J. Org. Chem.* 1983, 48, 77–81, the disclosure of which is entirely incorporated by reference herein. The crude product, isolated as an oil, was used without further purification: IR (thin film) 3452, 2953, 1713, 1516, 1451, 1404, 1321, 1194, 1040, 738 cm$^{-1}$; $^1$H NMR (CDCl$_3$) mixture of rotamers; δ 2.27 (m), 2.77 (s), 2.79 (s), 2.85 (s), 3.08–3.32 (m), 3.37–3.49 (m), 4.10–4.26 (m), 4.30–4.45 (m), 4.80–4.89 (m), 5.05 (m), 6.87 (d, J=11.0 Hz), 6.95 (d, J=11.0 Hz), 7.09 (m), 7.25–7.55 (m), 7.75 (d, J=7.4 Hz). MS calcd for $C_{26}H_{25}NO_4$+Na 438, found 438.

Preparation of Intermediate FMOC-L-N-Me-(4-Me)-Phe-L-(Tr-Glutaminol).

FMOC-L-N-Me-(4-Me)-Phe (1.90 g, 4.6 mmol) was dissolved in 12 mL of $CH_2Cl_2$ and 2 mL of DMF. To this solution was added N-hydroxysuccinimide (0.53 g, 4.6 mmol) was added to this solution. Stirring was continued until all the solids were dissolved. N,N'-Dicyclohexylcarbodiimide (0.95 g, 4.6 mmol) was added to the reaction mixture, and the reaction was stirred at room temperature for two hours. The mixture was then filtered into a separate flask containing L-(Tr-Glutaminol) (1.72 g, 4.6 mmol) dissolved in 15 mL of DMF, removing the N,N'-dicyclohexylurea precipitate. The reaction mixture was stirred overnight at room temperature. The solvents were removed under vacuum, and the resulting crude product was purified by flash chromatography (5% saturated anhydrous NH$_3$ in MeOH/CH$_2$Cl$_2$) on silica gel to give 3.72 g (90%) of a white solid: IR (KBr) 3407, 3312, 3059, 3032, 2932, 1665, 1516, 1491, 1447, 1319, 1188, 741, 700 cm$^{-1}$; $^1$H NMR (DMSO-d$_6$) mixture of rotamers; δ 1.55 (m), 1.67 (m), 2.16 (bs), 2.23 (bs), 2.79 (s), 3.00–3.29 (m), 3.75 (m), 4.01–4.10 (m), 4.25 (m), 4.50–4.64 (m), 4.85 (m), 6.98–7.39 (m), 7.49 (d, J=7.4 Hz), 7.60–7.75 (m), 7.87 (d, 1 H, J=7.4 Hz), 8.50 (bs). MS calcd for $C_{50}H_{49}N_3O_5$+Na 794, found 794.

Preparation of Intermediate L-N-Me-(4-Me)-Phe-L-(Tr-Glutaminol).

FMOC-L-N-Me-(4-Me)-Phe-L-(Tr-Glutaminol) (3.32 g, 4.3 mmol) was dissolved in 11 mL of DMF. Piperidine (0.44 g, 5.2 mmol) was added dropwise to this solution. The solution was stirred for 30 min. At this time, the solution was concentrated under vacuum, and the resulting crude amine was purified by flash chromatography (7% MeOH/CH$_2$Cl$_2$) on silica gel to give 2.12 g (90%) of a white tacky foam: IR (thin film) 3302, 3057, 3025, 2934, 2865, 1956, 1925, 1809, 1659, 1516, 1265, 1035, 737, 700 cm$^{-1}$; $^1$H NMR (CDCl$_3$) δ 1.73 (m, 1H), 1.89 (m, 1H), 2.26 (s, 3H), 2.30 (s, 3H), 2.37 (m, 2H), 2.67 (dd, 1H, J=13.8, 9.0 Hz), 3.09 (dd, 1H, J=13.4, 4.6 Hz), 3.20 (dd, 1H, J=8.8, 4.4 Hz), 3.42 (m, 2H), 3.52 (m, 1H), 3.82 (m, 1H), 3.91 (m, 1H), 6.94 (m, 2H), 7.09 (m, 2H), 7.23–7.32 (m, 16H), 7.44 (d, 1 H, J=7.7 Hz). MS calcd for $C_{35}H_{39}N_3O_3$+Cs 682, found 682.

Preparation of Intermediate CBZ-L-hPhe-L-N-Me-(4-Me)-Phe-L-(Tr-Glutaminol).

Following the procedure of L. A. Carpino, *J. Am. Chem. Soc.* 1993, 115, 4397, the disclosure of which is entirely incorporated herein by reference, CBZ-L-hPhe was coupled with L-N-Me-(4-Me)-Phe-L-(Tr-Glutaminol) as follows. To CBZ-L-hPhe (0.32 g, 1.0 mmol) was added 3 mL of DMF. To this solution was added L-N-Me-(4-Me)-Phe-L-(Tr-Glutaminol) (0.55 g, 1.0 mmol) and diisopropylethylamine (0.26 g, 2.0 mmol). This solution was then cooled to 0° C., and O-(7-azabenzotriazol-1-yl)-1,1,3,3-tetramethyluronium hexafluorophosphate (HATU) (0.38 g, 1.0 mmol) was added. The solution instantly turned yellow, and the mixture was allowed to warm to rt. Once the starting materials were consumed as indicated by TLC, the reaction mixture was concentrated under vacuum. The residue was taken up in an excess of EtOAc (200 mL), and washed with 25 mL of $H_2O$, 25 mL 10% HCl twice, and then 5% aq $NaHCO_3$. The organic layer was dried over anh $Na_2SO_4$ and concentrated. The residue was subjected to flash chromatography (5% MeOH/$CH_2Cl_2$) on silica gel to give 0.68 g (80%) of a white solid: IR (KBr) 3403, 3059, 3030, 2947, 1662, 1516, 1448, 1264, 752, 700 cm$^{-1}$; $^1$H NMR (DMSO-$d_6$) mixture of rotamers; δ 0.45 (m), 1.27–1.65 (m), 1.77–1.95 (m), 1.97 (s), 2.07–2.15 (m), 2.18 (s), 2.19–2.25 (m), 2.37 (m), 2.68–2.94 (m), 3.05–3.35 (m), 3.75 (m), 3.80 (m), 4.20–4.40 (m), 4.54–5.03 (m), 6.92–7.34 (m), 7.43–7.85 (m), 8.49 (m). MS calcd for $C_{53}H_{56}N_4O_6$+Cs 977, found 977.

Preparation of Intermediate L-hPhe-L-N-Me-(4-Me)-Phe-L-(Tr-Glutaminol).

Using the catalytic hydrogenation procedure described in Example 4 for the preparation of L-(Tr-Glutaminol), the amine was prepared in quantitative yield from CBZ-L-hPhe-L-N-Me-(4-Me)-Phe-L-(Tr-Glutaminol). White glassy solid: IR (KBr) 3378, 3057, 3027, 2938, 1659, 1516, 1493, 1447, 1180, 752, 700 cm$^{-1}$; $^1$H NMR (DMSO-$d_6$) mixture of rotamers; δ 1.30–1.60 (m), 1.68 (m), 2.07 (m), 2.16 (s), 2.22 (m), 2.57 (m), 2.68 (s), 2.77 (s), 2.82–3.30 (m), 3.75 (m), 4.30–4.80 (m), 4.90–5.00 (m), 6.97–7.43 (m), 8.35–8.55 (m). MS calcd for $C_{45}H_{50}N_4O_4$+Na 733, found 733.

Preparation of Intermediate Benzylthiocarbonyl-L-hPhe-L-N-Me-(4-Me)-Phe-L-(Tr-Glutaminol).

Using the procedure described in Example 8 for the preparation of benzylthiocarbonyl-L-hPhe-L-N-Me-Phe-L-(Tr-Glutaminol), benzylthiocarbonyl-L-hPhe-L-N-Me-(4-Me)-Phe-L-(Tr-glutaminol) was prepared from L-hPhe-L-N-Me-(4-Me)-Phe-L-(Tr-glutaminol) and benzyl chlorothiolformate in 96% yield. White solid: IR (KBr) 3418, 3316, 3054, 3023, 2947, 1678, 1666, 1643, 1530, 1493, 1451, 1211, 700 cm$^{-1}$; $^1$H NMR (DMSO-$d_6$) mixture of rotamers; δ 0.55 (m), 1.25–1.60 (m), 1.80–1.93 (m), 1.96 (s), 2.19 (s), 2.22 (m), 2.40 (m), 2.68 (s), 2.72–2.96 (m), 3.17–3.27 (m), 3.40 (m), 3.65 (m), 3.80–4.10 (m), 4.54–5.03 (m), 6.84–7.29 (m), 7.47 (d, J=8.1 Hz), 7.55 (d, J=7.5 Hz), 7.66 (d, J=8.4 Hz), 8.44–8.52 (m), 8.76 (d, J=7.5 Hz). MS calcd for $C_{53}H_{56}N_4O_5$S+Na 883, found 883.

Preparation of Intermediate Benzylthiocarbonyl-L-hPhe-L-N-Me-(4-Me)-Phe-L-(Tr-Glutaminal).

Benzylthiocarbonyl-L-hPhe-L-N-Me-(4-Me)-Phe-L-(Tr-Glutaminol) was oxidized using o-iodoxybenzoic acid in anh. DMSO as described in Example 4 for the preparation of cyclopentylthiocarbonyl-L-Leu-L-N-Me-Phe-L-(Tr-glutaminal). Upon workup, the aldehyde was used immediately without further purification. $^1$H NMR (CDCl$_3$) mixture of rotamers; δ 0.89 (m), 1.26 (m), 1.67 (m), 1.85–2.05 (m), 2.13 (s), 2.22 (m), 2.28 (s), 2.35 (m), 2.60 (m), 2.70 (s), 2.83 (s), 2.89–2.95 (m), 2.99 (s), 3.01 (m), 3.25 (m), 3.90 (m), 4.04–4.25 (m), 4.30 (m), 4.61–4.66 (m), 5.85 (d, J=7.0 Hz), 5.95 (d, J=7.0 Hz), 6.22 (d, J=7.0 Hz), 6.70–7.36 (m), 8.15 (d, J=7.0 Hz). 9.35 (s), 9.40 (s).

Preparation of Intermediate Ethyl-3-[Benzylthiocarbonyl-L-hPhe-L-N-Me-(4-Me)-Phe-L-(Tr-Gln)]-E-Propenoate.

This intermediate was prepared from benzylthiocarbonyl-L-hPhe-L-N-Me-(4-Me)-Phe-L-(Tr-glutaminal) and (carbethoxymethylene)triphenylphosphorane as described in Example 4 for the preparation of ethyl-3-[cyclopentylthiocarbonyl-L-Leu-L-N-Me-Phe-L-(Tr-Gln)]-E-propenoate. White solid: IR (thin film) 3297, 3057, 3027, 2980, 2928, 1714, 1651, 1516, 1495, 1447, 1267, 1213, 1035, 735, 700 cm$^{-1}$; $^1$H NMR (CDCl$_3$) mixture of rotamers; δ 0.88 (m), 1.26 (t, J=7.2 Hz), 1.44 (m), 1.61–1.80 (m), 1.94 (m), 2.10 (s), 2.23 (m), 2.29 (s), 2.54 (m), 2.67 (s), 2.85 (s), 2.90 (m), 2.98 (s), 3.03 (m), 3.17–3.29 (m), 3.84–4.07 (m), 4.14 (m), 4.35 (m), 4.58 (m), 5.73 (dd, J=15.8, 1.5 Hz), 5.91–5.99 (m), 6.04 (d, J=7.7 Hz), 6.47 (d, J=8.5 Hz), 6.72 (dd, J=15.5, 5.1 Hz), 6.82 (m), 6.87–7.08 (m), 7.14–7.31 (m), 7.77 (d, J=7.0 Hz). MS calcd for $C_{57}H60N_4O_6$S+Na 951, found 951.

Preparation of Product-Ethyl-3-[Benzylthiocarbonyl-L-hPhe-L-N-Me-(4-Me)-Phe-L-Gln]-E-Propenoate.

This product was prepared in 69% overall yield (3 steps) from intermediate benzylthiocarbonyl-L-hPhe-L-N-Me-(4-Me)-Phe-L-(Tr-Glutaminol) by the deprotection of ethyl-3-[benzylthiocarbonyl-L-hPhe-L-N-Me-(4-Me)-Phe-L-(Tr-Gln)]-E-propenoate using the procedure described in Example 4 for the synthesis of ethyl-3-(cyclopentylthiocarbonyl-L-Leu-L-N-Me-Phe-L-Gln)-E-propenoate. White solid: IR (KBr) 3414, 3327, 3293, 3205, 3025, 2980, 2930, 1717, 1674, 1644, 1537, 1454, 1283, 1217, 1194, 700 cm$^{-1}$; $^1$H NMR (DMSO-$d_6$) mixture of rotamers; δ 0.30 (m), 0.84 (m), 1.19 (t, J=7.0 Hz), 1.33 (m), 1.77 (m), 1.92 (s), 2.05 (m), 2.20 (s), 2.40 (m), 2.57 (m), 2.77 (s), 2.80 (s), 2.84–2.90 (m), 3.05 (m), 3.94–4.14 (m), 4.36–4.60 (m), 5.01 (m), 5.63–5.73 (m), 6.01 (dd, J=15.8, 1.1 Hz), 6.68–6.91 (m), 6.93–7.35 (m), 7.70 (m), 8.02 (m), 8.48 (d, J=8.1 Hz), 8.65 (d, J=8.0 Hz), 8.85 (d, J=5.9 Hz). HRMS calcd for $C_{38}H46N_4O_6$S+Cs 819.2192, found 819.2177. Anal. ($C_{38}H_{46}N_4O_6$S) C, H, N, S.

Example 13

Preparation of Compound 14; Ethyl-2-Methyl-3-[Benylthiocarbonyl-L-hPhe-L-N-Me-(4-Me)-Phe-L-Gln]-E-Propenoate.

Preparation of Intermediate Ethyl-2-Methyl-3-[Benzylthiocarbonyl-L-hPhe-L-N-Me-(4-Me)-Phe-L-(Tr-Gln)]-E-Propenoate.

This intermediate was prepared from benzylthiocarbonyl-L-hPhe-L-N-Me-(4-Me)-Phe-L-(Tr-glutaminal) using (carbethoxyethylidene)triphenylphosphorane in place of (carbethoxymethylene)triphenylphosphorane in the procedure described in Example 4 for the preparation of ethyl-3-[cyclopentylthiocarbonyl-L-Leu-L-N-Me-Phe-L-(Tr-Gln)]-E-propenoate. After column chromatography on silica gel (5% MeOH/$CH_2Cl_2$), two fractions were collected, one impure with triphenylphosphine oxide. (Analytical sample) White solid: IR (thin film) 3289, 3057, 3027, 2978, 2928, 1707, 1676, 1642, 1516, 1495, 1449, 1253, 1215, 750, 700 cm$^{-1}$; $^1$H NMR (CDCl$_3$) mixture of rotamers: δ 0.83 (m), 1,26 (m), 1.47–1.50 (m), 1.63–1.70 (m), 1.78 (m), 1.85 (d, J=1.5 Hz), 1.87 (m), 1.92 (d, J=1.5 Hz), 2.10 (s), 2.20 (m), 2.30 (s), 2.35–2.61 (m), 2.71 (s), 2.88 (s), 2.92 (m), 2.92 (m), 2.99 (s), 3.03–3.29 (m), 3.93 (d, J=13.6 Hz), 4.06–4.23 (m), 4.35 (m), 4.52–4.69 (m), 5.94 (d, J=7.4 Hz), 6.23 (d, J=8.5 Hz), 6.28 (d, J=7.7 Hz), 6.42 (dd, J=9.0, 1.3 Hz), 6.58 (dd, J=9.4, 1.3 Hz), 6.89 (bs), 6.92–7.17 (m), 7.20–7.33 (m), 7.64 (d, J=7.7 Hz). MS calcd for $C_{58}H_{62}N_4O_6S$+Na 965, found 965.

Preparation of Product-Ethyl-2-Methyl-3-[Benzylthiocarbonyl-L-hPhe-L-N-Me-(4-Me)-Phe-L-Gln]-E-Propenoate.

This product was prepared in 89% overall yield (3 steps) from intermediate benzylthiocarbonyl-L-hPhe-L-N-Me-(4-Me)-Phe-L-(Tr-Glutaminol) by the deprotection of ethyl-2-methyl-3 -[benzylthiocarbonyl-L-hPhe-L-N-Me-(4-Me)-Phe-L-(Tr-Gln)]-E-propenoate using the procedure described in Example 4 for the synthesis of ethyl-3-(cyclopentylthiocarbonyl-L-Leu-L-N-Me-Phe-L-Gln)-E-propenoate. White solid: IR (KBr) 3302, 3223, 2984, 2928, 1709, 1672, 1642, 1535, 1453, 1256, 1217, 1132, 700 cm$^{-1}$; $^1$H NMR (DMSO-d$_6$) mixture of rotamers; δ 0.34 (m), 1.17(m), 1.30 (m), 1.72 (m), 1.78 (s), 1.87 (s), 1.93 (s), 1.97–2.04 (m), 2.19 (s), 2.40 (m), 2.59 (m), 2.77 (s), 2.79 (s), 2.83 (m), 3.05 (m), 4.07 (m), 4.39 (m), 4.64 (m), 4.85 (m), 4.91 (m), 6.40 (d, J=9.6 Hz), 6.54 (d, J=8.5, 1.1 Hz), 6.74 (m), 6.76–7.30 (m), 7.99 (d, J=8.1 Hz), 8.47 (d, J=6.6 Hz), 8.84 (d, J=6.3 Hz). HRMS calcd for $C_{39}H_{48}N_4O_6S$+Cs 833.2349, found 833.2329. Anal. ($C_{39}H_{48}N_4O_6S$) C, H, N, S.

Example 14

Preparation of Compound 15: Ethyl-3-(Benzylthiocarbonyl-L-Leu-L-N-Me-Phe-L-Gln)-E-Propenoate.

Preparation of Intermediate Benzylthiocarbonyl-L-Leu-OMe.

To 2-isocyanato-4-methylvaleric acid methyl ester (0.86 g, 5.0 mmol) dissolved in 50 mL of THF was added benzyl mercaptan (0.59 mL, 5.0 mmol). The reaction mixture was stirred at rt overnight, and the solvent was removed in vacuo to give a yellow liquid which was purified by flash column chromatography on silica gel (gradient; 5–10% of EtOAc/hexanes) to give 1.39 g (94%) of benzylthiocarbonyl-L-Leu-OMe as a clear oil: IR (neat) 3320, 2957, 1746, 1651, 1520, 1454, 1200, 839, 702 cm$^{-1}$; $^1$H NMR (DMSO-d$_6$) δ 0.97 (m, 6H), 1.65 (m, 3H), 3.74 (s, 3H), 4.16 (s, 2H), 4.60 (m, 1H), 5.72 (d, 1H, J=8.0 Hz), 7.32 (m, 5H). Anal. ($C_{15}H_{21}NO_3S$) C, H, N.

Preparation of Intermediate Benzylthiocarbonyl-L-Leu.

Benzylthiocarbonyl-L-Leu-OMe (0.85 g, 2.88 mmol) was dissolved in 30 mL of THF. To this solution was added 1N LiOH (3.0 mL, 3.0 mmol), and the reaction mixture was stirred at rt overnight. At this time an additional 1.5 mL of 1N LiOH was added, and the reaction mixture was further stirred for 4 h. At this time, an additional 1.5 mL of 1N LiOH was added. After another 3 h at room temperature, the pH was adjusted to 7 with 10% HCl, and the THF was removed in vacuo. The aqueous phase was washed with Et$_2$O and separated, then adjusted to pH 1–2. The product was extracted with CH$_2$Cl$_2$, and the organic phase washed with brine, dried over MgSO$_4$, filtered, and then concentrated to give 0.29 g of benzylthiocarbonyl-L-Leu as a clear liquid that was contaminated with benzyl mercaptan: $^1$H NMR (DMSO-d$_6$) δ 0.83 (d, 3H, J=6.0 Hz), 0.87 (d, 3H, J=6.0 Hz), 1.45 (m, 3H), 4.04 (s, 2H), 4.22 (m, 1H), 7.27 (m, 5H), 8.46 (d, 1H, J=7.0 Hz). MS calcd for $C_{14}H_{19}NO_3S$+H 282, found 282.

Preparation of Intermediate Benzylthiocarbonyl-L-Leu-L-N-Me-Phe-L-(Tr-Glutaminol).

Using the procedure described in Example 4 for the preparation of cyclopenylthiocarbonyl-L-Leu-L-N-Me-Phe-L-(Tr-glutaminol), benzylthiocarbonyl-L-Leu-L-N-Me-Phe-L-(Tr-glutaminol) was synthesized from L-N-Me-Phe-L-(Tr-glutaminol) and benzylthiocarbonyl-L-Leu in 58% yield: white amorphous solid: IR(KBr) 3289, 3057, 3027, 2953, 1638, 1493, 1449, 1206, 700 cm$^{-1}$; $^1$H NMR (DMSO-d$_6$) (mixture of rotamers) δ 0.19 (m), 0.60 (m), 0.79 (d, J=6.2 Hz), 0.80 (d, J=6.2 Hz), 1.12–1.77 (m), 2.12–2.36 (m), 2.84 (s), 2.90 (m), 2.96 (s), 3.12–3.40 (m), 3.63 (m), 3.84 (d, J=13.6 Hz), 3.96 (d, J=13.6 Hz), 4.02 (s), 4.33 (m), 4.66 (m), 5.06 (m), 7.10–7.28 (m), 7.47 (d, J=9 Hz), 7.61 (d, J=8.5 Hz), 8.35 (d, J=7.0 Hz), 8.51 (s), 8.56 (d, J=7.0 Hz). Anal. ($C_{48}H_{54}N_4O_5S$) C, H, N.

Preparation of Intermediate Benzylthiocarbonyl-L-Leu-L-N-Me-Phe-L-(Tr-Glutaminal).

Using the procedure described in Example 4 for the preparation of cyclopenylthiocarbonyl-L-Leu-L-N-Me-Phe-L-(Tr-glutaminal), benzylthiocarbonyl-L-Leu-L-N-Me-Phe-L-(Tr-glutaminal) was synthesized from benzylthiocarbonyl-L-Leu-L-N-Me-Phe-L-(Tr-glutaminol) in 93% yield and was used without further purification: white amorphous solid: $^1$H NMR (DMSO-d$_6$) (mixture of rotamers) δ 0.02 (m), 0.61 (d, J=6.6 Hz), 0.64 (d, J=6.6 Hz), 0.81 (d, J=6.2 Hz), 1.05–1.75 (m), 1.98 (m), 2.23–2.48 (m), 2.84 (s), 2.93 (m), 2.96 (s), 3.23 (m), 3.84 (d, J=13.6 Hz), 3.95 (d, J=14.0 Hz), 4.01 (m), 4.12 (m), 4.42 (m), 4.71 (m), 4.83 (m), 5.18 (m), 7.11–7.28 (m), 8.27 (d, J=8.0 Hz), 8.31 (m), 8.57 (m), 8.62 (s), 9.27 (s), 9.40 (s).

Preparation of Intermediate Ethyl-3-[Benzylthiocarbonyl-L-Leu-L-N-Me-Phe-L-Tr-Gln)]-E-Propenoate.

Using the procedure described in Example 4 for the preparation of ethyl-3-[cyclopentylthiocarbonyl-L-Leu-L-N-Me-Phe-L-(Tr-Gln)]-E-propenoate, ethyl-3-[benzylthiocarbonyl-L-Leu-L-N-Me-Phe-L-(Tr-Gln)]-E-propenoate was synthesized from benzylthiocarbonyl-L-Leu-L-N-Me-Phe-L-(Tr-glutaminal) to give 0.30 g of material contaminated with triphenylphosphine oxide after chromatography which was used without further purification: white amorphous solid: $^1$H NMR (DMSO-d$_6$) (mixture of rotamers) δ −0.12 (m), 0.86 (d, J=6.2 Hz), 0.87 (d, J=6.2 Hz), 1.23 (t, J=7.0 Hz), 1.26 (t, J=7.0 Hz), 1.49 (m), 1.72 (m), 2.10–2.45 (m), 2.88 (s), 2.96 (m), 3.03 (s), 3.17 (m), 3.83 (d, J=13.6 Hz), 3.96 (d, J=13.6 Hz), 4.03 (s), 4.08 (m), 4.39 (m), 4.50 (m), 4.66 (m), 4.81 (m), 5.08 (m), 5.72 (d, J=16.0 Hz), 6.01 (d, J=15.8 Hz), 6.77 (dd, J=15.6, 6.0 Hz), 6.89 (dd, J=15.8,6.0 Hz),7.16–7.34 (m), 8.09 (d, J=8.0 Hz), 8.43 (d, J=8.0 Hz), 8.63 (s), 8.68 (s), 8.70 (d, J=7.0 Hz).

Preparation of Product Ethyl-3-(Benzylthiocarbonyl-L-Leu-L-N-Me-Ph-L-Gln)-E-Propenoate.

Using the procedure described in Example 4 for the preparation of ethyl-3-(cyclopentylthiocarbonyl-L-Leu-L-N-Me-Phe-L-Gln)-E-propenoate, ethyl-3-(benzylthiocarbonyl-L-Leu-L-N-Me-Phe-L-Gln)-E-propenoate was synthesized from ethyl-3-(benzylthiocarbonyl-L-Leu-L-N-Me-Phe-L-(Tr-Gln)-E-propenoate in 41% yield (two steps from the aldehyde intermediate): white amorphous solid: mp=60–63° C.): IR(KBr) 3289, 2957, 1638, 1533, 1453, 1277, 1209, 700 cm$^{-1}$; $^1$H NMR (DMSO-d$_6$) (mixture of rotamers) δ -.026 (m), 0.60 (m), 0.83 (d, J=6.2 Hz), 1.17 (t, J=7.0 Hz), 1.20 (t, J=7.0 Hz), 1.03–1.60 (m), 1.66–1.98 (m), 2.01 (m), 2.80 (s), 2.92 (m), 2.96 (s), 3.25 (m), 3.92–4.18 (m), 4.38 (m), 4.48 (m), 4.68 (m), 4.86 (m), 5.08 (m), 5.69 (d, J=16.0 Hz), 5.99 (d, J=16.0 Hz), 6.69–6.76 (m), 6.86 (dd, J=16.0, 6.0 Hz), 7.14–7.29 (m), 8.00 (m), 8.36 (d, J=8.5 Hz), 8.64 (d, J=6.6 Hz). HRMS calcd for $C_{33}H_{44}N_4O_6S$+Cs 757.2036, found 757.2008. Anal. ($C_{33}H44N_4O_6S$) C, H, N.

Example 15

Preparation of Compound 16: Ethyl-2-Methyl-3-(Benzylthiocarbonyl-L-Leu-L-N-Me-Phe-L-Gln)-E-Propenoate.

Preparation of Intermediate Ethyl-2-Methyl-3-[Benzylthiocarbonyl-L-Leu-L-N-Me-Phe-L-(Tr-Gln)]-E-Propenoate.

Using the procedure described in Example 4 for the preparation of ethyl-3-[cyclopentylthiocarbonyl-L-Leu-L-N-Me-Phe-L-(Tr-GIn)]-E-propenoate, ethyl-2-methyl-3-[benzylthiocarbonyl-L-Leu-L-N-Me-Phe-L-(Tr-Gln)]-E-propenoate was synthesized from benzylthiocarbonyl-L-Leu-L-N-Me-Phe-L-(Tr-glutaminal) (0.2 g, 0.25 mmol) and (carbethoxyethylidene) triphenylphosphorane (0.11 g, 0.3 mmol) in 5 mL THF to give 0.12 g of material contaminated with triphenylphosphine oxide after column chromatography on silica gel (gradient; 0–1% MeOH/CHCl$_3$) which was used without further purification. White amorphous solid: $^1$H NMR (DMSO-d$_6$) (mixture of rotamers) δ −.012 (m), 0.61 (m), 0.80 (d, J=6.2 Hz), 1.10–1.34 (m), 1.38–1.74 (m), 1.76 (s), 1.81 (s), 2.10–2.48 (m), 2.83 (s), 2.94 (s), 3.13 (m), 3.85 (d, J=14.0 Hz), 3.98 (d, J=14.0 Hz), 4.02 (s), 4.09 (m), 4.35 (m), 4.57 (m), 4.73 (m), 4.97 (m), 6.38 (d, J=10.0 Hz), 6.53 (d, J=9.0 Hz), 7.10–7.28 (m), 7.98 (m), 8.35 (d, J=8.0 Hz), 8.51 (s), 8.58 (s), 8.63 (d, J=6.0 Hz).

Preparation of Product Ethyl-2-Methyl-3-(Benzylthiocarbonyl-L-Leu-L-N-Me-Phe-L-Gln)-E-Propenoate.

Using the procedure described in Example 4 for the preparation of ethyl-3-(cyclopentylthiocarbonyl-L-Leu-L-N-Me-Phe-L-Gln)-E-propenoate, ethyl-2-methyl-3-(benzylthiocarbonyl-L-Leu-L-N-Me-Phe-L-Gln)-E-propenoate was synthesized from ethyl-2-methyl-3-[benzylthiocarbonyl-L-Leu-L-N-Me-Phe-L-(Tr-Gln)]-E-propenoate in 24% yield (two steps from the aldehyde intermediate). White amorphous solid: $^1$H NMR (DMSO-d$_6$) (mixture of rotamers) δ −0.16 (m), 0.59 (m), 0.84 (m), 1.08–1.83 (m), 1.78 (s), 1.86 (s), 2.03 (m), 2.79 (s), 2.94 (s), 3.16 (m), 3.97–4.21 (m), 4.35 (m), 4.53–4.78 (m), 5.08 (m), 6.39 (d, J=9.0 Hz), 6.55 (d, J=9.0 Hz), 6.82 (m), 7.12–7.29 (m), 7.96 (m), 8.35 (d, J=6.6 Hz), 8.65 (d, J=7.0 Hz). HRMS calcd for C$_{34}$H$_{46}$N$_4$O$_6$S+Cs 771.2192, found 771.2172. Anal. (C$_{34}$H$_{46}$N$_4$O$_6$S) C, H, N.

Example 16

Preparation of Compound 17: 1-[2'-Oxazolidon-3'-yl]-3-(Ethylthiocarbonyl-L-Leu-L-N-Me-Phe-L-Gln)-E-Propepone.

Preparation of Intermediate 1-[2'-Oxazolidon-3'-yl]-3-[BOC-L-(Tr-Gln)]-E-Propenone.

To 3-[BOC-L-(Tr-Gln)]-E-propenoic acid (1.0 g, 1.94 mmol) in 12.0 mL of anh THF was added triethylamine (0.68 mL, 4.86 mmol). The mixture was cooled to −20° C. and pivaloyl chloride (0.24 mL, 1.94 mmol) was added. The reaction mixture was stirred at −20° C. for 2.5 h, at which time solid lithium chloride (0.091 g, 2.14 mmol) and 2-oxazolidone (0.17 g, 1.94 mmol) were added. The reaction mixture was allowed to warm to rt and further stirred overnight. The mixture was then concentrated to dryness, and the residue was taken up in CH$_2$Cl$_2$ and washed with 5% KHSO$_4$. The organic layer was separated, and the aqueous layer was reextracted twice with CH$_2$Cl$_2$. The combined organic layers were dried over MgSO$_4$, concentrated and purified by column chromatography on silica gel (5% MeOH/CHCl$_3$) to yield 1-[2'-oxazolidon-3'-yl]-3-[BOC-L-(Tr-Gln)]-E-propenone (0.61 g, 54%) as an off-white solid foam. $^1$H NMR (CDCl$_3$) δ 1.23 (s, 4.5 H), 1.43 (s, 4.5 H), 1.81 (m, 1H), 1.98 (m, 1H), 2.40 (t, 2H, J=7.2 Hz), 4.02–4.08 (m, 2H), 4.37–4.44 (m, 3H), 4.88 (d, 1H, J=8.1 Hz), 6.87 (bs, 1H), 6.99 (dd, 1H, J=15.8, 5.2 Hz), 7.18–7.32 (m, 16H). MS calcd for C$_{34}$H$_{37}$N$_3$O$_6$+H 584, found 584.

Preparation of Intermediate 1-[2'-Oxazolidon-3'-yl]-3-[BOC-L-Leu-L-N-Me-Phe-(Tr-Gln)]-E-Propenone.

To 1-[2'-oxazolidon-3'-yl]-3-[BOC-L-(Tr-Gln)]-E-propenone (0.60 g, 1.02 mmol) dissolved in isopropyl alcohol (17.25 mL), HClO$_4$ (5.0 mL, 79.63 mmol) was added, and the reaction mixture was stirred at rt for 1.5 h. The mixture was then poured into an aq solution of 1N NaOH (3.0 mnL) along with a sat. NaHCO$_3$ solution (30.0 mL) and was extracted twice with CH$_2$Cl$_2$. The organic phase was dried over MgSO$_4$ and concentrated to give the free amine (0.46 g, 0.96 mmol), which was coupled immediately with BOC-L-Leu-L-N-Me-Phe (0.38 g, 0.96 mmol) using the procedure described in Example 1 for the preparation of ethyl-3-[BOC-L-N-Me-Phe-L-(Tr-Gln)]-E-propenoate to provide 1-[2'-oxazolidon-3'-yl]-3-[BOC-L-Leu-L-N-Me-Phe-(Tr-Gln)]-E-propenone (0.33 g, 41%) as a tan solid foam after column chromatography on silica (2% methanol/CHCl$_3$). $^1$H NMR (CDCl$_3$) δ 0.65 (t, J=6.8 Hz), 0.72 (m), 0.84–0.89 (m), 1.07 (m), 1.24–1.44 (m), 1.63 (m), 1.84 (m), 2.08 (m), 2.28–2.36 (m), 2.90 (s), 3.01 (m), 3.34 (m, 4.01–4.06 (m), 4.16 (m), 4.38–4.42 (m), 4.64 (m), 4.73 (m), 4.85 (m), 6.76 (bs), 7.04 (dd, J=15.5, 6.1 Hz), 7.12–7.41 (m), 8.29 (d, J=8.4 Hz). MS calcd for C$_{50}$H$_{59}$N$_5$O$_8$+H 858, found 858.

Preparation of Intermediate 1-[2'-Oxazolidon-3'-yl]-3-[Ethylthiocarbonyl-L-Leu-L-N-Me-Phe-(Tr-Gln)]-E-Propenone.

1-[2'-Oxazolidon-3'-yl]-3-[BOC-L-Leu-L-N-Me-Phe-(Tr-Gln)]-E-propenone (0.32 g, 0.37 mmol) was deprotected with HClO$_4$ using the procedure described in the previous preparation and was subsequently coupled to ethylchlorothiolformate (0.042 mL, 0.40 mmol) using the procedure described in Example 6 for the preparation of 2,3-chhydroindole-3-[ethylthiocarbonyl-L-Leu-L-N-Me-Phe-L-(Tr-Gln)]-E-propenamide to provide 1-[2'-oxazolidon-3'-yl]-3-[ethylthiocarbonyl-L-Leu-L-N-Me-Phe-(Tr-Gln)]-E-propenone (0.22 g, 78%) as an off-white solid foam after column chromatography on silica (2% methanol/CHCl$_3$). $^1$H NMR (CDCl$_3$) δ 0.62–0.76 (m), 0.85–0.87 (m), 1.13–1.26 (m), 1.37 (m), 1.62 (m), 1.85 (m), 2.06 (m), 2.58–2.72 (m), 2.67–2.89 (m), 3.18–3.40 (m), 4.02–4.07 (m), 4.39–4.44 (m), 4.64–4.67 (m), 5.71 (m), 6.76 (bs), 7.00 (m), 7.14–7.35 (m), 8.06 (d, J=8.4 Hz). MS calcd for C$_{48}$H$_{55}$N$_5$O$_7$S+Cs 978, found 978.

Preparation of Product-1-[2'-Oxazolidon-3'-yl]-3-(Ethylthiocarbonyl-L-Leu-L-N-Me-Phe-Gln)-E-Propenone.

1-[2'-Oxazolidon-3'-yl]-3-[ethylthiocarbonyl-L-Leu-L-N-Me-Phe-(Tr-Gln)]-E-propenone (0.22 g, 0.26 mmol) was deprotected using the procedure described in Example 1 for the preparation of ethyl-3-(CBZ-L-N-Me-Phe-L-Gln)-E-propenoate to provide 1-[2'-oxazolidon-3'-yl]-3-(ethylthiocarbonyl-L-Leu-L-N-Me-Phe-Gln)-E-propenone (0.056 g, 35%) as a white solid: mp=110–111° C.; IR (thin film) 3272, 1677 cm$^{-1}$; $^1$H NMR (CDCl$_3$) δ 0.64–0.70 (m), 0.89–0.91 (m), 1.19–1.28 (m), 1.40 (m), 1.65 (m), 2.03 (m), 2.23–2.25 (m), 2.76–2.96 (m), 3.48 (q, J=7.2 Hz), 4.04–4.10 (m), 4.41–4.46 (m), 4.65–4.67 (m), 5.48 (m), 6.12 (m), 6.24 (bs), 7.02 (m), 7.15–7.36 (m), 7.91 (m). HRMS calcd for C$_{29}$H$_{41}$N$_5$O$_7$S+Cs 736.1780, found 736.1803; Anal (C$_{29}$H$_{41}$N$_5$O$_7$S) C, H, N.

Example 17

Preparation of Compound 18: Ethyl-3-[CBZ-L-Leu-L-(3R-Phenyl)-Pro-L-Gln]-E-Propenoate.

Preparation of Intermediate BOC-L-(3R-Phenyl)-Pro.

(2S, 3R)-3-Phenylpyrrolidine-2-carboxylic acid (0.10 g, 0.52 mmol) was suspended in 1,4-dioxane and 800 mL of 1N NaOH was added to form a clear solution. Di-tert-butyl dicarbonate (0.13 g, 0.58 mmol) was added over a period of 30 minutes, and the reaction mixture was stirred overnight at rt. At this time, the reaction mixture was concentrated in vacuo, and the resulting residue was taken up in a saturated solution of $NaHCO_3$. This solution was washed with ether, and the aqueous layer was acidified with 1N HCl and extracted with ethyl acetate. The organic phase was separated and dried over $MgSO_4$ and concentrated to provide BOC-L-(3R-phenyl)-Pro (0.15 g, 97%) as a white solid. $^1H$ NMR ($CDCl_3$) δ 1.52 (s, 9H), 2.03 (m, 1H), 2.35 (m, 1H), 3.49–3.83 (m, 4H), 7.33–7.35 (m, 5H). MS calcd for $C_{16}H_{21}NO_4$+H 292, found 292.

Preparation of Intermediate Ethyl-3-[BOC-L-(3R-Phenyl)-Pro-L-(Tr-Gln)]-E-Propenoate.

Ethyl-3-[BOC-L-(Tr-Gln)]-E-propenoate (0.28 g, 0.52 mmol) was deprotected and coupled to BOC-L-(3R-phenyl)-Pro using the procedure described in Example 1 for the preparation of ethyl-3-[BOC-L-N-Me-Phe-L-(Tr-Gln)]-E-propenoate, to provide ethyl-3-[BOC-L-(3R-phenyl)-Pro-L-(Tr-Gln)]-E-propenoate (0.27 g, 73%) as a white glassy solid after column chromatography on silica (2% methanol/$CHCl_3$). $^1H$ NMR ($CDCl_3$) δ 1.25–1.31 (m, 3H), 1.40 (bs, 9H), 2.03 (m, 2H), 2.41 (m, 2H), 3.48 (m, 2H), 3.67 (m, 2H), 4.14–4.21 (m, 4H), 4.68 (m, 1H), 5.62 (d, 1H, J=16.5 Hz), 6.32 (m, 1H), 6.75 (dd, 1H, J=15.9, 5.0 Hz), 6.96 (s, bs, 1H), 7.20–7.33 (m, 20H). MS calcd for $C_{44}H_{49}N_3O_6$+H 716, found 716.

Preparation of Intermediate-Ethyl-3-[CBZ-L-Leu-L-(3R-Phenyl)-Pro-L-(Tr-Gln)]-E-Propenoate.

Ethyl-3-[BOC-L-(3R-phenyl)-Pro-L-(Tr-Gln)]-E-propenoate was deprotected and coupled to CBZ-Leu (0.10 g, 0.37 mmol) using the procedure described in Example 1 for the preparation of ethyl-3-[BOC-L-N-Me-Phe-L-(Tr-Gln)]-E-propenoate, to provide ethyl-3-[CBZ-L-Leu-L-(3R-phenyl)-Pro-L-(Tr-Gln)]-E-propenoate (0.19 g, 60%) as a white glassy solid. $^1H$ NMR ($CDCl_3$) δ 0.84 (d, 3H, J=6.5 Hz), 0.93 (d, 3H, J=6.5 Hz), 1.94 (m, 1H), 1.29 (t, 3H, J=7.2 Hz), 1.34–1.51 (m, 2H), 2.07 (m, 1H), 2.23 (m, 1H), 2.37 (m, 1H), 2.44–2.48 (m, 2H), 3.50–3.52 (m, 2H), 3.67–3.69 (m, 2H), 4.04–4.19 (m, 4H), 4.45–4.52 (m, 2H), 4.80 (d, 1H, J=9.0 Hz), 5.05 (d, 1H, J=12.1 Hz), 5.12 (d, 1H, J=12.1 Hz), 5.44 (dd, 1H, J=15.6, 1.9 Hz), 5.65 (d, 1H, J=8.7 Hz), 6.66 (dd, 1H, J=15.7, 4.5 Hz), 7.17–7.38 (m, 25H); MS calcd for $C_{53}H_{58}N_4O_7$+H 863, found 863.

Preparation of Product-Ethyl-3-[CBZ-L-Leu-L-(3R-Phenyl)-Pro-L-Gln]-E-Propenoate.

Ethyl-3-[CBZ-L-Leu-L-(3R-phenyl)-Pro-L-(Tr-Gln)]-E-propenoate was deprotected using the procedure described in Example 1 for the preparation of ethyl-3-(CBZ-L-N-Me-Phe-L-Gln)-E-propenoate, to provide ethyl-3-[CBZ-L-Leu-L-(3R-phenyl)-Pro-L-Gln]-E-propenoate (0.098 g, 70%) as a white solid after column chromatography on silica (5% methanol/$CHCl_3$). mp=72–75° C.; IR (thin film) 3311, 1709cm$^{-1}$; $^1H$ NMR ($CDCl_3$) δ 0.97 (t, 6H, J=7.2Hz), 1.30 (t, 3H, J=7.0 Hz), 1.44–1.57 (m, 4H), 1.75 (m, 1H), 2.10 (m, 1H), 2.17–2.28 (m, 2H), 2.34–2.43 (m, 2H), 3.51 (m, 1H), 3.73 (m, 1H), 4.13–4.20 (m, 3H), 4.59–4.66 (m, 2H), 5.11 (bs, 2H), 5.25 (bs, 1H), 5.37–5.47 (m, 2H), 5.71 (d, 1H, J=9.0 Hz), 6.57 (bs, 1H), 6.70 (dd, 1H, J=15.7, 4.5 Hz), 7.25–7.41 (m, 10H). HRMS calcd for $C_{34}H_{44}N_4O_7$+Cs 753.2264, found 753.2240. Anal ($C_{34}H_{44}N_4O_7$) C, H, N.

Example 18

Preparation of Compound 19: Ethyl-3-(CBZ-L-Leu-L-Pro-L-Gln)-E-Propenoate,

Preparation of Intermediate Ethyl-3-[BOC-L-Pro-L-(Tr-Gln)]-E-Propenoate.

Ethyl-3-[BOC-L-(Tr-Gln)]-E-propenoate (0.30 g, 0.55 mmol) was deprotected and coupled to BOC-L-Pro (0.11 g, 0.55 mmol) using the procedure described in Example 1 for the preparation of ethyl-3-[BOC-L-N-Me-Phe-L-(Tr-Gln)]-E-propenoate, to provide ethyl-3-[BOC-L-Pro-L-(Tr-Gln)]-E-propenoate (0.30 g, 85%) as a white glassy solid after column chromatography on silica (5% methanol/$CHCl_3$). $^1H$ NMR ($CDCl_3$) δ 1.27 (t, 3H, J=7.2 Hz), 1.43 (bs, 10H), 1.82–2.00 (m, 6H), 2.34 (t, 2H, J=7.2 Hz), 3.34 (m, 2H), 4.14–4.21 (m, 3H), 4.62 (m, 1H), 5.92 (dd, 1H, J=15.6, 1.5 Hz), 6.80 (dd, 1H, J=15.7, 5.1 Hz), 7.18–7.33 (m, 16H). MS calcd for $C_{38}H_{45}N_3O_6$+Cs 772, found 772.

Preparation of Intermediate Ethyl-3-[CBZ-L-Leu-L-Pro-L-(Tr-Gln)]-E-Propenoate.

Ethyl-3-[BOC-L-Pro-L-(Tr-Gln)]-E-propenoate (0.30 g, 0.47 mmol) was deprotected and coupled with CBZ-Leu (0.12 g, 0.47 mmol) using the procedure described in Example 1 for the preparation of ethyl-3-[BOC-L-N-Me-Phe-L-(Tr-Gln)]-E-propenoate, to provide ethyl-3-[CBZ-L-Leu-L-Pro-L-(Tr-Gln)]-E-propenoate (0.24 g, 64%) as a white foamy solid after column chromatography on silica (2% methanol/$CHCl_3$). $^1H$ NMR ($CDCl_3$) δ 0.84 (d, 3H, J=6.5 Hz), 0.92 (d, 3H, J=6.2 Hz), 1.27 (t, 3H, J=7.0 Hz) 1.35 (m, 1H), 1.63–1.75 (m, 2H), 1.99–2.10 (m, 5H), 2.39 (m, 2H), 3.53 (m, 1H), 3.73–3.76 (m, 3H), 4.17 (q, 2H, J=7.2 Hz), 4.26 (m, 1H), 4.49–4.51 (m, 3H), 5.02–5.12 (m, 3H), 5.85 (dd, 1H, J=15.9, 1.6 Hz), 6.78 (dd, 1H, J=15.7, 5.1 Hz), 7.07 (bs, 1H), 7.19–7.33 (m, 20H). MS calcd for $C_{47}H_{54}N_4O_7$+Cs 919, found 919.

Preparation of Product-Ethyl-3-(CBZ-L-Leu-L-Pro-L-Gln)-E-Propenoate.

Ethyl-3-[CBZ-L-Leu-L-Pro-L-(Tr-Gln)]-E-propenoate (0.22 g, 0.28 mmol) was deprotected using the procedure described in Example 1 for the preparation of ethyl-3-(CBZ-L-N-Me-Phe-L-Gln)-E-propenoate, to provide ethyl-3-(CBZ-L-Leu-L-Pro-L-Gln)-E-propenoate (0.092 g, 61%) as a white solid after preparative TLC (10% methanol/$CHCl_3$): mp=55–60° C.; IR (thin film) 3300, 1707 cm$^{-1}$; $^1H$ NMR ($CDCl_3$) δ 0.94 (d, 3H, J=6.5 Hz), 0.98 (d, 3H, J=6.5 Hz) 1.28 (t, 3H, J=7.2 Hz), 1.46 (t, 2H, J=7.0 Hz), 1.70–1.75 (m, 2H), 2.03–2.33 (m, 7H), 3.60 (m, 1H), 3.79 (m, 1H), 4.19 (q, 2H, J=7.2 Hz), 4.41 (m, 1H), 4.54–4.65 (m, 2H), 5.08 (dd, 2H, J=15.4, 12.3 Hz), 5.54 (m, 1H), 5.44 (d, 1H, J=8.4 Hz), 5.91 (dd, 1H, J=15.7, 1.4 Hz), 6.36 (m, 1H), 6.77 (d, 1H, J=8.7 Hz), 6.84 (dd, 1H, J=15.9, 5.0 Hz), 7.34 (bs, 5H). HRMS calcd for $C_{28}H_{40}N_4O_7$+Cs 677.1951, found 677.1972. Anal ($C_{28}H_{40}N_4O_7$·0.5$H_2O$) C, H, N.

Example 19

Preparation of Compound 20: Ethyl-3-[CBZ-L-Leu-L-(4R-Benzyloxy)-Pro-L-Gln]-E-Propenoate.

Preparation of Intermediate Ethyl-3-[BOC-L-(4R-Benzyloxy)-Pro-L-(Tr-Gln)]-E-Propenoate.

Ethyl-3-[BOC-L-(Tr-Gln)]-E-propenoate (0.50 g, 0.92 mmol) was deprotected and coupled to BOC-L-(4R-benzyloxy)-Pro (0.30 g, 0.92 mmol) using the procedure described in Example 1 for the preparation of ethyl-3-[BOC-L-N-Me-Phe-L-(Tr-Gln)]-E-propenoate to provide ethyl-3-[BOC-L-(4R-benzyloxy)-Pro-L-(Tr-Gln)]-E-propenoate (0.54 g, 78%) as a white foamy solid after column chromatography on silica (2% methanol/$CHCl_3$). $^1H$ NMR ($CDCl_3$)

δ 1.27 (t, 3H, J=7.16 Hz), 1.39 (bs, 10H), 1.80 (m, 1H), 1.80 (m, 1H), 2.16 (m, 1H), 2.32–2.39 (m, 2H), 3.46–3.51 (m, 2H), 4.18 (q, 2H, J=7.2 Hz), 4.26–4.35 (m, 2H), 4.46–4.49 (m, 2H), 4.56–4.66 (m, 2H), 5.90 (dd, 1H, J=15.7 Hz), 6.80 (dd, 1H, J=15.6, 4.8 Hz), 6.97 (m, 1H), 7.18–7.37 (m, 20H). MS calcd for $C_{45}H_{51}N_3O_7$+H 746, found 746.

Preparation of Intermediate Ethyl-3-[CBZ-L-Leu-L-(4R-Benzyloxy)-Pro-L-(Tr-Gln)]-E-Propenoate.

Ethyl-3-[BOC-L-(4R-benzyloxy)-Pro-L-(Tr-Gln)]-E-propenoate (0.49 g, 0.72 mmol) was deprotected and coupled to CBZ-Leu (0.19 g, 0.72 mmol) using the procedure described in Example 1 for the preparation of ethyl-3-[BOC-L-N-Me-Phe-L-(Tr-Gln)]-E-propenoate, to provide ethyl-3-[CBZ-L-Leu-L-(4R-benzyloxy)-Pro-L-(Tr-Gln)]-E-propenoate (0.47 g, 72%) as a white foamy solid after column chromatography on silica (2% methanol/CHCl$_3$). $^1$H NMR (CDCl$_3$) δ 0.84 (d, 3H, J=6.5 Hz), 0.91 (d, 3H, J=6.5 Hz), 1.29–1.35 (m, 4H), 1.75 (m, 1H), 2.45 (m, 1H), 2.19–2.23 (m, 2H), 2.40–2.46 (m, 2H), 3.60 (m, 1H), 3.87 (m, 1H), 4.18 (q, 2H, J=7.2 Hz), 4.27–4.37 (m, 2H), 4.48–4.54 (m, 5H), 4.97–5.09 (m, 4H), 5.83 (dd, 1H, J=15.7, 1.7 Hz), 6.673 (d, 1H, J=7.5 Hz), 6.78 (dd, 1H, J=15.7, 5.1 Hz), 7.09 (bs, 1H), 7.15–7.36 (m, 25H). MS calcd for $C_{54}H_{60}N_4O_8$+H 893, observed 893.

Preparation of Product-Ethyl-3-[CBZ-L-Leu-L-(4R-Benzyloxy)-Pro-L-Gln]-E-Propenoate.

Ethyl-3-[CBZ-L-Leu-L-(4R-benzyloxy)-Pro-L-(Tr-Gln)]-E-propenoate (0.47 g, 0.52 mmol) was deprotected using the procedure described in Example 1 for the preparation of ethyl-3-(CBZ-L-N-Me-Phe-L-Gln)-E-propenoate, to provide ethyl-3-[CBZ-L-Leu-L-(4R-benzyloxy)-Pro-L-Gln]-E-propenoate (0.27 g, 81%) as a white foamy solid after column chromatography on silica (5% methanol/CHCl$_3$). IR (thin film) 3296, 1716 cm$^{-1}$; $^1$H NMR (CDCl$_3$) δ 0.90–0.96 (m, 6H), 1.28 (t, 3H, J=7.0 Hz), 1.44–1.46 (m, 2H), 1.69–1.71 (m, 2H), 2.07–2.37 (m, 5H), 3.67 (dd, 1H, J=10.7, 4.5 Hz), 4.03 (d, 1H, J=10.9Hz), 4.16 (d, 1H, J=7.2 Hz), 4.21 (d, 1H, J=7.2 Hz), 4.32 (m, 1H), 4.46–4.55 (m, 4H), 4.62 (m, 1H), 5.02 (d, 1H, J=12.3 Hz), 5.09 (d, 1H, J=12.3 Hz), 5.31 (m, 1H), 5.46 (d, 1H, J=9.0 Hz), 5.89 (dd, 1H, J=15.9, 1.6 Hz), 6.43 (m, 1H), 6.65 (d, 1H, J=9.0 Hz), 6.83 (dd, 1H, J=15.7, 5.1 Hz), 7.33 (bs, 10H). HRMS calcd for $C_{35}H_{46}N_4O_8$+Cs 783.2370, found 783.2390; Anal ($C_{35}H_{46}N_4O_8$·0.5 H$_2$O) C, H, N.

Example 20

Preparation of Compound 21: Ethyl-3-[CBZ-L-Leu-L-(3S-Methyl)-Pro-L-Gln]-E-Propenoate.

Preparation of Intermediate BOC-L-(3S-Methyl)-Pro.

(2S, 3S)-3-Methyl pyrrolidine-2-carboxylic acid (0.25 g, 1.94 mmol) was protected with a BOC group following the procedure described in Example 17 for the preparation of BOC-L-(3R-Phenyl)-Pro to provide BOC-L-(3S-methyl)-Pro (0.43 g, 98%) as a white solid. $^1$H NMR (CDCl$_3$) δ 1.16–1.21 (m, 6H), 1.42 (s, 9H), 1.48 (s, 9H), 1.52–1.61 (m, 2H), 2.01–2.12 (m, 2H), 2.41 (m, 1H), 2.61 (m, 1H), 3.41–3.62 (m, 4H), 3.77 (m, 1H), 3,90 (m, 1H). MS calcd for $C_{11}H_{19}NO_4$+H, 230, found 230.

Preparation of Intermediate Ethyl-3-[BOC-L-(3S-Methyl)-Pro-L-(Tr-Gln)]-E-Propenoate.

Ethyl-3-[BOC-L-(Tr-Gln)]-E-propenoate (0.53 g, 0.97 mmol) was deprotected and coupled to BOC-L-(3S-methyl)-Pro (0.22 g, 0.97 mmol) using the procedure described in Example 1 for the preparation of ethyl-3-[BOC-L-N-Me-Phe-L-(Tr-Gln)]-E-propenoate, to provide ethyl-3-[BOC-L-(3S-methyl)-Pro-L-(Tr-Gln)]-E-propenoate (0.27 g, 43%) as a glassy off-white solid foam after column chromatography on silica (5% methanol/CHCl$_3$). $^1$H NMR (CDCl$_3$) δ 1.10–1.17 (m, 3H), 1.27 (t, 3H, J=7.2 Hz), 1.41 (bs, 10H), 1.58 (bs, 2H), 1.80 (m, 1H), 2.00 (m, 1H), 2.36 (m, 2H), 3.30 (m, 1H), 3.40–3.66 (m, 2H), 3.70 (d, 1H, J=5.0 Hz), 4.14–4.21 (m, 2H), 4.64 (m, 1H), 5.92 (d, 1H, J=15.9 Hz), 6.78–6.84 (m, 2H), 7.19–7.29 (m, 15H). MS calcd for $C_{39}H_{47}N_3O_6$+H, 654, found 654.

Preparation of Intermediate Ethyl-3-[CBZ-L-Leu-L-(3S-Methyl)-Pro-L-(Tr-Gln)]-E-Propenoate.

Ethyl-3-[BOC-L-(3S-methyl)-Pro-L-(Tr-Gln)]-E-propenoate (0.27 g, 0.42 mmol) was deprotected and coupled to CBZ-Leu (0.11 g, 0.42 mmol) using the procedure described in Example 1 for the preparation of ethyl-3-[BOC-L-N-Me-Phe-L-(Tr-Gln)]-E-propenoate, to provide ethyl-3-[CBZ-L-Leu-L-(3S-methyl)-Pro-L-(Tr-Gln)]-E-propenoate (0.18 g, 52%) as a white solid foam after column chromatography on silica (4% methanol/CHCl$_3$). $^1$H NMR (CDCl$_3$) δ 0.83 (d, 3H, J=6.2 Hz), 0.92 (d, 3H, J=6.2 Hz), 1.10 (d, 3H, J=7.2 Hz), 1.34 (m, 1H), 1.60–1.74 (m, 2H), 2.04–2.17 (m, 3H), 2.38–2.48 (m, 3H), 3.53 (m, 1H), 3.68 (d, 1H, J=6.2 Hz), 3.91 (m, 1H), 4.17 (dd, 2H, J=14.9, 6.8 Hz), 4.48–4.52 (m, 2H), 4.96–5.12 (m, 4H), 5.84 (d, 1H, J=15.6 Hz), 6.49 (d, 1H, J=8.1 Hz), 6.79 (dd, 1H, J=16.2, 4.7 Hz), 7.13 (bs, 1H), 7.19–7.33 (m, 20H). MS calcd for $C_{48}H_{56}N_4O_7$+H, 801, found 801.

Preparation of Product-Ethyl-3-[CBZ-L-Leu-L-(3S-Methyl)-Pro-L-Gln]-E-Propenoate.

Ethyl-3-[CBZ-L-Leu-L-(3S-methyl)-Pro-L-(Tr-Gln)]-E-propenoate (0.18 g, 0.22 mmol) was deprotected using the procedure described in Example 1 for the preparation of ethyl-3-(CBZ-L-N-Me-Phe-L-Gln)-E-propenoate, to provide ethyl-3-[CBZ-L-Leu-L-(3S-methyl)-Pro-L-Gln]-E-propenoate (0.078 g, 64%) as a white solid foam after column chromatography on silica (4% methanol/CHCl$_3$). IR (thin film) 3392, 1708 cm$^{-1}$; $^1$H NMR (CDCl$_3$) δ 0.92–0.98 (m, 6H), 1.17 (d, 3H, J=6.9 Hz), 1.28 (t, 3H, J=7.2 Hz), 1.41–1.49 (m, 2H), 1.64–1.76 (m, 3H), 2.10–2.28 (m, 3H), 2.35–2.48 (m, 2H), 3.59 (m, 1H), 3.85 (d, 1H, J=6.5 Hz), 3.96 (m, 1H), 4.19 (dd, 1H, J=14.3, 7.2 Hz), 4.54 (m, 1H), 4.68 (m, 1H), 5.04–5.13 (m, 2H), 5.31 (d, 1H, J=9.0 Hz), 5.91 (dd, 1H, J=15.6, 1.6 Hz), 6.51–6.54 (m, 2H), 6.85 (dd, 1H, J=15.7, 5.1 Hz), 7.34 (bs, 5H). HRMS calcd for $C_{29}H_{42}N_4O_7$+Na, 581.2951, found 581.2937. Anal ($C_{29}H_{42}N_4O_7$·0.5 H$_2$O) C, H, N.

Example 21

Preparation of Compound 22: N-Methoxy, N-Methyl-3-[CBZ-L-Leu L-(3R-Phenyl)-Pro-L-Gln]-E-Propenamide.

Preparation of Intermediate 3-[BOC-L-(Tr-Gln)]-E-Propenoic Acid.

Ethyl-3-[BOC-L-(Tr-Gln)]-E-propenoate (1.874 g, 3.46 mmol) was taken up in 20 mL EtOH, and 1N aq NaOH (7.95 mL, 7.95 mmol) was added dropwise via an addition funnel over 2 h. The resulting solution was stirred at room temperature for 1.5 h, whereupon the reaction mixture was poured into water and washed with ether. The aqueous layer was acidified to pH 3 with 1N HCl, and extracted 3 times with EtOAc. The organic phase was dried over MgSO$_4$ and concentrated to provide 3-[BOC-L-(Tr-Gln)]-E-propenoic acid (1.373 g, 77%) as a glassy off-white solid. No further purification was needed: IR (KBr) 3315, 1698, 1666 cm$^{-1}$; $^1$H NMR (CDCl$_3$) δ 1.42 (s, 9H), 1.76 (m, 1H), 1.83–1.98 (m, 1H), 2.37 (t, 2H, J=7.0 Hz), 4.30 (m, 1H), 4.88 (m, 1H), 5.85 (d, 1H, J=15.3 Hz), 6.86 (dd, 1H, J=15.5, 5.1 Hz), 6.92 (s, 1H), 7.25 (m, 15H).

Preparation of Intermediate N-Methoxy-N-Methyl-3-[BOC-L-(Tr-Gln)]-E-Propenamide.

This intermediate was prepared from 3-[BOC-L-(Tr-Gln)]-E-propenoic acid and N, O-dimethylhydroxylamine hydrochloride as described in Example 1 for the synthesis of intermediate BOC-L-(Tr-Gln)-N(OMe)Me. This intermediate can alternatively be prepared by the reaction of BOC-L-(Tr-glutaminal) with N-methoxyl-N-methyl-(2-triphenylphosphoranylidene)-acetamide in THF as described for the preparation of ethyl-3-[cyclopentylthiocarbonyl-L-Leu-L-N-Me-Phe-L-(Tr-Gln)]-E-propenoate, or by the reaction of BOC-L-(Tr-glutaminal) with the anion of diethyl (N-methoxy-N-methylcarbamoylmethyl)phosphonate as described in Example 6 for the preparation of 1-(2',3'-dihydroindolin-1-yl)-3-[BOC-L-(Tr-Gln)]-E-propenone. IR (thin film) 3307, 1704 cm$^{-1}$; $^1$H NMR (CDCl$_3$) δ 1.43 (s, 9H), 1.80 (m, 1H), 1.95 (m, 1H), 2.36–2.40 (m, 2H), 3.24 (s, 3H), 3.67 (s, 3H), 4.31 (m, 1H), 4.83 (m, 1H), 6.48 (d, 1H, J=15.6 Hz), 6.79 (dd, 1H, J=15.6, 5.6 Hz), 6.92 (m, 1H), 7.19–7.32 (m, 15H). HRMS calcd for C$_{33}$H$_{39}$N$_3$O$_5$+Cs, 690.1944, found 690.1967.

Preparation of Intermediate N-Methoxy-N-Methyl-3-[BOC-L-(3R-Phenyl)-Pro-L-(Tr-Gln)]-E-Propenamide.

N-Methoxy-N-methyl-3-[BOC-L-(Tr-Gln)]-E-propenamide (0.24 g, 0.49 mmol) was deprotected and coupled to BOC-L-(3R-phenyl)-Pro (0.14 g, 0.49 mmol) using the procedure described in Example 1 for the preparation of ethyl-3-[BOC-L-N-Me-Phe-L-(Tr-Gln)]-E-propenoate to provide N-methoxy-N-methyl-3-[BOC-L-(3R-phenyl)-Pro-L-(Tr-Gln)]-E-propenamide (0.22 g, 63%) as a white solid foam after column chromatography on silica (3% methanol/CHCl$_3$). $^1$H NMR (CDCl$_3$) δ 1.40 (s, 9H), 1.48 (m, 1H), 1.73 (m, 1H), 1.91–2.02 (m, 2H), 2.25 (m, 1H), 2.35–2.45 (m, 2H), 3.22 (s, 3H), 3.43–3.46 (m, 2H), 3.61–3.72 (m, 4H), 4.20 (m, 1H), 4.70 (m, 1H), 6.44 (m, 1H), 6.74 (m, 1H), 6.99 (m, 1H), 7.16–7.33 (m, 20H). MS calcd for C$_{44}$H$_{50}$N$_4$O$_6$+Na 753, found 753.

Preparation of Intermediate N-Methoxy-N-Methyl-3-[CBZ-L-Leu-L-(3R-Phenyl)-Pro L-(Tr-Gln)]-E-Propenamide.

N-Methoxy-N-methyl-3-[BOC-L-(3R-phenyl)-Pro-L-(Tr-Gln)]-E-propenamide (0.18 g, 0.26 mmol) was deprotected and coupled to CBZ-L-Leu (0.070 g, 0.26 mmol) using the procedure described in Example 1 for the preparation of ethyl-3-[BOC-L-N-Me-Phe-L-(Tr-Gln)]-E-propenoate, to provide N-methoxy-N-methyl-3-[CBZ-L-Leu-L-(3R-phenyl)-Pro-L-(Tr-Gln)]-E-propenamide (0.076 g, 33%) as a clear glass after column chromatography on silica (3% methanol/CHCl$_3$). $^1$H NMR (CDCl$_3$) δ 0.79–0.93 (m, 6H), 1.01 (m, 1H), 1.22 (m, 1H), 1.40 (m, 1H), 1.51–1.95 (m, 2H), 2.01 (m, 1H), 2.19 (m, 1H), 2.31–2.52 (m, 2H), 3.15–3.20 (m, 3H), 3.53–3.68 (m, 6H), 3.92 (m, 1H), 4.08 (m, 1H), 4.57 (m, 1H), 5.02–5.15 (m, 2H), 6.25–6.35 (m, 2H), 6.63 (m, 1H), 7.15–7.35 (m, 25H). MS calcd for C$_{53}$H$_{59}$N$_5$O$_7$+H 878, found 878.

Preparation of Product-N-Methoxy-N-Methyl-3-[CBZ-L-Leu-L-(3R-Phenyl)-Pro-L-Gln]-E-Propenamide.

N-Methoxy-N-methyl-3-[CBZ-L-Leu-L-(3R-phenyl)-Pro-L-(Tr-Gln)]-E-propenamide (0.076 g, 0.090 mmol) was deprotected using the procedure described in Example 1 for the synthesis of ethyl-3-(CBZ-L-N-Me-Phe-L-Gln)-E-propenoate, to provide N-methoxy-N-methyl-3-[CBZ-L-Leu-L-(3R-phenyl)-Pro-L-Gln]-E-propenamnide (12.0 mg, 21%) as a clear glass after column chromatography (5% methanol/CHCl$_3$). IR (thin film) 3290, 1708 cm$^{-1}$; $^1$H NMR (CDCl$_3$) δ 0.94 (d, 3H, J=6.5 Hz), 0.99 (d, 3H, J=6.7 Hz), 1.44–1.74 (m, 3H), 2.05 (m, 1H), 2.15–2.22 (m, 2H), 2.32 (m, 1H), 2.41 (m, 1H), 3.21 (m, 1H), 3.51–3.74 (m, 5H), 4.14 (m, 1H), 4.23 (m, 1H), 4.62–4.66 (m, 2H), 5.09–5.10 (m, 2H), 5.27 (m, 1H), 5.48 (d, 1H, J=13.8 Hz), 6.17 (d, 1H, J=9.0 Hz), 6.36 (d, 1H, J=15.3 Hz), 6.59 (m, 1H), 6.65 (dd, 1H, J=15.6, 5.9 Hz), 7.21 (m, 1H), 7.24–7.35 (m, 10H). HRMS calcd for C$_{34}$H$_{45}$N$_5$O$_7$+Cs 768.2373, found 768.2395.

Example 22

Preparation of Compound 24: Ethyl-3-(Ethythiocarbonyl-L-Leu-L-Pro-L-Gln)-E-Propenoate.

Preparation of Intermediate Ethyl-3-[BOC-L-Leu-L-Pro-L-(Tr-Gln)]-E-Propenoate.

A solution of HCl in 1,4-dioxane (4.5 mL of a 4.0 M solution) was added to a solution of ethyl-3-[BOC-L-Pro-L-(Tr-Gln)]-E-propenoate (0.39 g, 0.61 mmol) in the same solvent (4.5 mL) at room temperature. The reaction mixture was stirred for 2 h at rt and then concentrated. The resulting foamy solid was dissolved in dry CH$_2$Cl$_2$, and BOC-L-Leu (0.14 g, 0.61 mmol), 1-hydroxybenzotriazole hydrate (0.12 g, 0.92 mmol), 4-methylmorpholine (0.27 mL, 2.45 mmol), and 1-(3-dimethylaminopropyl)-3-ethyl-carbodiimide hydrochloride (0.18 g, 0.92 mmol) were added sequentially. The reaction mixture was stirred for 12 h at 23° C., and then it was partitioned between 1N HCl and CH$_2$Cl$_2$. The organic layer was washed with aq sat solution of NaHCO$_3$, dried over MgSO$_4$, concentrated, and purified by column chromatography on silica gel (2% MeOH/CHCl$_3$) to provide ethyl-3-[BOC-L-Leu-L-Pro-L-(Tr-Gln)]-E-propenoate (0.31 g, 68%) as a foamy white solid. $^1$H NMR (CDCl$_3$) δ 0.84 (d, 3H, J=6.5 Hz), 0.92 (d, 3H, J=6.5 Hz), 1.27 (t, 3H, J=7.2 Hz), 1.43 (s, 9H), 1.63–1.72 (m, 3H), 1.97–2.09 (m, 6H), 3.52 (m, 1H), 3.75 (m, 1H), 4.14–4.21 (m, 2H), 4.27 (m, 1H), 4.42–4.52 (m, 2H), 4.86 (m, 1H), 5.85 (dd, 1H, J=15.6, 1.6 Hz), 6.75–6.82 (m, 2H), 7.07 (s, 1H), 7.19–7.32 (m, 15H). MS calcd for C$_{44}$H$_{56}$N$_4$O$_7$+Cs 885, found 885.

Preparation of Intermediate Ethyl-3-(Ethylthiocarbonyl-L-Leu-L-Pro-L-(Tr-Gln)]-E-Propenoate.

A solution of anh HCl in 1,4-dioxane (3.0 mL of a 4.0 M solution) was added to a solution of ethyl-3-[BOC-L-Leu-L-Pro-L-(Tr-Gln)]-E-propenoate (0.31 g, 0.42 mmol) in 3 mL 1,4-dioxane at 23° C. The reaction mixture was stirred for 2 h at 23° C., and it was then concentrated. The resulting foamy white solid was dissolved in dry CH$_2$Cl$_2$ and diisopropylethylamine (0.16 mL, 0.91 mmol), and ethylchlorothiolformate (0.052 mL, 0.91 mmol) were added sequentially. The reaction mixture was poured into H$_2$O, extracted with CH$_2$Cl$_2$ twice, and dried over MgSO$_4$. The solution was concentrated and purified by column chromatography on silica gel (2% MeOH/CHCl$_3$) to provide ethyl-3-[ethylthiocarbonyl-L-Leu-L-Pro-L-(Tr-Gln)]-E-propenoate (0.24 g, 78%) as a glassy white foamy solid. $^1$H NMR (CDCl$_3$) δ 0.83 (d, 3H, J=6.7 Hz), 0.91 (d, 3H, J=6.7 Hz), 1.27 (t, 6H, J=7.4 Hz), 1.34 (m, 1H), 1.70–1.72 (m, 2H), 1.96–2.10 (m, 6H), 2.37–2.42 (m, 2H), 2.88 (dd, 2H, J=14.6, 7.5 Hz), 3.54 (m, 1H), 3.72 (m, 1H), 4.18 (dd, 2H, J=14.3, 7.2 Hz), 4.25 (m, 11H), 4.52 (m, 1H), 4.75 (m, 1H), 5.78 (m, 1H), 5.85 (dd, 1H, J=15.8, 1.8 Hz), 6.79 (dd, 1H, J=15.8, 5.2 Hz), 6.88 (d, 1H, J=8.1 Hz), 7.11 (s, 1H), 7.20–7.33 (m, 15H). MS calcd C$_{42}$H$_{52}$N$_4$O$_6$S+Cs 873, found 873.

Preparation of Product-Ethyl-3-(Ethylthiocarbonyl-L-Leu-L-Pro-L-Gln)-E-Propenoate.

Trifluoroacetic acid (2.0 mL) was added to a solution of ethyl-3-[ethylthiocarbonyl-L-Leu-L-Pro-L-(Tr-Gln)]-E-propenoate (0.24 g, 0.32 mmol) in chloroform (2.0 mL) and stirred at 23° C. for 1 h. The yellow solution evaporated to dryness, and the residue was purified by column chromatography on silica gel (5% MeOH/CHl$_3$) to provide ethyl-3-(ethylthiocarbonyl-L-Leu-L-Pro-L-Gln)-E-propenoate (0.096 g, 60%) as a glassy white foamy solid. IR (thin film) 3292, 1717 cm$^{-1}$; $^1$H NMR (CDCl$_3$) δ 0.92 (d, 3H, J=6.5), 0.98 (d, 3H, J=6.7 Hz), 1.29 (t, 6H, J=7.4 Hz), 1.46–1.51 (m, 2H), 1.69–1.79 (m, 3H), 2.00–2.34 (m, 6H), 2.86–2.94 (m, 2H), 3,62 (m, 1H), 3.80 (m, 1H), 4.20 (dd, 2H, J=14.3, 7.2 Hz), 4.42 (m, 1H), 4.65 (m, 1H), 4.80 (m, 1H), 5.57 (m, 1H), 5.93 (dd, 1H, J=15.8, 1.5 Hz), 6.41 (m, 1H), 6.49 (m, 1H), 6.86 (dd, 1H, J=15.8, 5.2 Hz), 7.06 (d, 1H, J=8.7 Hz). HRMS calcd for C$_{23}$H$_{38}$N$_4$O$_6$S+Cs 499.2590, found 499.2596; Anal (C$_{23}$H$_{38}$N$_4$O$_6$S) C, H, N.

Example 23

Preparation of Compound 25: Ethyl-3-[CBZ-L-Leu-L-Pip-L-Gln]-E-Propenoate.

Preparation of Intermediate CBZ-L-Leu-L-Pip-OtBu.

A suspension of CBZ-L-Pip-OtBu (0.52 g, 1.6 mmol) and Pd on C (10%, 0.10g) in EtOAc was stirred under a hydrogen atmosphere (balloon) for 1h. The reaction mixture was filtered through Celite, and the filtrate was concentrated. The resulting oil was coupled with CBZ-L-Leu (0.43 g, 1.6 mmol) using the procedure described in Example 1 for the preparation of ethyl-3-[BOC-L-N-Me-Phe-L-(Tr-Gln)]-E-propenoate, to provide CBZ-L-Leu-L-Pip-OtBu (0.57 g, 83%) as a colorless oil after column chromatography on silica (20% EtOAc/hexanes): IR (thin film) 3300, 1726, 1642 cm$^{-1}$; $^1$H NMR (CDCl$_3$) δ 0.93 (d, 3H, J=6.5 Hz), 1.03 (d, 3H, J=6.5 Hz), 1.46 (s, 9H), 1.50–1.60 (m, 2H), 1.64–1.83 (m, 2H), 2.23–2.27 (m, 2H), 3.19–3.28 (m, 2H), 3.77–3.81 (m, 2H), 4.76–4.83 (m, 2H), 5.10 (s, 2H), 5.26 (d, 1H, J=4.7 Hz), 5.60 (d, 1H, J=8.7 Hz), 7.27–7.36 (m, 5H); Anal. (C$_{24}$H$_{36}$N$_2$O$_5$) C, H, N.

Preparation of Intermediate CBZ-L-Leu-L-Pip.

Trifluoroacetic acid (3 mL) was added to a solution of CBZ-L-Leu-L-Pip-OtBu (0.57 g, 1.3 mmol) in CH$_2$Cl$_2$ (6 mL) at 23° C. The reaction mixture was stirred at 23° C. for 1.5 h after which CCl$_4$ (6 mL) was added. The volatiles were then removed under reduced pressure to afford crude CBZ-L-Leu-L-Pip as a colorless oil. The crude acid thus obtained was immediately utilized in the following coupling procedure.

Preparation of Intermediate Ethyl-3-[CBZ-L-Leu-L-Pip-L-(Tr-Gln)]-E-Propenoate.

Ethyl-3-[BOC-L-(Tr-Gln)]-E-propenoate (0.36 g, 0.67 mmol) was deprotected and coupled with CBZ-L-Leu-L-Pip (0.26 g, 0.67 mmol) using the procedure described in Example 1 for the preparation of ethyl-3-[BOC-L-N-Me-Phe-L-(Tr-Gln)]-E-propenoate to provide ethyl-3-[CBZ-L-Leu-L-Pip-L-(Tr-Gln)]-E-propenoate (0.20 g, 37%) as a foamy white solid: IR (thin film) 3304, 2954, 1713, 1655 cm$^{-1}$; $^1$H NMR (CDCl$_3$, mixture of rotamers) δ 0.86 (d, J=6.5 Hz), 0.94–0.99 (m), 1.22–1.30 (m), 1.32–1.40(m), 1.43–1,50 (m), 1.62–1.68 (m), 1.79–1.98 (m), 2.26–2.45 (m), 3.25 (bs), 3.63–3.77 (m), 4.09–4.21 (m), 4.50–4.58 (m), 4.73–4.78 (m), 4.88–5.10 (m), 5.27 (d, J=7.2 Hz), 5.49 (d, J=8.7 Hz), 5.82 (dd, J=15.6, 1.3 Hz), 5.90 (d, J=15.6 Hz), 6.75 (d, J=5.3 Hz), 6.79–6.88 (m), 7.02–7.36 (m); Anal. (C$_{48}$H$_{56}$N$_4$O$_7$) C, H, N.

Preparation of Product-Ethyl-3-(CBZ-L-Leu-L-Pip-L-Gln)-E-Propenoate.

Ethyl-3-[CBZ-L-Leu-L-Pip-L-(Tr-Gln)]-E-propenoate (0.16 g, 0.18 mmol) was deprotected using the procedure described in Example 1 for the synthesis of ethyl-3-(CBZ-L-N-Me-Phe-L-Gln)-E-propenoate, to provide ethyl-3-(CBZ-L-Leu-L-Pip-L-Gln)-E-propenoate (0.082 g, 83%) as a foamy white solid: IR (thin film) 3306, 1713, 1667 cm$^{-1}$; $^1$H NMR (CDCl$_3$, mixture of rotamers) δ 0.90–1.00 (m), 1.23–1.30 (m), 1.41–2.08 (m), 2.12–2.22 (m), 2.44–2.59 (m), 3.41–3.48 (m), 3.80–3.84 (m), 4.12–4.22 (m), 4.54–4.60 (m), 4.79 (bs), 4.99–5.12 (m), 5.79–5.98 (m), 6.11 (s), 6.27 (s), 6.79–6.92 (m), 7.14 (d, J=7.2 Hz), 7.28–7.34 (m), 7.75 (d, J=7.8 Hz). Anal. (C$_{29}$H$_{42}$N$_4$O$_7$.0.5 H$_2$O) C, H, N.

Example 24

Preparation of Compound 26: 1-[1',2'-Oxazin-2'-yl]-3-(CBZ-L-Leu-L-Pip-L-Gln)-E-Propenone.

Preparation of Intermediate 1,2-Isooxazinane-2-Carboxylic Acid Ethyl Ester.

1,4 Dibromobutane (2.84 mL, 24.0 mmol), N-hydroxyurethane (5.0 g, 48.0 mmol), and KOH (2.67 g, 48.0 mmol) were taken up in 27 mL of EtOH and refluxed for 6 h. The mixture was concentrated in vacuo, and the residue was purified by column chromatography on silica gel (50% EtOAc/hexanes) to provide 1,2-isooxazinane-2-carboxylic acid ethyl ester (2.38 g, 68%) as a clear, colorless oil. $^1$H NMR (CDCl$_3$) δ 1.31 (t, 3H, J=7.0 Hz), 1.69–1.81 (m, 4H), 3.69 (t, 2H, J=5.5 Hz), 3.98 (t, 2H, J=5.3 Hz), 4.20–4.27 (m, 2H).

Preparation of Intermediate 1,2-Isooxazinane•HCl salt 1,2-Isooxazinane-2-carboxylic acid ethyl ester (2.38 g, 15.0 mmol) was refluxed in concentrated HCl for 3 h. The reaction mixture was cooled to rt and washed with Et$_2$O. The organic phase was discarded, and the aqueous layer was concentrated in vacuo. Traces of H$_2$O were removed by adding EtOH and reconcentrating. This yielded the HCl salt of 1,2-isooxazinane as a white solid (1.70 g, 92%) which was dried before subsequent use. $^1$H NMR (CD$_3$OD) δ 1.86–1.90 (m, 2H), 1.96–2.02 (m, 2H), 3.52–3.46 (m, 2H), 4.25–4.29 (m, 2H), 4.88 (bs, 1H). MS calcd for C$_4$H$_{10}$NO 87, found 87.

Preparation of Intermediate 1-[1',2'-Oxazin-2'-yl]-3-(BOC-L-Gln)-E-Propenone 1,2-Isooxazinane-HCl (0.12 g, 0.97 mmol) was coupled with 3-[BOC-L-(Tr-Gln)]-E-propenoic acid (0.50 g, 0.97 mmol) using the procedure described in Example 1 for the preparation of ethyl-3-[BOC-L-N-Me-Phe-L-(Tr-Gln)]-E-propenoate to provide 1-[1',2'-oxazin-2'-yl]-3-(BOC-L-Gln)-E-propenone (0.43 g, 76%) as a glassy white solid. $^1$H NMR (CDCl$_3$) δ 1.43 (s, 9H), 1.71–1.83 (m, 5H), 1.94 (m, 1H), 2.35–2.39 (m, 2H), 3.80–3.85 (m, 2H), 3.93–3.96 (m, 2H), 4.33 (m, 1H), 4.76 (m, 1H), 6.54 (d, 1H, J=15.3 Hz), 6.79 (dd, 1H, J=15.6, 5.6 Hz), 6.96 (m, 1H), 7.20–7.32 (m, 15H); MS calcd for C$_{35}$H$_{41}$N$_3$O$_5$+H 584, found 584.

Preparation of Intermediate 1-[1',2'-Oxazin-2'-yl-3-[CBZ-L-Leu-L-Pip-L-(Tr-Gln)]-E-Propenone.

1-[1',2'-oxazin-2'-yl]-3-(BOC-L-Gln)-E-propenone (0.36 g, 0.66 mmol) was deprotected and coupled with CBZ-L-Leu-L-Pip (0.26 g, 0.66 mmol) using the procedure described in Example 1 for the preparation of ethyl-3-[BOC-L-N-Me-Phe-L-(Tr-Gln)]-E-propenoate to provide 1-[1',2'-oxazin-2'-yl]-3-[CBZ-L-Leu-L-Pip-L-(Tr-Gln)]-E-propenone (0.14 g, 26%) as a foamy white solid: IR (thin film) 3301, 1658, 1630 cm$^{-1}$; $^1$H NMR (CDCl$_3$, mixture of rotamers) δ 0.86 (d, J=6.9 Hz), 0.94–0.99 (m), 1.28–1.40 (m), 1.52–1.57 (m), 1.64–2.01 (m), 2.27–2.15 (m), 3.27 (s, bs), 3.73–3.94 (m), 4.46–4.46 (m), 4.73–4.92 (m), 5.05 (s), 5.10 (s), 5.30 (s), 5.52 (d, J=9.0 Hz), 6.48–6.61 (m), 6.74–6.79 (m), 6.81–6.95 (m), 7.17–7.37 (m), 7.72 (d, J=8.4 Hz).

Preparation of Product-1-[1',2'-Oxazin-2'-yl]-3-[CBZ-L-Leu-L-Pip-L-Gln)-E-Propenone.

1-[1',2'-Oxazin-2'-yl]-3-[CBZ-L-Leu-L-Pip-L-(Tr-Gln)]-E-propenone (0.14 g, 0.17 mmol) was deprotected using the procedure described in Example 1 for the preparation of ethyl-3-(CBZ-L-N-Me-Phe-L-Gln)-E-propenoate, to provide 1-[1',2'-oxazin-2'-yl]-3-(CBZ-L-Leu-L-Pip-L-Gln)-E-propenone (0.060 g, 59%) as a foamy white solid: IR (thin film) 3305, 1660, 1630 cm$^{-1}$; $^1$H NMR (CDCl$_3$, mixture of rotamers) δ 0.91 (d, J=6.9 Hz), 0.94–0.97 (m), 0.92 (d, J=6.5 Hz), 1.26–1.82 (m), 1.93–2.29 (m), 2.45 (d, J=12.1 Hz), 2.56–2.65 (m), 3.47 (s), 3.73–3.96 (m), 4.49–4.83 (m), 4.99 (s), 5.04 (s), 5.09 (s), 5.13 (s), 5.60–5.66 (m), 5.72–5.85 (m), 6.18 (s), 6.3 1 (s), 6.54–6.63 (m), 6.79–6.91 (m), 7.14 (d, J=7.8 Hz), 7.28–7.34 (m), 7.71 (d, J=8.1 Hz). Anal. (C$_{31}$H$_{45}$N$_5$O$_7$) C, H, N.

Example 25

Preparation of Compound 27: Ethyl-3-(CBZ-L-Leu-DL-Pipz-L-Gln)-E-Propenoate.

Preparation of Intermediate FMOC-L-Leu-DL-(4-BOC)-Pipz.

To a suspension of DL-(4-BOC)-piperazine-3-carboxylic acid (0.20 g, 0.87 mmol) in dry CH$_2$Cl$_2$ (10 mL) was added 4-methylmorpholine (0.21 mL, 1.91 mmol) and trimethyl-silylchloride (0.13 g, 1.04 mmol) at rt. A clear, homogeneous solution formed after ~2 h. To this solution was added the FMOC-L-Leu-Cl (0.32 g, 0.87 mmol) (Advanced Chem Tech), and the mixture was stirred at rt overnight. At this time, the reaction mixture was poured into H$_2$O and extracted twice with CH$_2$Cl$_2$, dried over MgSO$_4$, and concentrated to provide FMOC-L-Leu-DL-(4-BOC)-Pipz (0.45 g, 91%) as a pale yellow foamy solid. $^1$H NMR (CDCl$_3$) δ 0.87–1.04 (m, 6H), 1.44 (s, 9H), 1.51 (m, 1H), 1.74 (m, 1H), 2.89–3.10 (m, 2H), 3.67 (m, 1H), 4.03 (m, 1H), 4.21–4.42 (m, 7H), 4.56–4.77 (m, 3H), 7.25–7.77 (m, 8H). MS calcd for C$_{31}$H$_{39}$N$_3$O$_7$+Cs, 698, found 698.

Preparation of Intermediate Ethyl-3-[FMOC-L-Leu-DL-(4-BOC)-Pipz-L-(Tr-Gln)]-E-Propenoate.

Ethyl-3-[BOC-L-(Tr-Gln)]-E-propenoate (0.59 g, 1.23 mmol) was deprotected and coupled to FMOC-L-Leu-DL-(4-BOC)-Pipz (0.70 g, 1.23 mmol) using the procedure described in Example 1 for the preparation of ethyl-3-[BOC-L-N-Me-Phe-L-(Tr-Gln)]-E-propenoate to provide ethyl-3-[FMOC-L-Leu-DL-(4-BOC)-Pipz-L-(Tr-Gln)]-E-propenoate (0.60 g, 49%) as a white foamy solid. $^1$H NMR (CDCl$_3$) δ 0.87–1.03 (m, 6H), 1.18–1.30 (m, 3H), 1.44 (s, 9H), 2.00 (m, 1H), 2.24 (m ,1H), 2.38 (m, 1H), 3.06–3.13 (m, 2H), 3.69–3.77 (m, 2H), 3.89 (m, 1H), 4.07–4.24 (m, 6H), 4.33–4.59 (m, 9H), 5.85 (m, 1H), 6.75–6.88 (m, 2H), 7.19–7.78 (m, 23H). MS calcd for C$_{59}$H$_{67}$N$_5$O$_9$+Cs 1122, found 1122.

Preparation of Intermediate Ethyl-3-[CBZ-L-Leu-(4-BOC)-DL-Pipz-L-(Tr-Gln)]E-Propenoate.

To a solution of ethyl-3-[FMOC-L-Leu-DL-(4-BOC)-Pipz-L-(Tr-Gln)]-E-propenoate (0.60 g, 0.60 mmol) in CHCl$_3$ was added 4-(aminomethyl)piperidine (5 mL) at rt. The reaction mixture was stirred for 1 h and then sequentially washed twice with sat brine, 5 times with 10% aq K$_2$HPO$_4$ buffer (pH 5.5), and once with a sat solution of NaHCO$_3$. The organic phase was dried over MgSO$_4$ and concentrated. The resulting oil (0.34 g, 0.44 mmol) was dissolved in dry CH$_2$Cl$_2$ (30 mL). 4-Methylmorpholine (0.24 g, 2.20 mmol) was added followed by benzylchloroformate (0.13 g, 0.88 mmol), and the mixture was stirred for 4 h at rt. This mixture was then poured into H2O and extracted twice with CH$_2$Cl$_2$. The organic phase was dried over MgSO$_4$, concentrated, and purified by flash column chromatography on silica gel (5% MeOH/CHCl$_3$) providing ethyl-3-[CBZ-L-Leu-(4-BOC)-DL-Pipz-L-(Tr-Gln)]-E-propenoate (0.31 g, 77%) as a white solid foam. $^1$H NMR (CDCl$_3$) δ 0.82–1.00 (m, 6H), 1.23–1.28 (m, 3H), 1.40–1.58 (m, 2H), 1.67 (m, 1H), 1.98 (m, 1H), 2.26 (m, 1H), 2.37 (m, 1H), 2.75 (m, 1H), 3.07–3.11 (m, 2H), 3.50–4.06 (m, 4H), 4.13–4.20 (m, 2H), 4.52–5.15 (m, 6H), 5.87 (m, 1H), 6.75–7.03 (m, 2H), 7.08–7.41 (m, 20H). MS calcd for C$_{52}$H$_{63}$N$_5$O$_9$+Cs 1034, found 1034.

Preparation of Product Ethyl-3-(CBZ-L-Leu-DL-Pipz-L-Gln)-E-Propenoate.

The BOC and trityl protecting groups were both removed from ethyl-3-[CBZ-L-Leu-(4-BOC)-DL-Pipz-L-(Tr-Gln)]-E-propenoate (0.10 g, 0.11 mmol) with trifluoroacetic acid as described in Example 4 for the preparation of ethyl-3-(cyclopentylthiocarbonyl-L-Leu-L-N-Me-Phe-L-Gln)-E-propenoate to provide ethyl-3-(CBZ-L-Leu-DL-Pipz-L-Gln)-E-propenoate (24.0 mg, 39%) as a solid white foam. IR (thin film) 3308, 1704 cm$^{-1}$; $^1$H NMR (CDCl$_3$) δ 0.91–1.01 (m, 6H), 1.24–1.30 (m, 3H), 1.49 (m, 1H), 1.59 (m, 1H), 1.65–1.86 (m, 3H), 1.98 (m, 1H), 2.15–2.24 (m, 2H), 2.67–2.75 (m, 2H), 3.06 (m, 1H), 3.30 (m, 1H), 3.72–3.82 (m, 2H), 4.14–4.21 (m, 2H), 4.57–4.64 (m, 2H), 5.01–5.13 (m, 3H), 5.58 (m, 1H), 5.76 (d, 1H, J=6.5 Hz), 5.90–5.98 (m, 2H), 6.88 (dd, 1H, J=15.6, 5.6 Hz), 7.33 (s, 10H), 7.60 (d, 1H, J=7.2 Hz). HRMS calcd for C$_{28}$H$_{41}$N$_5$O$_7$+Cs 692.2062, found 692.2040.

Example 26

Preparation of Compound 28: Ethyl-3-(CBZ-L-Leu-DL-(4-Benzyl)-Pipz-L-Gln]-E-Propenoate.

Preparation of Intermediate Ethyl-3-[CBZ-L-Leu-DL-(4-Benzyl)-Pipz-L-(Tr-Gln)]-E-Propenoate.

A solution of anh HCl in 1,4-dioxane (3.0 mL of a 4.0 M solution) was added to a solution of ethyl-3-[CBZ-L-Leu-(4-BOC)-DL-Pipz-L-(Tr-Gln)]-E-propenoate (0.18 g, 0.20 mmol) in 1,4-dioxane (3.0 mL) at rt. The reaction mixture was stirred for 2 h at rt, and then concentrated under vacuum. The resulting foamy residue was taken up in EtOAc, washed with a sat NaHCO$_3$ solution, dried over MgSO$_4$, and concentrated. The resulting yellow oil was dissolved in 3.0 mL of DMF. To this solution was added NaH (5.0 mg, 0.20 mmol), followed by benzyl bromide (0.024 mL, 0.20 mmol) after a few minutes. The reaction mixture was stirred at rt overnight. The mixture was then concentrated under vacuum and 10 mL H$_2$O was added to the residue. CH$_2$Cl$_2$ was used to extract the aq phase twice, which was dried over MgSO$_4$, concentrated, and purified using prep TLC (5% MeOH/CHCl$_3$), providing ethyl-3-[CBZ-L-Leu-DL-(4-benzyl)-Pipz-L-(Tr-Gln)]-E-propenoate (0.10 g, 56%) as a yellow foamy solid. $^1$H NMR (CDCl$_3$) δ 0.82–0.94 (m, 6H), 1.21–1.32 (m, 4H), 1.48–1.66 (m, 3H), 1.97–2.13 (m, 2H), 2.25–2.35 (m, 2H), 2.81 (m, 1H), 3.38–3.52 (m, 3H), 3.64–3.76 (m, 3H), 4.14–4.24 (m, 2H), 4.46–5.22 (m, 6H), 5.96 (m, 1H), 6.75–7.04 (m, 2H), 7.15–7.35 (m, 25H), 7.51 (m, 1H). MS calcd for C$_{54}$H$_{61}$N$_5$O$_7$+H 892, found 892.

Preparation of Product-Ethyl-3-[CBZ-L-Leu-DL-(4Benzyl)-Pipz-L-Gln]-E-Propenoate.

Ethyl-3-[CBZ-L-Leu-DL-(4-benzyl)-Pipz-L-(Tr-Gln)]-E-propenoate (0.090 g, 0.10 mmol) was deprotected using the procedure described in Example 1 for the preparation of ethyl-3-(CBZ-L-N-Me-Phe-L-Gln)-E-propenoate, to provide ethyl-3-[CBZ-L-Leu-DL-(4-benzyl)-Pipz-L-Gln]-E-propenoate (0.030 g, 45%) as a solid white foam. IR (thin film) 3323, 1708 cm$^{-1}$; $^1$H NMR (CDCl$_3$) δ 0.94–0.99 (m, 6H), 1.27–1.32 (m, 3H), 1.48 (m, 1H), 1.56 (m, 1H), 1.71–2.17 (m, 6H), 2.83 (m, 1H), 3.37–3.50 (m, 2H), 3.68–3.72 (m, 2H), 4.19–4.24 (m, 3H), 4.60–4.70 (m, 2H), 5.00–5.28 (m, 2H), 5.61–5.92 (m, 4H), 6.03 (m, d, 1H, J=15.6 Hz), 6.87–6.92 (m, 2H), 7.26–7.32 (m, 10H), 7.78 (m, 1H). HRMS calcd for $C_{35}H_{47}N_5O_7$+Cs 782.2530, found 782.2546.

Example 27

Preparation of Compound 29: Ethyl-3-[CBZ-L-Leu-DL-(4-Phenylsulfonyl)-Pipz-L-Gln]-E-Propenoate.

Preparation of Intermediate Ethyl-3-[CBZ-L-Leu-DL-(4-Phenylsulfonyl)-Pipz-L-(Tr-Gln)]-E-Propenoate.

A solution of anh HCl in 1,4dioxane (2.5 mL of a 4.0 M solution) was added to a solution of ethyl-3-[CBZ-L-Leu-(4-BOC)-DL-Pipz-L-(Tr-Gln)]-E-propenoate (0.16 g, 0.18 mmol) in 1,4-dioxane (2.5 mL) at room temperature. The reaction mixture was stirred for 2 h at rt, and then it was concentrated under vacuum. The resulting foam was dissolved in dry $CH_2Cl_2$, and phenylsulfonyl chloride (0.046 mL, 0.36 mmol) and 4-methylmorpholine (0.10 mL, 0.91 mmol) were added at rt and stirred for 2 h. The reaction mixture was poured into $H_2O$ and extracted twice with $CH_2Cl_2$. The organic layer was dried over $MgSO_4$ and concentrated to give a residue that was purified by column chromatography on silica gel (5% MeOH/$CHCl_3$) to provide ethyl-3-[CBZ-L-Leu-DL-(4-phenylsulfonyl)-Pipz-L-(Tr-Gln)]-E-propenoate (0.057 g, 33%) as an off-white foamy solid. $^1$H NMR (CDCl$_3$) δ 0.86–0.93 (m, 6H), 1.25–1.32 (m, 3H), 1.48 (m, 1H), 1.63 (m, 1H), 2.25–2.36 (m, 4H), 3.52 (m, 1H), 3.71–3.78 (m, 4H), 4.12–4.25 (m, 4H), 4.45 (m, 1H), 4.64 (m, 1H), 4.92–5.39 (m, 5H), 5.94 (m, 1H), 6.34 (m 1H), 7.18–7.31 (m, 20H), 7.48–7.67 (m, 5H), 7.77 (m, 1H). MS calcd for $C_{53}H_{59}N_5O_9$S+Cs 1074, found 1074.

Preparation of Product Ethyl-3-(CBZ-L-Leu-DL-(4Phenylsulfonyl)-Pipz-L-Gln)]-E-Propenoate.

Ethyl-3-[CBZ-L-Leu-DL-(4-phenylsulfonyl)-Pipz-L-(Tr-Gln)]-E-propenoate (0.057 g, 0.06 mmol) was deprotected using the procedure described in Example 1 for the preparation of ethyl-3-(CBZ-L-N-Me-Phe-L-Gln)-E-propenoate, to provide ethyl-3-[CBZ-L-Leu-DL-(4-phenylsulfonyl)-Pipz-L-(Gln)]-E-propenoate (22.0 mg, 52%) as a white foamy solid. IR (thin film) 3322, 1667 cm$^{-1}$; $^1$H NMR (CDCl$_3$) 5 0.89–0.98 (m, 6H), 1.22–1.33 (m, 3H), 1.52 (m, 1H), 2.19–2.51 (m, 4H), 3.68–3.78 (m, 5H), 4.14–4.25 (m, 4H), 4.59–4.63 (m, 2H), 5.03–5.11 (m, 3H), 5.21 (m, 1H), 5.43 (m, 1H), 5.57 (m, 1H), 5.94 (m, 1H), 6.85 (m, 1H), 7.20–7.34 (m, 5H), 7.55–7.62 (m, 3H), 7.74–7.80 (m, 2H). HRMS calcd for $C_{34}H_{45}N_5O_9$S+Cs 832.1992, found 832.1982.

Example 28

Preparation of Compound 32: Ethyl-3-(L-N-[(1,3-Dihydro-imidazol-2-one)-Phe]-L-Gln)-E-Propenoate.

Preparation of Intermediate Ethyl-3-[L-N-[(1,3-Dihydro-imidazol-2-one)-Phe]-L-(Tr-Gln)]-E-Propenoate.

A solution of Phe-OtBu.HCl (0.77 g, 2.99 mmol) and triethylamine (0.833 mL, 5.98 mmol) in $CH_2Cl_2$ (10 mL) was added via cannula to a solution of triphosgene (0.295 g, 0.994 mmol) in $CH_2Cl_2$ (25 mL) at 23° C. The reaction mixture was stirred at that temperature for 5 min, and then it was heated to reflux for 1 h. After cooling to 23° C., a solution of aminoacetaldehyde dimethyl acetal (0.314 g, 2.99 mmol) and triethylamine (0.417 mL, 2.99 mmol) in $CH_2Cl_2$ (10 mL) was added via cannula. The reaction mixture was stirred for 3 h at 23° C. and then partitioned between half-saturated $NH_4Cl$ (100 mL) and EtOAc (2×150 mL). The combined organic layers were dried over $Na_2SO_4$ and were concentrated. Purification of the residue by flash column chromatography (5% $CH_3OH/CH_2Cl_2$) provided the intermediate urea as a colorless oil (0.36 g, 34%).

This material was dissolved in $CH_2Cl_2$ (20 mL) at 23° C. Trifluoroacetic acid (10 mL) was added, and the reaction mixture was stirred at 23° C. for 1 h and then concentrated under reduced pressure. The resulting oil was partitioned between 10% NaOH (100 mL) and $Et_2O$ (2×100 mL). The aqueous layer was acidified with concentrated HCl to pH=2 (as indicated by pH paper) and extracted with EtOAc (2×100 mL). The combined organic layers were dried over $Na_2SO_4$ and concentrated to afford crude L-N-(1,3-dihydro-imidazol-2-one)-Phe (0.125 g, 53%) as a white solid. This material was dissolved in DMF (10 mL) and crude ethyl-3-[L-(Tr-Gln)]-E-propenoate. HCl (0.603 mmol) (generated as described in the first deprotection step in Example 1 for the preparation of ethyl-3-[BOC-L-N-Me-Phe-L-(Tr-Gln)]-E-propenoate), 1-hydroxybenzotriazole hydrate (0.122 g, 0.903 mmol), 4-methylmorpholine (0.2 mL, 1.81 mmol), and 1-(3-dimethylaminopropyl)-3-ethylcarbodiimide hydrochloride (0.173 g, 0.903 mmol) were added sequentially, and the reaction niixture was stirred for 18 h at 23° C. and then concentrated under reduced pressure. The resulting oil was partitioned between water (100 mL) and EtOAc (2×100 mL). The combined organic layers were dried over $Na_2SO_4$ and concentrated. Purification of the residue by flash column chromatography (5% $CH_3OH/CH_2Cl_2$) provided ethyl-3-[L-N-[(1,3-dihydro-imidazol-2-one)-Phe]-L-(Tr-Gln)]-E-propenoate (0.129 g, 33%) as a solid yellow foam: $R_f$=0.42 (10% $CH_3OH$ in $CH_2Cl_2$); IR (thin film) 3265, 1671 cm$^{-1}$; $^1$H NMR (CDCl$_3$) δ 1.30 (t, 3H, J=7.2), 1.68–1.78 (m, 1H), 1.89–1.95 (m, 1H), 2.27–2.33 (m, 2H), 3.06 (dd, 1H, J=13.6, 7.3), 3.27 (dd, 1H, J=13.6, 8.4), 4.18 (q, 2H, J=7.2), 4.38 (bs, 1H), 4.96–5.02 (m, 1H), 5.62 (dd, 1H, J=15.7, 1.6), 5.87–5.89 (m, 1H), 6.51–6.53 (m, 1H), 6.62 (dd, 1H, J=15.7, 5.6), 6.90 (s, 1H), 7.00–7.33 (m, 20H), 7.79 (d, 1H, J=7.5), 8.06 (s, 1H).

Preparation of Product-Ethyl-3-(L-N-[(1,3-Dihydro-imidazol-2-one)-Phe]-L-Gln)-E-Propenoate.

Ethyl-3-[L-N-[(1,3-dihydro-imidazol-2-one)-Phe]-L-(Tr-Gln)]-E-propenoate (0.129 g, 0.196 mmol) was deprotected according to the procedure described in Example 1 for the preparation of ethyl-3-(CBZ-L-N-Me-Phe-L-Gln)-E-propenoate. Ethyl-3-(L-N-[(1,3-dihydro-imidazol-2-one)-Phe]-L-Gln)-E-propenoate (0.037 g, 46%) was isolated as a solid beige foam after removal of organic solvents and trituration with 4:1 $Et_2O:CH_3CN$, followed by filtration and washing with 2×10 mL $Et_2O$ and air drying. $R_f$=0.15 (10% $CH_3OH/CH_2Cl_2$); $^1$H NMR (DMSO-d$_6$) δ 1.22 (t, 3H, J=7.2), 1.61–1.80 (m, 2H), 2.01–2.07 (m, 2H), 3.01–3.17 (m, 2H), 4.11 (q, 2H, J=7.2), 4.32–4.41 (m, 1H), 4.87–4.92 (m, 1H), 5.68 (dd, 1H, J=15.7, 1.4), 6.24–6.26 (m, 1H), 6.63–6.72 (m, 2H), 6.74 (s, 1H), 7.12–7.25 (m, 6H), 8.44 (d, 1H, J=8.1), 9.83 (s, 1H); Anal. ($C_{21}H_{26}N_4O_5 \cdot 0.5 H_2O$) C, H, N.

Example 29

Preparation of Compound 33: Ethyl-3-(CBZ-amino-L-N-[(1,3-Dihydro-imidazol-2-one)-Phe]-L-Gln)-E-Propenoate.

Preparation of Intermediate 1-CBZ-2-(2,2-Dimethoxyethyl)-Hydrazine.

Aminoacetaldehyde dimethyl acetal (0.430 g, 3.95 mmol) was added to a solution of N-CBZ-3-phenyl-oxaziridine (1.11 g, 4.35 mmol) (prepared as described in *Tetrahedron Let.* 1993, 6859, the disclosure of which is entirely incorporated herein by reference) in $CH_2Cl_2$ (20 mL) at 23° C. The resulting yellow solution was stirred at 23° C. for 18 h, and it then was concentrated under reduced pressure. Purification of the residue by flash column chromatography (3%

CH$_3$OH/CH$_2$Cl$_2$) provided 1-CBZ-2-(2,2-dimethoxyethyl)-hydrazine (0.434 g, 43%) as a pale yellow oil: R$_f$=0.40 (5% CH$_3$OH/CH$_2$Cl$_2$); IR (thin film) 3317, 1721, 1456 cm$^{-1}$; $^1$H NMR (C$_6$D$_6$) δ 2.96 (bs, 2H), 3.06 (bs, 6H), 3.97 (bs, 1H), 4.37 (bs, 1H), 4.97 (bs, 2H), 5.87 (bs, 1H), 6.98–7.18 (m, 5H).

Preparation of Intermediate Ethyl-3-[CBZ-amino-L-N-[(1,3-Dihydro-imidazol-2-one)-Phe]-L-(Tr-Gln)]-E-Propenoate.

A solution of Phe-OtBu.HCl (0.440 g, 1.71 mmol) and triethylamine (0.345 mL, 2.47 mmol) in CH$_2$Cl$_2$ (20 mL) was added via cannula to a solution of triphosgene (0.168 g, 0.566 mmol) in CH$_2$Cl$_2$ (40 mL) at 23° C. The reaction mixture was stirred at that temperature for 5 min, and then it was heated to reflux for 1 h. After cooling to 23° C., a solution of 1-CBZ-2-(2,2-dimethoxyethyl)-hydrazine (0.434 g, 1.71 mmol) and triethylamine (0.173 mL, 1.24 mmol) in CH$_2$Cl$_2$ (10 mL) was added via cannula. The reaction mixture was stirred for 1 h at 23° C., and then it was partitioned between half-saturated NH$_4$Cl (100 mL) and EtOAc (2×150 mL). The combined organic layers were dried over Na$_2$SO$_4$ and were concentrated. Purification of the residue by flash column chromatography (3% CH$_3$OH/CH$_2$Cl$_2$) provided the intermediate urea as a colorless oil (0.56 g, 65%). This material was dissolved in CH$_2$Cl$_2$ (20 mL) at 23° C. Trifluoroacetic acid (10 mL) was added, and the reaction mixture was stirred at 23° C. for 1.5 h. CCl$_4$ (10 mL) was added, and the mixture was concentrated under reduced pressure. The resulting oil was partitioned between 10% NaOH (100 mL) and Et$_2$O (2×100 mL). The aqueous layer was acidified with concentrated HCl to pH=2 (as indicated by pH paper) and was extracted with EtOAc (2×100 mL). The combined organic layers were dried over Na$_2$SO$_4$ and concentrated to afford crude CBZ-amino-L-N-(1,3-dihydro-imidazol-2-one)-Phe (0.374 g, 89%) as a solid white foam. This material was dissolved in CH$_2$Cl$_2$ (10 mL) and crude ethyl-3-[L-(Tr-Gln)]-E-propenoate.HCl (0.981 mmol) (generated as described in the first deprotection step in Example 1 for the preparation of ethyl-3-[BOC-L-N-Me-Phe-L-(Tr-Gln)]-E-propenoate), 1-hydroxybenzotriazole hydrate (0.172 g, 1.27 mmol), 4-methylmorpholine (0.323 mL, 2.94 mmol), and 1-(3-dimethylaminopropyl)-3-ethylcarbodiimide hydrochloride (0.244 g, 1.27 mmol) were added sequentially. The reaction mixture was stirred for 18 h at 23° C., and it then was partitioned between water (100 mL) and EtOAc (2×100 mL). The combined organic layers were dried over Na$_2$SO$_4$ and concentrated. Purification of the residue by flash column chromatography (5% CH$_3$OH/CH$_2$Cl$_2$) provided ethyl-3-[CBZ-amino-L-N-[(1,3-dihydro-imidazol-2-one)-Phe]-L-(Tr-Gln)]-E-propenoate (0.449 g, 57%) as a solid white foam: R$_f$=0.44 (10% CH$_3$OH in CH$_2$Cl$_2$); IR (thin film) 3284, 1681 cm$^{-1}$; $^1$H NMR (CDCl$_3$) δ 1.23 (t, 1H, J=7.2), 1.42–1.44 (m, 1H), 2.00–2.16 (m, 3H), 3.08 (dd, 1H, J=13.4, 7.5), 3.32–3.39 (m, 1H), 4.01–4.18 (m, 3H), 4.47 (bs, 1H), 4.90 (bs, 2H), 4.99–5.04 (m, 1H), 5.60 (dd, 1H, J=16.0, 1.6), 5.86 (bs, 1H), 6.54 (d, 1H, J=3.1), 6.66 (dd, 1H, J=16.0, 4.5), 6.94–7.32 (m, 26H), 7.83 (s, 1H); Anal. (C$_{48}$H$_{47}$N$_5$O$_7$.0.5 H$_2$O) C, H, N.

Preparation of Product Ethyl-3-(CBZ-amino-L-N-[(1,3-Dihydro-imidazol-2-one)-Phe]-L-Gln)-E-Propenoate.

Ethyl-3-[CBZ-amino-L-N-[(1,3-dihydro-imidazol-2-one)-Phe]-L-(Tr-Gln)]-E-propenoate (0.147 g, 0.182 mmol) was deprotected according to the procedure described in Example 1 for the preparation of ethyl-3-(CBZ-L-N-Me-Phe-L-Gln)-E-propenoate. Ethyl-3-(CBZ-amino-L-N-[(1,3-dihydro-imidazol-2-one)-Phe]-L-Gln)-E-propenoate (0.042 g, 40%) was isolated as a white solid after removal of organic solvents and trituration with Et$_2$O, followed by filtration and washing with 2×10 mL Et$_2$O and air drying: mp=216–218° C.; R$_f$=0.27 (10% CH$_3$OH/CH$_2$Cl$_2$); $^1$H NMR (DMSO-d$_6$) δ 1.22 (t, 3H, J=7.2), 1.61–2.06 (m, 2H), 2.01–2.06 (m, 2H), 3.11–3.13 (m, 2H), 3.36–3.38 (m, 1H), 4.11 (q, 2H, J=7.2), 4.34–4.38 (m, 1H), 4.90–4.96 (m, 1H), 5.09 (bs, 2H), 5.66 (d, 1H, J=15.7), 6.53 (d, 1H, J=2.8), 6.69 (dd, 1H, J=15.7, 5.6), 6.75–6.77 (m, 2H), 7.21 (bs, 6H), 7.37 (bs, 4H), 8.52 (d, 1H, J=8.1), 10.14 (s, 1H); Anal. (C$_{29}$H$_{33}$N$_5$O$_7$) C, H, N.

Example 30

Preparation of Compound 34: Ethyl-3-(Ethylthiocarbonyl-L-Val-L-N-Me-Phe-L-Gln)-E-Propenoate.

Preparation of Intermediate Ethyl-3-[BOC-L-Val-L-N-Me-Phe-L-(Tr-Gln)]-E-Propenoate.

This material was prepared from ethyl-3-[BOC-L-(Tr-Gln)]-E-propenoate (0.832 g, 1.53 mmol) and BOC-L-Val-L-N-Me-Phe (0.570 g, 1.51 mmol) using the method described in Example 6 for the formation of 1-(2',3'-dihydroindolin-1-yl)-3-[BOC-L-Leu-L-N-Me-Phe-L-(Tr-Gln)]-E-propenone to give ethyl-3-[BOC-L-Val-L-N-Me-Phe-L-(Tr-Gln)]-E-propenoate after column chromatography on silica gel (gradient: 43%–50% EtOAc in hexanes) as a white foam (0.789 g, 64%): IR (thin film) 3295, 1708, 1660 cm$^{-1}$; $^1$H NMR (CDCl$_3$) (mixture of isomers) δ 0.66–0.73 (m), 0.81 (d, J=6.8 Hz), 0.86 (d, J=6.8 Hz), 1.23–1.37 (m), 1.35 (s), 1.42 (s), 1.62–1.85 (m), 1.88–2.06 (m), 2.20–2.27 (m), 2.83–3.03 (m), 2.88 (s), 2.99 (s), 3.31 (dd, J=14.0, 8.2 Hz), 3.41 (dd, J=14.0, 5.8 Hz), 4.03–4.10 (m), 4.16 (q, J=7.2 Hz), 4.17 (q, J=7.2 Hz), 4.27–4.34 (m), 4.45–4.56 (m), 4.57–4.70 (m), 4.88–5.03 (m), 5.59 (d, J=15.7 Hz), 5.87 (d, J=15.7 Hz), 6.20 (d, J=8.4 Hz), 6.66 (dd, J=15.7, 5.1 Hz), 6.80 (dd, J=15.7, 6.1 Hz), 6.89–7.05 (m), 7.12–7.34 (m), 7.88 (d, J=8.1 Hz). Anal. (C$_{48}$H$_{58}$N$_4$O$_7$.0.5 H$_2$O) C, H, N.

Preparation of Intermediate Ethyl-3-[Ethylthiocarbonyl-L-Val-L-N-Me-Phe-L-(Tr-Gln)]-E-Propenoate.

Ethyl-3-[BOC-L-Val-L-N-Me-Phe-L-(Tr-Gln)]-E-propenoate (0.366 g, 0.456 mmol) was deprotected and coupled with ethyl chlorothiolformate (0.057 mL, 0.55 mmol) as described in Example 6 for the formation of 1-(2',3'-dihydroindolin-1-yl)-3-[ethylthiocarbonyl-L-Leu-L-N-Me-Phe-L-(Tr-Gln)]-E-propenone to give ethyl-3-[ethylthiocarbonyl-L-Val-L-N-Me-Phe-L-(Tr-Gln)]-E-propenoate after column chromatography on silica gel (gradient: 44%–50% EtOAc in hexanes) as a white foam (0.217 g, 60%): IR (thin film) 3295, 1713, 1655 cm$^{-1}$; $^1$H NMR (CDCl$_3$) (mixture of isomers) δ 0.48 (d, J=6.5 Hz), 0.71 (d, J=6.8 Hz), 0.80–0.89 (m), 1.17–1.22 (m), 1.58–2.06 (m), 2.19–2.32 (m), 2.65–3.04 (m), 2.84 (s), 2.97 (s), 3.29–3.43 (m), 4.18 (q, J=7.2 Hz), 4.49–4.59 (m), 4.65–4.71 (m), 4.75–4.83 (m), 5.65 (dd, J=15.9, 1.6 Hz), 5.71–5.76 (m), 5.81–5.90 (m), 6.31–6.36 (m), 6.70 (dd, J=15.9, 5.3 Hz), 6.79 (dd, J=15.9, 5.9 Hz), 6.88 (s), 7.01 (s), 7.12–7.34 (m), 7.75–7.80 (m). Anal. (C$_{46}$H$_{54}$N$_4$O$_6$S.0.5 H$_2$O) C, H, N.

Preparation of Product-Ethyl-3-(Ethylthiocarbonyl-L-Val-L-N-Me-Phe-L-Gln)-E-Propenoate.

Ethyl-3-[ethylthiocarbonyl-L-Val-L-N-Me-Phe-L-(Tr-Gln)]-E-propenoate (0.187 g, 0.236 mmol) was deprotected using the procedure described in Example 1 for the formation of ethyl-3-(CBZ-L-N-Me-Phe-L-Gln)-E-propenoate to give ethyl-3-(ethylthiocarbonyl-L-Val-L-N-Me-Phe-L-Gln)-E-propenoate after column chromatography (50% acetone in hexanes, then 6% MeOH in CH$_2$Cl$_2$) as a white foam (0.076 g, 58%): IR (thin film) 3307, 1660 cm$^{-1}$; $^1$H NMR (CDCl$_3$) (mixture of isomers) δ 0.47 (d, J=6.5 Hz), 0.77 (d, J=6.8 Hz), 0.92 (d, J=6.5 Hz), 0.93 (d, J=6.5 Hz), 1.25 (t, J=7.2 Hz), 1.29 (t, J=7.2 Hz), 1.42–1.54 (m), 1.64–1.79 (m), 1.80–2.03 (m), 2.08–2.31 (m), 2.73–3.01 (m), 2.92 (s), 3.04–3.15 (m), 3.07 (s), 3.31–3.47 (m), 4.16–4.26 (m), 4.19 (q, J=7.2 Hz), 4.51–4.65 (m), 4.70–4.78 (m), 5.72 (dd, J=15.6, 1.6 Hz), 5.85–6.05 (m), 6.19 (bs), 6.56 (d, J=8.1 Hz), 6.75 (dd, J=15.6, 5.3 Hz), 6.80–6.89 (m), 7.15–7.35 (m), 7.46 (d, J=7.8 Hz). Anal. ($C_{27}H_{40}N_4O_6S$) C, H, N.

Example 31

Preparation of Compound 35: Ethyl-3-(Cyclopentylthiocarbonyl-L-Val-L-N-Me-PHe-L-Gln-)-E-Propenoate.

Preparation of Intermediate Ethyl-3-[Cyclopentylthiocarbonyl-L-Val-L-N-Me-Phe-L-(Tr-Gln)]-E-Propenoate.

Ethyl-3-[BOC-L-Val-L-N-Me-Phe-L-(Tr-Gln)]-E-propenoate (0.365 g, 0.455 mmol) was deprotected and coupled with cyclopentyl chlorothiolformate (0.09 mL, about 0.5 mmol) using the procedure described in Example 6 for the formation of 1-(2',3'-dihydroindolin-1-yl)-3-[ethylthiocarbonyl-L-Leu-L-N-Me-Phe-L-(Tr-Gln)]-E-propenone to give ethyl-3-[cyclopentylthiocarbonyl-L-Val-L-N-Me-Phe-L-(Tr-Gln)]-E-propenoate after column chromatography on silica gel (40%–50% EtOAc in hexanes) as a white foam (0.231 g, 61%): IR (thin film) 3295, 1713, 1655, 1631 cm$^{-1}$; $^1$H NMR (CDCl$_3$) (mixture of isomers) δ 0.50 (d, J=6.5 Hz), 0.73 (d, J=6.8 Hz), 0.80–0.88 (m), 1.22–2.31 (m), 2.84–3.04 (m), 2.86 (s), 2.98 (s), 3.29–3.41 (m), 3.54–3.69 (m), 4.08–4.25 (m), 4.17 (q, J=7.2 Hz), 4.48–4.63 (m), 4.67–4.82 (m), 5.64 (dd, J=15.7, 1.6 Hz), 5.76–5.82 (m), 5.83–5.91 (m), 5.87 (dd, J=15.7, 1.6 Hz), 6.39–6.45 (m), 6.70 (dd, J=15.7, 5.3 Hz), 6.79 (dd, J=15.7, 5.8 Hz), 6.93 (s), 7.06 (s), 7.12–7.33 (m), 7.72 (d, J=7.8 Hz). Anal. ($C_{49}H_{58}N_4O_6S$. 0.5 H$_2$O) C, H, N.

Preparation of Product-Ethyl-3-(Cyclopentylthiocarbonyl-L-Val-L-N-Me-Phe-L-Gln)-E-Propenoate.

Ethyl-3-[cyclopentylthiocarbonyl-L-Val-L-N-Me-Phe-L-(Tr-Gln)]-E-propenoate (0.179 g, 0.215 mmol) was deprotected using the procedure described in Example 1 for the formation of ethyl-3-[CBZ-L-N-Me-Phe-L-Gln]-E-propenoate to give ethyl-3-(cyclopentylthiocarbonyl-L-Val-L-N-Me-Phe-L-Gln)-E-propenoate after column chromatography on silica gel (50% acetone in hexanes, then 6% MeOH in CH$_2$Cl$_2$) as a white foam (0.086 g, 68%): IR (thin film) 3295, 1713, 1666, 1631 cm$^{-1}$; $^1$H NMR (CDCl$_3$) (mixture of isomers) δ 0.48 (d, J=6.5 Hz), 0.77 (d, J=6.8 Hz), 0.92 (d, J=6.5 Hz), 0.93 (d, J=6.8 Hz), 1.29 (t, J=7.2 Hz), 1.37–1.79 (m), 1.81–2.29 (m), 2.91–3.00 (m), 2.92 (s), 3.03–3.15 (m), 3.06 (s), 3.34 (dd, J=14.0, 5.3 Hz), 3.43 (dd, J=14.0, 6.7 Hz), 3.59–3.69 (m), 4.16–4.26 (m), 4.18 (q, J=7.2 Hz), 4.52–4.65 (m), 4.68–4.77 (m), 5.72 (dd, J=15.9, 1.6 Hz), 5.78 (bs), 5.85 (bs), 5.90 (dd, J=15.6, 1.2 Hz), 6.01 (bs), 6.19 (bs), 6.42 (d, J=8.1 Hz), 6.67 (d, J=9.0 Hz), 6.75 (dd, J=15.6, 5.3 Hz), 6.80–6.87 (m), 7.16–7.34 (m), 7.42 (d, J=7.8 Hz). Anal. ($C_{30}H_{44}N_4O_6S$) C, H, N.

Example 32

Preparation of Compound 36: N-Methoxy-N-Methyl-3-(Ethylthiocarbonyl-L-Leu-L-N-Me-Phe-L-Gln)-E-Propenamide.

Preparation of Intermediate N-Methoxy-N-Methyl-3-[BOC-L-Leu-L-N-Me-Phe-L-(Tr-Gln)]-E-Propenamide.

N-Methoxy-N-methyl-3-[BOC-L-(Tr-Gln)]-E-propenamide (0.29 g, 0.58 mmol) was deprotected and coupled to BOC-L-Leu-L-N-Me-Phe (0.23 g, 0.58 mmol) using the procedure described in Example 1 for the preparation of ethyl-3-[BOC-L-N-Me-Phe-L-(Tr-Gln)]-E-propenoate to provide N-methoxy-N-methyl-3-[BOC-L-Leu-L-N-Me-Phe-L-(Tr-Gln)]-E-propenamide (0.23 g, 47%) as a white solid foam after column chromatography on silica (2% methanol/CHCl$_3$). $^1$H NMR (CDCl$_3$) δ 0.63–0.66 (m, 6H), 0.71 (m, 1H), 0.86–0.95 (m, 3H), 1.06 (m, 1H), 1.31–1.44 (m, 9H), 1.84 (m, 1H), 2.00 (m, 1H), 2.25–2.28 (m, 2H), 2.91–3.00 (m, 3H), 3.23 (s, 3H), 3.66–3.68 (m, 3H), 4.13 (m, 1H), 4.58 (m, 1H), 4.71 (m, 1H), 4.86 (m, 1H), 6.35 (m, 1H), 6.55 (m, 1H), 6.80 (m, 1H), 7.10–7.33 (m, 20H), 8.20 (d, 1H, J=8.7 Hz). MS calcd for $C_{49}H_{61}N_5O_7$+Na 854, found 854.

Preparation of Intermediate N-Methoxy-N-Methyl 3-[Ethylthiocarbonyl-L-Leu-L-N-Me-Phe-L-(Tr-Gln)]-E-Propenamide.

N-Methoxy-N-methyl-3-[BOC-L-Leu-L-N-Me-Phe-L-(Tr-Gln)]-E-propenamide (0.098 g, 0.13 mmol) was deprotected and treated with ethylchlorothiolformate (0.016 mL, 0.15 mmol) using the procedure described in Example 22 for the preparation of ethyl-3-[ethylthiocarbonyl-L-Leu-L-Pro-L-(Tr-Gln)]-E-propenoate, to provide N-methoxy-N-methyl-3-[ethylthiocarbonyl-L-Leu-L-N-Me-Phe-L-(Tr-Gln)]-E-propenamide (0.041 g, 39%) as a clear glass. $^1$H NMR (CDCl$_3$) δ 0.61–0.75 (m, 3H), 0.80–0.88 (m, 2H), 1.15–1.27 (m, 4H), 1.34–1.44 (m, 2H), 1.65–1.96 (m, 5H), 2.25–2.33 (m, 2H), 2.72–3.05 (m, 3H), 3.20 (s, 3H), 3.66 (s, 3H), 4.61 (m, 1H), 5.77 (dd, 1H, J=17.4, 7.5 Hz), 6.49 (m, 1H), 6.83 (m, 1H), 7.12 (m, 1H), 7.19–7.33 (m, 20H), 8.01 (d, 1H, J=8.1 Hz). MS calcd for $C_{47}H_{57}N_5O_6S$+Cs MS calcd for 952, found 952.

Preparation of Product N-Methoxy-N-Methyl-3-(Ethylthiocarbonyl-L-Leu-L-N-Me-Phe-L-Gln)-E-Propenamide.

N-Methoxy-N-methyl-3-[ethylthiocarbonyl-L-Leu-L-N-Me-Phe-L-(Tr-Gln)]-E-propenamide (0.040 g, 0.049 mmol) was deprotected using the procedure described in Example 1 for the preparation ethyl-3-[CBZ-L-N-Me-Phe-L-Gln]-E-propenoate, to provide N-methoxy-N-methyl-3-(ethylthiocarbonyl-L-Leu-L-N-Me-Phe-L-Gln)-E-propenamide (17.0 mg, 61%) as a white foam after column chromatography (2% methanol/CHCl$_3$). IR (thin film) 3274, 1678 cm$^{-1}$; $^1$H NMR (CDCl$_3$) δ 0.63–0.64 (m, 3H), 0.91 (d, 2H, J=6.2 Hz), 1.22–1.28 (m, 4H), 1.43 (m, 1H), 1.63 (m, 1H), 1.95–2.02 (m, 2H), 2.80–2.98 (m, 4H), 3.25 (s, 3H), 3.69–3.70 (m, 3H), 4.42 (m, 1H), 4.62–4.66 (m, 2H), 6.09 (m, 1H), 6.18 (dd, 1H, J=15.0, 7.5 Hz), 6.57 (m, 1H), 6.82 (m, 1H), 7.15–7.34 (m, 7H), 7.89 (d, 1H, J=8.4 Hz). HRMS calcd for $C_{28}H_{43}N_5O_6S$+Cs 710.1988, found 710.2014.

Example 33

Preparation of Compound 30: Ethyl-3-([(5-CBZ-Amino)-2-Phenyl-6-Oxo-1,6-Dihydro-1-Pyrimidinyl]-L-Gln)-E-Propenoate.

Preparation of Intermediate Ethyl-3-{[(5-CBZ-Amino)-2-Phenyl-6-Oxo-1,6-Dihydro-1-Pyrimidinyl]-L-(Tr-Gln)}-E-Propenoate.

Ethyl-3-[BOC-L-(Tr-Gln)]-E-propenoate (0.39 g, 0.72 mmol) was deprotected and coupled with [(5-CBZ-amino)-2-phenyl-6-oxo-1,6-dihydro-1-pyrimidinyl]acetic acid (0.28 g, 0.73 mmol) (prepared according to the procedure of C. A. Veale, et al., *J. Med. Chem.* 1995, 38, 98, the disclosure of which is entirely incorporated herein by reference) using the procedure described in Example 1 for the preparation of ethyl-3-[BOC-L-N-Me-Phe-L-(Tr-Gln)]-E-propenoate), to give ethyl-3-{[(5-CBZ-amino)-2-phenyl-6-oxo-1,6-dihydro-1-pyrimidinyl]-L-(Tr-Gln)}-E-propenoate (0.43 g, 73%) as a white solid after column chromatography on silica (3% methanol/CHCl$_3$): mp=106–112° C.; IR (thin film) 3297, 1722, 1658 cm$^{-1}$; $^1$H NMR (CDCl$_3$) δ 1.29 (t, 3H, J=7.2 Hz), 1.76–1.86 (m, 1H), 1.93–2.04 (m, 1H), 2.36–2.52 (m, 2H), 4.07–4.30 (m, 5H), 4.51 (bs, 1H), 5.21 (s, 2H), 5.81 (dd, 1H, J=15.6, 1.6 Hz), 6.73 (dd, 1H, J=15.6, 4.8 Hz), 6.86 (s, 1H), 7.08–7.23 (m, 15H), 7.29–7.54 (m, 11H), 8.73 (bs, 1H); Anal. (C$_{48}$H$_{45}$N$_5$O$_7$.1.0 H$_2$O) C, H, N.

Preparation of Product Ethyl-3-{[(5-CBZ-Amino)-2-Phenyl-Oxo-1,6-Dihydro-1-Pyrimidinyl]-L-Gln}-E-Propenoate.

Ethyl-3-{[(5-CBZ-amino)-2-phenyl-6-oxo-1,6-dihydro-1-pyrimidinyl]-L-(Tr-Gln)}-E-propenoate (0.22 g, 0.27 mmol) was deprotected using the procedure described in Example 1 for the preparation of ethyl-3-[CBZ-L-N-Me-Phe-L-Gln]-E-propenoate, to provide ethyl-3-{[(5-CBZ-amino)-2-phenyl-6-oxo-1,6-dihydro-1-pyrimidinyl]-L-Gln}-E-propenoate (0.12 g, 79%) as a white solid after removal of organic solvents and trituration with Et$_2$O, followed by filtration and washing with 2×10 mL Et$_2$O and air drying: mp=200–205° C.; IR (thin film) 3278, 1719, 1650 cm$^{-1}$; $^1$H NMR (CDCl$_3$) δ 1.22 (t, 3H, J=7.2 Hz), 1.56–1.68 (m, 1H), 1.71–1.77 (m, 1H), 2.01–2.06 (m, 2H), 4.13 (q, 2H, J=7.2 Hz), 4.39–4.55 (m, 3H), 5.18 (s, 2H), 5.78 (dd, 1H, J=15.9, 1.6 Hz), 6.70–6.77 (m, 2H), 7.24 (s, 1H), 7.30–7.55 (m, 10H), 8.34 (d, 1H, J=8.1 Hz), 8.45 (s, 1H), 8.94 (s, 1H); Anal. (C$_{29}$H$_{31}$N$_5$O$_7$.0.25 H$_2$O) C, H, N.

Example 34

Preparation of Compound 31: Ethyl-3-{[(5-Amino)-2-Phenyl-6Oxo-1,6-Dihydro-1-Pyrimidinyl]-L-Gln}-Propenoate.

Preparation of Product Ethyl-3-{[(5-Amino)-2-Phenyl-6-Oxo-1,6-Dihydro-1-Pyrimidinyl]-L-Gln}-E-Propenoate.

Borontribromide (0.18 mL of a 1.0 M solution in CH$_2$Cl$_2$, 0.18 mmol) was added to a solution of ethyl-3-{[(5-CBZ-amino)-2-phenyl-6-oxo-1,6-dihydro-1-pyrimidinyl]-L-Gln}-E-propenoate (0.050 g, 0.089 mmol) in trifluoroacetic acid (4 mL) at 23° C. The reaction mixture was stirred for 2 h at 23° C., then it was quenched with EtOH (2 mL) and concentrated. The residue was then partitioned between NaHCO$_3$ (50 mL) and EtOAc (2×100 mL). The combined organic layers were dried over Na$_2$SO$_4$ and concentrated to afford ethyl-3-{[(5-amino)-2-phenyl-6-oxo-1,6-dihydro-1-pyrimidinyl]-L-Gln}-E-propenoate (0.013 g, 36%) as a white solid: mp=175° C. (dec); IR (thin film) 3421, 1646 cm$^{-1}$; $^1$H NMR (DMSO-d$_6$) δ 1.23 (t, 3H, J=7.2 Hz), 1.62–1.64 (m, 1H), 1.71–1.78 (m, 1H), 2.01–2.06 (m, 2H), 4.13 (q, 2H, J=7.2 Hz), 4.37–4.51 (m, 3H), 5.14 (bs, 1H), 5.79 (d, 1H, J=15.6 Hz), 6.53–6.78 (m, 2H), 7.09–7.52 (m, 6H), 8.28 (d, 1H, J=8.4 Hz).

Example 35

Preparation of Compound 37: Ethyl-3-[(S)-3-(CBZ-Amino)4-Oxo-4,6,7,8-Tetrahydropyrrolo [1,2-α] Pyrimidine-6-L-Gln]-E-Propenoate.

Preparation of Intermediate (S)-Pyrrolidin-2-one-5-Carboxylic Acid t-Butyl Ester.

To a suspension of L-pyroglutamic acid (2.00 g, 15.49 mmol) in t-butyl acetate was added 70% HClO$_4$ (0.46 mL, 17.04 mmol). The suspension was stirred at rt in a tightly closed flask overnight. The resulting solution was poured slowly into a sat. solution of NaHCO$_3$ and extracted twice with EtOAc. The organic phase was dried over MgSO$_4$ and concentrated to provide (S)-pyrrolidin-2-one-5-carboxylic acid t-butyl ester. (2.04 g, 85%) as a white solid $^1$H NMR (CDCl$_3$) δ 1.48 (s, 9H), 2.16–2.48 (m, 4H), 4.14 (m, 1H), 5.97 (bs, 1H). MS calcd for C$_9$H$_{15}$NO$_3$+H 186, found 186.

Preparation of Intermediate (S)-Pyrrolidin-2-thione-5-Carboxylic Acid t-Butyl Ester.

To a solution of (S)-pyrrolidin-2-one-5-carboxylic acid t-butyl ester (2.04 g, 11.01 mmol) in benzene was added Lawesson's Reagent (2.22 g, 5.50 mmol). The reaction mixture was heated at reflux overnight, concentrated under vacuum, and purified by column chromatography on silica gel (5% MeOH/CHCl$_3$) to provide (S)-pyrrolidin-2-thione-5-carboxylic acid t-butyl ester (1.75 g, 79%) as a tan solid. $^1$H NMR (CDCl$_3$) δ 1.49 (s, 9H), 2.30 (m, 1H), 2.53 (m, 1H), 2.85–3.04 (m, 2H), 4.42 (t, 1H, J=7.7 Hz), 7.88 (bs, 1H). MS calcd for C$_9$H$_{15}$NO$_2$S+H 202, found 202.

Preparation of Intermediate (S)-2-Methylsulfanyl-3,4-Dihydro-5H-Pyrrole-5-Carboxylic Acid t-Butyl Ester.

To a solution of (S)-pyrrolidin-2-thione-5-carboxylic acid t-butyl ester (1.75 g, 8.71 mmol) in 35 mL of dry THF was added MeI (2.2 mL, 34.83 mmol) at rt. The mixture was stirred at rt for 3 h and concentrated under vacuum. CH$_2$Cl$_2$ was added to the resulting oil which was poured into a sat. solution of NaHCO$_3$. This was extracted 3 times with CH$_2$Cl$_2$, dried over MgSO$_4$, and concentrated to provide (S)-2-methylsulfanyl-3,4-dihydro-5H-pyrrole-5-carboxylic acid t-butyl ester (1.63 g, 87%) as a brown oil which was used without further purification $^1$H NMR (CDCl$_3$) δ 1.46 (s, 9H), 2.09 (m, 1H), 2.28 (m, 1H), 2.48 (s, 3H), 2.56–2.80 (m, 2H), 4.59 (m, 1H). MS calcd for C$_{10}$H$_{17}$NO$_2$S+H, 216, found 216.

Preparation of Intermediate (S)-2-Amino-3,4-Dihydro-5H-Pyrrole-5-Carboxylic Acid t-Butyl Ester.HCl Salt.

To a solution of (S)-2-methylsulfanyl-3,4-dihydro-5H-pyrrole-5-carboxylic acid t-butyl ester (0.42 g, 1.95 mmol) in 4.0 mL anhydrous MeOH was added anh NH$_4$Cl (0.11 g, 2.05 mmol). The reaction mixture was heated to reflux for 2 h, concentrated in vacuo, and the residue was taken up in CH$_2$C$_2$. The white solids were filtered, and the filtrate was concentrated to provide (S)-2-amino-3,4-dihydro-5H-pyrrole-5carboxylic acid t-butyl ester.HCl (0.41 g, 94%) as a light yellow solid $^1$H NMR (CDCl$_3$) δ 1.49 (s, 9H), 2.24 (m, 1H), 2.52 (m, 1H), 3.06–3.08 (m, 2H), 4.44 (m, 1H), 9.81–9.8 (m, 2H). MS calcd for C$_9$H$_{16}$N$_2$O$_2$+H 185, found 185.

Preparation of Intermediate (S)4-Oxo-4,6,7,8-Tetrahydropyrrolo [1,2-α] Pyrimidine-3,6-Dicarboxylic Acid 6t-Butyl Ester 3-Methyl Ester.

A solution of freshly prepared sodium methoxide (Na, 50% by weight in paraffin, 0.084 g, 1.84 mmol, 2.25 mL anh MeOH) was added slowly to a solution of (S)-2-amino-3, 4-dihydro-5H-pyrrole-5-carboxylic acid t-butyl ester.HCl (0.41 g, 1.84 mmol) in 2.25 mL anh MeOH cooled to –10° C. After 1 h, the resulting white precipitate (NaCl) was filtered, and the solution of this free base was slowly added to a solution of dimethylmethoxymethylene malonate (0.32 g, 1.84 mmol) in 2.25 mL anh MeOH at –10° C. The reaction mixture was stirred at 0° C. overnight at which time it was concentrated under vacuum, and the residue was purified by column chromatography on silica gel (2% MeOH/CHCl$_3$) to afford (S)-4-oxo-4,6,7,8-tetrahydropyrrolo[1,2-α]pyrimidine-3,6-dicarboxylic acid 6-t-butyl ester 3-methyl ester (0.22 g, 40%) as a yellow oil. $^1$H NMR (CDCl$_3$) δ 1.49 (s, 9H), 2.31 (m, 1H), 2.57 (m, 1H), 3.09–3.33 (m, 2H), 3.90 (s, 3H), 5.03 (m, 1H), 8.69 (s, 1H). MS calcd C$_{14}$H$_{18}$N$_2$O$_5$+295, found 295.

Preparation of Intermediate (S)4-Oxo-4,6,7,8-Tetrahydropyrrolo-[1,2-α]Pyrimidine-3,6-Dicarboxylic Acid 6t-Butyl Ester.

To a solution of (S)4-oxo-4,6,7,8-tetrahydropyrrolo[1,2-α]pyrimidine-3,6-dicarboxylic acid 6-t-butyl ester 3-methyl ester (0.22 g, 0.74 mmol) in MeOH cooled to 0° C. was added 2N NaOH (0.37 mL, 0.74 mmol) dropwise. The reaction mixture was allowed to warm slowly to rt and stirred overnight. The reaction mixture was washed twice with Et$_2$O, and the aqueous layer was acidified to pH 2 with 1N HCl, which was then extracted twice with EtOAc. The combined organic layers were dried over MgSO$_4$ and concentrated to provide (S)-4-oxo-4,6,7,8-tetrahydropyrrolo[1, 2-α]pyrimidine-3,6-dicarboxylic acid 6-t-butyl ester (0.14 g, 70%) as a solid yellow foam $^1$H NMR (CDCl$_3$) δ 1.50 (s, 9H), 2.41 (m, 1H), 2.68 (m, 1H), 3.21–3.41 (m, 2H), 5.10 (m, 1H), 8.94 (s, 1H). MS calcd C$_{13}$H$_{16}$N$_2$O$_5$+H, 281, found 281.

Preparation of Intermediate (S)-3-(CBZ-Amino)-4-Oxo-4,6, 7,8-Tetrahydropyrrolo-[1,2-α]Pyrimidine-6-Carboxylic Acid t-Butyl Ester.

(S)4-Oxo-4,6,7,8-tetrahydropyrrolo[1,2-α]pyrimidine-3, 6-dicarboxylic acid 6-t-butyl ester (0.58 g, 2.07 mmol), triethylamine (0.29 mL, 2.07 mmol) and diphenylphosphoryl azide (0.45 mL, 2.07 mmol) in 1,4-dioxane (10 mL) were heated to reflux for 2 h. Benzyl alcohol (0.24 mL, 2.28 mmol) was added and heating at reflux was continued for another 3 h. The reaction mixture was then concentrated under vacuum, and the residue was purified by column chromatography on silica gel (2% MeOH/CHCl$_3$) to provide (S)-3-(CBZ-amino)-4-oxo-4,6,7,8-tetrahydropyrrolo[1,2-α] pyrimidine-6-carboxylic acid t-butyl ester (0.62 g, 77%) as a yellow solid. $^1$H NMR (CDCl$_3$) δ 1.48 (s, 9H), 2.30 (m, 1H), 2.56 (m, 1H), 3.05–3.21 (m, 2H), 4.98 (m, 1H), 5.20 (s, 2H), 7.30–7.40 (m, 6H), 8.67 (bs, 1H). MS calcd for C$_{20}$H$_{23}$N$_3$O$_5$+H, 386, found 386.

Preparation of Intermediate (S)-3-(CBZ-Amino)-4-Oxo-4,6, 7,8-Tetrahydropyrrolo-[1,2α]Pyrimidine-6Carboxylic Acid.

To (S)-3-(CBZ-amino)-4-oxo-4,6,7,8-tetrahydropyrrolo [1,2α]pyrimidine-6-carboxylic acid t-butyl ester (0.20 g, 0.52 mmol) was added 8.0 mL of a 1:1 solution of TFA:CHCl$_3$ with 3 drops of H$_2$O. The reaction mixture was stirred at rt overnight, at which time it was concentrated under vacuum. CCl$_4$ was added, and the mixture was reconcentrated, and then triturated in Et$_2$O. Filtration provided (S)-3-(CBZ-amino)4-oxo-4,6,7,8-tetrahydropyrrolo [1,2-α]pyrimidine-6-carboxylic acid (0.14 g, 82%) as a tan solid $^1$H NMR (CDCl$_3$) δ 2.50–2.63 (m, 2H), 3.16–3.29 (m, 2H), 5.13 (m, 1H), 5.20 (s, 2H), 5.45 (bs, 1H), 7.37 (s, 5H), 7.40 (s, 1H), 8.70 (bs, 1H). MS calcd for C$_{16}$H$_{15}$N$_3$O$_5$+H 330, found 330.

Preparation of Intermediate Ethyl-3-[(S)-3-(CBZ-Amino)-4-Oxo-4,6,7,8Tetrahydropyrrolo[1,2-α]Pyrimidine-6-L-(Tr-Gln)]-E-Propenoate.

Ethyl-3-[BOC-L-(Tr-Gln)]-E-propenoate (0.28 g, 0.52 mmol) was deprotected and coupled to (S)-3-(CBZ-amino)-4-oxo-4,6,7,8-tetrahydropyrrolo[1,2-α]pyrimidine-6-carboxylic acid (0.14 g, 0.41 mmol) using the procedure described in Example 1 for the preparation of ethyl-3-[BOC-L-N-Me-Phe-L-(Tr-Gln)]-E-propenoate, to provide ethyl-3-[(S)-3-(CBZ-amino)-4-oxo-4,6,7,8-tetrahydropyrrolo[1,2-α]pyrimidine-6-L-(Tr-Gln)]-E-propenoate (0.26 g, 83%) as a solid white foam after column chromatography (2% methanol/CHCl$_3$) $^1$H NMR (CDCl$_3$) δ 1.28 (t, 3H, J=7.2 Hz), 1.83 (m, 1H), 2.01 (m, 1H), 2.29–2.36 (m, 2H), 2.49–2.51 (m, 2H), 2.97 (m, 1H), 3.19 (m, 1H), 4.18 (q, 2H, J=7.2 Hz), 4.53–4.57 (s, 2H), 5.86 (dd, 1H, J=15.6, 1.6 Hz), 6.79 (dd, 1H, J=15.6, 5.3 Hz), 6.89 (s, 1H), 7.16–7.37 (m, 21H), 7.53 (d, 1H, J=7.2 Hz), 8.65 (bs, 1H).MS calcd for C$_{44}$H$_{43}$N$_5$O$_7$+Cs, 886, found 886.

Preparation of Product-Ethyl-3-[(S)-3-(CBZ-Amino)-4-Oxo-4,6,7,8Tetrahydropyrrolo[1,2-α]Pyrimidine-6-L-Gln]-E-Propenoate.

Ethyl-3-[(S)-3-(CBZ-amino)-4-oxo-4,6,7,8-tetrahydropyrrolo-[1,2α]pyrimidine-6-L-(Tr-Gln)]-E-propenoate (0.25 g, 0.33 mmol) was deprotected using the procedure described in Example 22 for the preparation of ethyl-3-(ethylthiocarbonyl-L-Leu-L-Pro-L-Gln)-E-propenoate, to provide ethyl-3-[(S)-3-(CBZ-amino)-4-oxo-4,6,7,8-tetrahydropyrrolo [1,2-α]pyrimidine-6-L-Gln]-E-propenoate (0.10 g, 59%) as a white solid after column chromatography on silica (5% methanol/CHCl$_3$): mp=204° C. (dec.); IR (thin film) 3282 1720 cm$^{-1}$; $^1$H NMR (CDCl$_3$) δ 1.29 (t, 3H, J=7.1 Hz), 1.86 (m, 1H), 2.05 (m, 1H), 2.28–2.35 (m, 2H), 2.46–2.51 (m, 2H), 3.02 (m, 1H), 4.20 (q, 2H, J=7.2 Hz), 4.62 (m, 1H), 5.00 (dd, 1H, J=8.3, 3.6 Hz), 5.20 (s, 1H), 5.57 (m, 1H), 5.86 (m, 1H), 5.94 (dd, 1H, J=15.5, 1.4 Hz), 6.84 (dd, 1H, J=15.6, 5.2 Hz), 7.36–7.40 (m, 5H), 7.44 (s, 2H), 8.69 (m, 1H). HRMS calcd for C$_{25}$H$_{29}$N$_5$O$_7$+Cs 644.112, found 644.1143; Anal (C$_{25}$H$_{29}$N$_5$O$_7$) C, H, N.

The remaining compounds illustrated above can be produced by the skilled artisan, using routine experimentation, in a manner analogous to the various procedures described above in Examples 1 through 35.

BIOCHEMICAL AND BIOLOGICAL EVALUATION

Inhibition of Rhinovirus Protease

Stock solutions (50 mM, in DMSO) of various compounds were prepared; dilutions were in the same solvent. Recombinant Rhinovirus 3C proteases from serotypes 14, 16, 2 or 89 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Assays contained 2% DMSO, 50 mM tris pH 7.6, 1 mM EDTA, a compound at the indicated concentrations, approximately 1 μM substrate, and 50–100 nM protease. For K$_i$ determinations, the compound and the enzyme were preincubated for 10 minutes at 30° C. prior to addition of the substrate (substrate start). The k$_{obs/I}$ values were obtained from reactions initiated by addition of enzyme rather than substrate. RVP activity is measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenched by the proximal DABCYL moiety. When the peptide was cleaved, the quenching was relieved, and activity was measured as an increase in fluorescence signal. Data was analyzed using standard non linear fitting programs (Enzfit), and are shown Table 1.

TABLE 1

| COMPOUND | RVP | INHIB | k$_{obs/I}$ (M$^{-1}$sec$^{-1}$) |
|---|---|---|---|
| 1 | | >100 μM(K$_i$) | 52 |
| 2 | | ND | 5,300 |
| | (2) | ND | 617 |
| | (16) | ND | 1,035 |
| 3 | | 12 μM(K$_i$) | 16,565 |
| | (2) | ND | 292 |
| | (16) | ND | 929 |
| 4 | | 2.9 μM(K$_i$) | 43,800 |
| | (2) | ND | 541 |
| | (16) | ND | 2,009 |
| 5 | | ND | 17,320 |
| 6 | | ND | 9,500 |

TABLE 1-continued

| COMPOUND | RVP | INHIB | $k_{obs/I}$ (M$^{-1}$sec$^{-1}$) |
|---|---|---|---|
| 7 | | ND | 3,824 |
| 8 | | ND | 6,885 |
| 9 | | 4.4 μM(K$_i$) | 57,000 |
| 10 | | 2.0 μM(K$_i$) | 41,800 |
| 11 | | ND | 12,000 |
| 12 | | ND | 5,070 |
| 13 | | ND | 355,800 |
| | (2) | ND | 3,980 |
| | (16) | ND | 11,680 |
| 14 | | 0.8 μM(K$_i$) | 56,400 |
| | (2) | ND | 800 |
| | (16) | ND | 1800 |
| 15 | | 2.5 μM(K$_i$) | 36,400 |
| | (2) | ND | 3,500 |
| | (16) | ND | 5,600 |
| 16 | | 12 μM(K$_i$) | 8,300 |
| | (2) | ND | 600 |
| | (16) | ND | 1,000 |
| 17 | | ND | 750,000 |
| 18 | | 7.0 μM(K$_i$) | 423 |
| 19 | | ND | 1,927 |
| 20 | | 62 μM(K$_i$) | 3,332 |
| 21 | | 50 μM(K$_i$) | 256 |
| 22 | | ND | 100 |
| 23 | | 60 μM(K$_i$) | 605 |
| 24 | | 8 μM(K$_i$) | 21,960 |
| | (2) | ND | 7,100 |
| | (16) | ND | 9,300 |
| 25 | | ND | 1,469 |
| | (2) | ND | 1,277 |
| | (16) | ND | 770 |
| 26 | | 34 μM(K$_i$) | 875 |
| 27 | | ND | 102 |
| | (2) | ND | 87 |
| | (16) | ND | 90 |
| 28 | | 50 μM(K$_i$) | 116 |
| 29 | | ND | 45 |
| 30 | | 55 μM(K$_i$) | 163 |
| 31 | | ND | 39 |
| 32 | | ND | 98 |
| 33 | | 86(10) | 361 |
| 34 | | ND | 13,400 |
| | (2) | ND | 940 |
| | (16) | ND | 2,065 |
| 35 | | ND | 22,500 |
| | (2) | ND | 1,600 |
| | (16) | ND | 3,480 |
| 36 | | ND | 2,000 |
| | (2) | ND | 400 |
| | (16) | ND | 750 |
| 37 | | ND | 12,400 |
| | (2) | ND | 2,500 |
| | (16) | ND | 4,000 |
| 38 | | ND | 18,200 |
| 39 | | ND | 2,330 |
| 40 | | ND | 12,100 |
| 41 | | ND | 2,350 |
| 42 | | ND | 15,000 |
| 43 | | ND | 2,200 |
| 44 | | ND | 12,300 |
| 45 | | ND | 2,300 |
| 46 | | ND | 36,800 |
| 47 | | ND | 6,500 |
| 48 | | ND | 14,050 |
| 49 | | ND | 1,910 |
| 50 | | ND | 14,000 |
| 51 | | ND | 43,900 |
| 52 | | ND | 31,100 |
| 53 | | ND | 242 |
| 54 | | 55(10) | ND |
| 55 | | 20(10) | ND |
| 56 | | ND | 15,400 |
| 57 | | ND | 13,500 |
| 58 | | ND | 24,300 |
| 59 | | 2.8 | 108,000 |

In the above table, all data is for RVP serotype-14 unless otherwise noted in parentheses. All strains of human rhinovirus (HRV) were purchased from American Type Culture Collection (ATCC), except for serotype 14, which was produced from the infectious cDNA clone constructed and supplied to us by Dr. Roland Rueckert at the Institute for Molecular Virology, University of Wisconsin, Madison, Wis. The column designated INHIB represents the percent inhibition, with the concentration of the compound in μM indicated in parentheses, unless K$_i$ was assigned as designated by (K$_i$), at 10 minute preincubation with 50 nM RVP prior to addition of substrate was used. The data in the column designated k$_{obs/I}$ was measured from progress curves in enzyme start experiments. The designation NI indicates that no inhibition was obtained when 10 μM of a compound was used. The designation ND indicates that a value was not determined for that compound.

Antirhinoviral HI-HeLa Cell Culture Assay

In the Cell Protection Assay, the ability of compounds to protect cells against HRV infection was measured by the XTT dye reduction method. This method is described in O. S. Weislow, R. Kiser, D. L. Fine, J. Bader, R. H. Shoemaker, and M. R. Boyd, *J. Natl. Cancer Inst.* 1989, 81, 577–586, which document is entirely incorporated herein by reference.

HI-HeLa cells were infected with HRV-14 (unless otherwise noted) at a multiplicity of infection (m.o.i.) of 0.13 (virus particles/cell) or mock-infected with medium only. Infected or mock-infected cells were resuspended at 8×10$^5$ cells per mL and incubated with appropriate concentrations of compounds of formulas I and II. Two days later, XTT/PMS was added to test plates, and the amount of formazan produced was quantified spectrophotometrically at 450/650 nm. The EC$_{50}$ was calculated as the concentration of compound that increased the percentage of formazan production in compound-treated, virus-infected cells to 50% of that produced by compound-free mock-infected cells. The 50% cytotoxic dose (CC$_{50}$) was calculated as the concentration of compound that decreased the percentage of formazan produced in compound-treated, mock-infected cells to 50% of that produced in compound-free, mock-infected cells. The therapeutic index (TI) was calculated by dividing the CC$_{50}$ by the EC$_{50}$.

All strains of human rhinovims (HRV) for use in this assay were purchased from American Type Culture Collection (ATCC), except for HRV serotype-14, which was produced from the infectious cDNA clone, constructed and supplied to us by Dr. Roland Rueckert at the Institute for Molecular Virology, University of Wisconsin, Madison, Wis. HRV stocks were propagated, and antiviral assays were performed in HI-HeLa (ATCC). Cells were grown in Minimal Essential Medium, available from Life Technologies, with 10% fetal bovine serum.

The compounds were tested against control compounds WIN 51711, WIN 52084, and WIN 54954, all obtained from Sterling-Winthrop Pharmaceuticals, and control compound Pirodavir, obtained from Janssen Pharmaceuticals. Antiviral data obtained for the test compounds are shown in Table 2 where all data are for HRV serotype-14 unless otherwise noted in parentheses.

TABLE 2

| Compound # | EC$_{50}$($\mu$M) | CC$_{50}$($\mu$M) | TI |
|---|---|---|---|
| 1 | 20 | 251 | 13 |
| 2 | 1.0 | 56 | 56 |
| 3 | 0.18 | 41.7 | 232 |
| 4 | 0.23 | 200 | 870 |
| 5 | 0.24 | 51.4 | 214 |
| 6 | 2.8 | 151.4 | 54 |
| 7 | 1.3 | 47.9 | 37 |
| 8 | 10 | >320 | >32 |
| 9 | 0.25 | 56.2 | 225 |
| 10 | 1.8 | 56.2 | 31 |
| 11 | 0.53 | >320 | >603 |
| 12 | 4.2 | >320 | >76 |
| 13 | 0.12 | 17.8 | 148 |
| 14 | 0.32 | 15.8 | 49 |
| 15 | 0.26 | 50.1 | 192 |
| 16 | 1.7 | 32 | 19 |
| 17 | 0.5 | 53 | 106 |
| 18 | 5.0 | 126 | 25 |
| 19 | 50 | >320 | >6 |
| 20 | 5.4 | 56 | 10.3 |
| 21 | 22 | >320 | >15 |
| 22 | 177.8 | >320 | >2 |
| 23 | 10 | 224 | 22 |
| 24 | 10 | >100 | >10 |
| 25 | 14 | >320 | >23 |
| 26 | 56 | >320 | >5 |
| 27 | >320 | >320 | |
| 28 | 6.9 | 125 | 18 |
| 29 | 46 | 251 | 5 |
| 30 | 7.2 | 177 | 25 |
| 31 | 56 | >320 | >6 |
| 32 | 158 | >320 | >2 |
| 33 | >320 | >320 | |
| 34 | 0.32 | >100 | >312 |
| 35 | 0.19 | >100 | >526 |
| 36 | 11.2 | >100 | >9 |
| 37 | 8.9 | >100 | >11 |
| 38 | 0.36 | >100 | >278 |
| 39 | 1.6 | 180 | 113 |
| 40 | 0.32 | 45 | 141 |
| 41 | 2.0 | 18 | 9 |
| 42 | 0.45 | 50.1 | 111 |
| 43 | 3.5 | 56.2 | 16 |
| 44 | 0.54 | 56.2 | 104 |
| 45 | 1.78 | 56.2 | 32 |
| 46 | 0.54 | 18 | 33 |
| 47 | 1.3 | 18 | 14 |
| 48 | 0.5 | >10 | >20 |
| 49 | 0.1 | 71 | 710 |
| 50 | 3.2 | >100 | >31 |
| 51 | 12.6 | >100 | >8 |
| 52 | 32 | >100 | >3 |
| 53 | 4.5 | >100 | >22 |
| 54 | 17.8 | >100 | >6 |
| 55 | 50 | >100 | >2 |
| 56 | 1.6 | 20 | 13 |
| 57 | 0.56 | 50 | 89 |
| 58 | 0.56 | 63 | 113 |
| 59 | 0.14 | >100 | >714 |
| 59 (HRV 1A) | 0.40 | >100 | >250 |
| 59 (HRV 10) | 0.40 | >100 | >250 |
| WIN 51711 | 0.78 | >60 | >77 |
| WIN 52084 | 0.07 | >10 | >143 |
| WIN 54954 | 2.13 | >63 | >30 |
| Pirodavir | 0.03 | >10 | >300 |

Anticoxsackieviral Hi HeLa Cell Culture Assay

The ability of compounds to protect cells against CVA-21 or CVB-3 infection was measured by the XTT dye reduction method. Briefly, HI-HeLa cells were infected with CVA-21 or CVB-3 at a multiplicity of infection (m.o.i.) of 0.05 (CVA-21) and 0.08 (CVB-3) or mock-infected with medium only. Infected or uninfected cells were resuspended at 4×10$^4$ cells per mL and incubated with appropriate concentrations of drug. One day later, XTT/PMS was added to test plates, and the amount of formazan produced was quantified spectrophotometrically at 450/650 nm. The EC$_{50}$ was calculated as the concentration of drug that increased the percentage of formazan production in drug-treated, virus-infected cells to 50% of that produced by drug-free, uninfected cells. The 50% cytotoxic dose (CC$_{50}$) was calculated as the concentration of drug that decreased the percentage of formazan produced in drug-treated, uninfected cells to 50% of that produced in drug-free, uninfected cells. The therapeutic index (TI) was calculated by dividing the CC$_{50}$ by the EC$_{50}$.

The Coxsackie strains A-21 (CVA-21) and B-3 (CVB-3) were purchased from American Type Culture Collection (ATCC). Virus stocks were propagated and antiviral assays were performed in HI-HeLa cells (ATCC). Cells were grown in Minimal Essential Medium with 10% fetal bovine serum.

TABLE 3

Antiviral efficacy of compounds against CVB-3 infection of Hi-HeLa cells

| Compound # | EC$_{50}$($\mu$M) | CC$_{50}$($\mu$M) | TI |
|---|---|---|---|
| 2 | 2.0 | 56 | 28 |
| WIN 54954 | >100 | >100 | |
| Pirodavir | >100 | >100 | |

TABLE 4

Antiviral efficacy of compounds against CVA-21 infection of Hi-HeLa cells

| Compound # | EC$_{50}$($\mu$M) | CC$_{50}$($\mu$M) | TI |
|---|---|---|---|
| 2 | 3.3 | 56 | 17 |
| 4 | 1.8 | 200 | 111 |
| WIN 54954 | >100 | >100 | |
| Pirodavir | >100 | >100 | |

Echovirus-11 and Enterovirus-70 MRC5 Cell Culture Assay

The Echovirus strain 11 (ECHO-11) and Enterovirus strain 70 (ENT-70) were purchased from American Type Culture Collection (ATCC). Virus stocks were propagated and antiviral assays were performed in MRC5 cells (ATCC). Cells were grown in Minimal Essential Medium with 10% fetal bovine serum.

The ability of compounds to protect cells against ECHO-11 or ENT-70 infection was measured by the XTT dye reduction method. Briefly, MRC5 cells were infected with ECHO-11 or ENT-70 at a multiplicity of infection (m.o.i.) of 0.0013 (ECHO-11) and 0.0017 (ENT-70) or mock-infected with medium only. Infected or uninfected cells were resuspended at 2×10$^4$ cells per mL and incubated with appropriate concentrations of drug. One day later, XTT/PMS was added to test plates, and the amount of formazan produced was quantified spectrophotometrically at 450/650 nm. The EC$_{50}$ was calculated as the concentration of drug that increased the percentage of formazan production in drug-treated, virus-infected cells to 50% of that produced by drug-free, uninfected cells. The 50% cytotoxic dose (CC$_{50}$) was calculated as the concentration of drug that decreased the percentage of formazan produced in drug-treated, uninfected cells to 50% of that produced in drug-free, uninfected cells. The therapeutic index (TI) was calculated by dividing the CC$_{50}$ by the EC$_{50}$.

TABLE 5

Antiviral efficacy of compounds against ECHO-11 infection of MRC5 cells

| Compound # | $EC_{50}(\mu M)$ | $CC_{50}(\mu M)$ | TI |
|---|---|---|---|
| 2 | 3.1 | 56 | 18 |
| 4 | 3.2 | 200 | 62.5 |
| WIN 54954 | >100 | >100 | |
| Pirodavir | >100 | >100 | |

TABLE 6

Antiviral efficacy of compounds against ENT-70 infection of MRC5 cells

| Compound # | $EC_{50}(\mu M)$ | $CC_{50}(\mu M)$ | TI |
|---|---|---|---|
| 2 | 0.6 | 56 | 93 |
| 4 | 0.3 | 200 | 667 |
| WIN 54954 | >100 | >100 | |
| Pirodavir | >100 | >100 | |

In describing the invention, the inventors have set forth certain theories and mechanisms in an effort to disclose how or why the invention works in the manner in which it works. These theories and mechanisms are set forth for informational purposes only. Applicants are not to be bound by any specific chemical or physical mechanisms or theories of operation.

While the invention has been described in detail and with reference to specific embodiments thereof, it will be apparent to one skilled in the art that various changes and modifications can be made therein without departing from the spirit and scope thereof. Thus, it is intended that the present invention cover the modifications and variations, provided they come within the scope of the appended claims and their equivalents.

We claim:

1. A compound of formula (I):

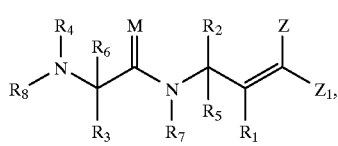

wherein:

M is O or S;

$R_1$ is H, F, an alkyl group, OH, SH, or an O-alkyl group;

$R_2$ and $R_5$ are independently selected from H,

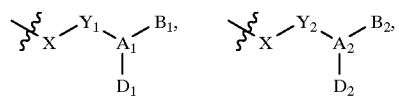

or an alkyl group, wherein said alkyl group is different from

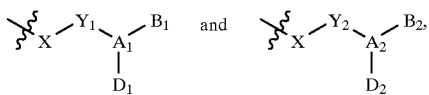

with the proviso that at least one of $R_2$ or $R_5$ must be

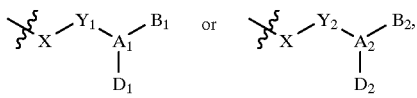

and wherein, when $R_2$ or $R_5$ is

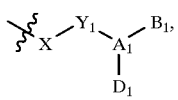

$X$ is =CH or =CF and $Y_1$ is =CH or =CF, or X and $Y_1$ together with Q' form a three-membered ring in which Q' is —C($R_{10}$)($R_{11}$)— or —O—, X is —CH— or —CF—, and Y is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —$CH_2$—, —$CF_2$—, —CHF—, or —S—, and $Y_1$ is —O—, —S—, —$NR_{12}$—, —C($R_{13}$)($R_{14}$)—, —C(O)—, —C(S)—, or —C($CR_{13}R_{14}$)—, wherein $R_{12}$ is H or alkyl, and $R_{13}$ and $R_{14}$ independently are H, F, or an alkyl group, or, together with the atoms to which they are bonded, form a cycloalkyl group or a heterocycloalkyl group;

$A_1$ is C, CH, CF, S, P, Se, N, $NR_{15}$, S(O), Se(O), P—$OR_{15}$, or P—$NR_{15}R_{16}$, wherein $R_{15}$ and $R_{16}$ independently are an alkyl group, a cycloalkyl group, a heterocycloalkyl group, an aryl group, or a heteroaryl group, or, together with the atom to which they are bonded, form a heterocycloalkyl group;

$D_1$ is a moiety with a lone pair of electrons capable of forming a hydrogen bond; and $B_1$ is H, F, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$, wherein $R_{17}$, $R_{18}$, and $R_{19}$ independently are H, an alkyl group, a cycloalkyl group, a heterocycloalkyl group, an aryl group, a heteroaryl group, or an acyl group;

and with the provisos that when $D_1$ is the moiety ≡N with a lone pair of electrons capable of forming a hydrogen bond, $B_1$ does not exist; and when $A_1$ is an $sp^3$ carbon, $B_1$ is not —$NR_{17}R_{18}$ when $D_1$ is the moiety —$NR_{25}R_{26}$ with a lone pair of electrons capable of forming a hydrogen bond, wherein $R_{25}$ and $R_{26}$ are independently H, an alkyl group, a cycloalkyl group, a heterocycloalkyl group, an aryl group, or a heteroaryl group; and wherein $D_1$—$A_1$—$B_1$ optionally forms a nitro group where $A_1$ is N; and further wherein, when $R_2$ or $R_5$ is

X is =CH or =CF and $Y_2$ is =C, =CH or =CF,
or X and $Y_2$ together with Q' form a three-membered ring in which Q' is —C($R_{10}$)($R_{11}$)— or —O—, X is —CH— or —CF—, and $Y_2$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group,
or X is —$CH_2$—, —$CF_2$—, —CHF—, or —S—, and $Y_2$ is —O—, —S—, —N($R'_{12}$)—, —C($R'_{13}$)($R'_{14}$)—, —C(O)—, —C(S)—, or —C($CR'_{13}R'_{14}$)—,
  wherein $R'_{12}$ is H, an alkyl group, a cycloalkyl group, a heterocycloalkyl group, an aryl group, a heteroaryl group, —$OR'_{13}$, —$NR'_{13}R'_{14}$, —C(O)—$R'_{13}$, —$SO_2R'_{13}$, or —C(S)$R'_{13}$, and $R'_{13}$ and $R'_{14}$, independently are H, F, or an alkyl group, a cycloalkyl group, a heterocycloalkyl group, an aryl group, or a heteroaryl group or, together with the atom to which they are attached, form a cycloalkyl group or a heterocycloalkyl group;
$A_2$ is C, CH, CF, S, P, Se, N, $NR_{15}$, S(O), Se(O), P—$OR_{15}$, or P—$NR_{15}R_{16}$,
  wherein $R_{15}$ and $R_{16}$ independently are an alkyl group, a cycloalkyl group, a heterocycloalkyl group, an aryl group, or a heteroaryl group or, together with the atom to which they are bonded, form a heterocycloalkyl group;
$D_2$ is a moiety with a lone pair of electrons capable of forming a hydrogen bond; and $B_2$ is H, F, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$,
  wherein $R_{17}$, $R_{18}$, and $R_{19}$ independently are H, an alkyl group, a cycloalkyl group, a heterocycloalkyl group, an aryl group, a heteroaryl group, or an acyl group;
and further wherein any combination of $Y_2$, $A_2$, $B_2$, and $D_2$ forms a cycloalkyl group, a heterocycloalkyl group, an aryl group, or a heteroaryl group; $R_3$ and $R_6$ are independently H, F, an alkyl group, a cycloalkyl group, a heterocycloalkyl group, an ayl group, a heteroaryl group, —C(O)$R_{17}$, —$OR_{17}$, —$SR_{17}$, —$NR_{17}R_{18}$, —$NR_{19}NR_{17}R_{18}$, or —$NR_{17}OR_{18}$,
  wherein $R_{17}$, $R_{18}$, and $R_{19}$ independently are H, an alkyl group, a cycloalkyl group, a heterocycloalkyl group, an aryl group, a heteroaryl group, or an acyl group;
or, $R_3$ and $R_6$, together with the carbon atom to which they are attached, form a cycloalkyl group or a heterocycloalkyl group; $R_4$ is any suitable organic moiety, or $R_4$ and $R_3$ or $R_6$, together with the atoms to which they are attached, form a heterocycloalkyl group;
$R_7$ is H, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$,
  wherein $R_{17}$, $R_{18}$, and $R_{19}$ independently are H, an alkyl group, a cycloalkyl group, a heterocycloalkyl group, an aryl group, a heteroaryl group, or an acyl group; or $R_7$, together with $R_3$ or $R_6$ and the atoms to which they are attached, forms a heterocycloalkyl group;
$R_8$ is H, an alkyl group, a cycloalkyl group, a heterocycloalkyl group, an aryl group, a heteroaryl group, —$NR_{29}R_{30}$, —$OR_{29}$, or —C(O)$R_{29}$,
  wherein $R_{29}$ and $R_{30}$ each independently are H, an alkyl group, a cycloalkyl group, a heterocycloalkyl group, an aryl group, or a heteroaryl group;
or $R_8$, together with $R_4$ and the nitrogen atom to which they are attached, forms a heterocycloalkyl group or a heteroaryl group, or $R_8$ and $R_3$ or $R_6$, together with the atoms to which they are attached, forms a heterocycloalkyl group;
Z and $Z_1$ are independently H, F, an alkyl group, a cycloalkyl group, a heterocycloalkyl group, an aryl group, a heteroaryl group, —C(O)$R_{21}$, —$CO_2R_{21}$, —CN, —C(O)$NR_{21}R_{22}$, —C(O)$NR_{21}OR_{22}$, —C(S)$R_{21}$, —C(S)$NR_{21}R_{22}$, —$NO_2$, —$SOR_{21}$, —$SO_2R_{21}$, —$SO_2NR_{21}R_{22}$, —SO($NR_{21}$)($OR_{22}$), —$SONR_{21}$, —$SO_3R_{21}$, —PO($OR_{21}$)$_2$, —PO($R_{21}$)($R_{22}$), —PO($NR_{21}R_{22}$)($OR_{23}$), —PO($NR_{21}R_{22}$)($NR_{23}R_{24}$), —C(O)$NR_{21}NR_{22}R_{23}$, or —C(S)$NR_{21}NR_{22}R_{23}$,
  wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group;
or $Z_1$, as defined above, together with $R_1$, as defined above, and the atoms to which $Z_1$ and $R_1$ are bonded, form a cycloalkyl or heterocycloalkyl group,
or Z and $Z_1$, both as defined above, together with the atoms to which they are bonded, form a cycloalkyl or heterocycloalkyl group;
with the proviso that when $R_7$ is H, $R_8$ is a moiety other than H; or a pharmaceutically acceptable prodrug, salt, active metabolite, or solvate thereof; and wherein said compound, pharmaceutically acceptable prodrug, salt, active metabolite, or solvate thereof has antipicornaviral activity with an $EC_{50}$ less than or equal to 100 μM in the HI-HeLa cell culture assay.

2. A compound of claim 1, wherein $R_1$ is H or F, or a pharmaceutically acceptable prodrug, salt, active metabolite, or solvate thereof.

3. A compound of claim 1, wherein at least one of $R_4$ and $R_8$ is an acyl group or a sulfonyl group, or a pharmaceutically acceptable prodrug, salt, active metabolite, or solvate thereof.

4. A compound of claim 1, wherein at least one of $R_2$ or $R_5$ is

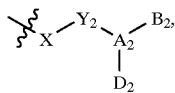

or a pharmaceutically acceptable prodrug, salt, active metabolite, or solvate thereof.

5. A compound according to claim 4, wherein $D_1$ is —$OR_{25}$, =O, =S, ≡N, =$NR_{25}$, or —$NR_{25}R_{26}$, wherein $R_{25}$ and $R_{26}$ are independently H, an alkyl group, a cycloalkyl group, a heterocycloalkyl group, an aryl group, or a heteroaryl group, or, together with the nitrogen atom to which they are bonded, form a heterocycloalkyl group; or a pharmaceutically acceptable prodrug, salt, active metabolite, or solvate thereof.

6. A compound according to claim 5, wherein $D_1$ is =O; or a pharmaceutically acceptable prodrug, salt, active metabolite, or solvate thereof.

7. A compound according to claim 4, wherein $A_1$ is C, CH, S, or S(O); or a pharmaceutically acceptable prodrug, salt, active metabolite, or solvate thereof.

8. A compound according to claim 7, wherein $A_1$ is C; or a pharmaceutically acceptable prodrug, salt, active metabolite, or solvate thereof.

9. A compound according to claim 4, wherein $B_1$ is $NR_{17}R_{18}$, wherein $R_{17}$ and $R_{18}$ are independently H, an alkyl group, a cycloalkyl group, a heterocycloalkyl group, an aryl group, a heteroaryl group, or an acyl group; or a pharmaceutically acceptable prodrug, salt, active metabolite, or solvate thereof.

10. A compound according to claim 1, wherein at least one of $R_2$ or $R_5$ is

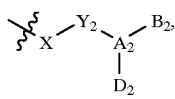

or a pharmaceutically acceptable prodrug, salt, active metabolite, or solvate thereof.

11. A compound according to claim 10, wherein $D_2$ is $-OR_{25}$, =O, =S, ≡N, =$NR_{25}$, or $-NR_{25}R_{26}$, wherein $R_{25}$ and $R_{26}$ are independently H, an alkyl group, a cycloalkyl group, a heterocycloalkyl group, an aryl group, or a heteroaryl group, or, together with the atom(s) to which they are bonded, form a heterocycloalkyl group; or a pharmaceutically acceptable prodrug, salt, active metabolite, or solvate thereof.

12. A compound according to claim 11, wherein $D_2$ is =O; or a pharmaceutically acceptable prodrug, salt, active metabolite, or solvate thereof.

13. A compound according to claim 10, wherein $A_2$ is C, CH, S, or S(O); or a pharmaceutically acceptable prodrug, salt, active metabolite, or solvate thereof.

14. A compound according to claim 13, wherein $A_2$ is C; or a pharmaceutically acceptable prodrug, salt, active metabolite, or solvate thereof.

15. A compound according to claim 10, wherein $B_2$ is $NR_{17}R_{18}$, wherein $R_{17}$ and $R_{18}$ are independently H, an alkyl group, a cycloalkyl group, a heterocycloalkyl group, an aryl group, a heteroaryl group, or an acyl group; or a pharmaceutically acceptable prodrug, salt, active metabolite, or solvate thereof.

16. A compound according to claim 1, wherein $A_1$ is C, CH, S, or S(O) or wherein $A_2$ is C, CH, S, or S(O); or a pharmaceutically acceptable prodrug, salt, active metabolite, or solvate thereof.

17. A compound according to claim 1, wherein Z and $Z_1$ are independently H, an aryl group, or a heteroaryl group, $-C(O)R_{21}$, $-CO_2R_{21}$, $-CN$, $-C(O)NR_{21}R_{22}$, $-C(O)NR_{21}OR_{22}$, $-C(S)R_{21}$, $-C(S)NR_{21}R_{22}$, $-NO_2$, $-SOR_{21}$, $-SO_2R_{21}$, $-SO_2NR_{21}R_{22}$ $-SO(NR_{21})(OR_{22})$, $SONR_{21}$, $-SO_3R_{21}$, $-C(O)NR_{21}NR_{22}R_{23}$, or $-C(S)NR_{21}NR_{22}R_{23}$;
wherein $R_{21}$, $R_{22}$, and $R_{23}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, and $R_{23}$, together with the atom(s) to which they are bonded, form a heterocycloalkyl group,
or Z and $Z_1$, together with the atoms to which they are bonded, form a heterocycloalkyl group, or a pharmaceutically acceptable prodrug, salt, active metabolite, or solvate thereof.

18. A compound according to claim 1, wherein M is O, or a pharmaceutically acceptable prodrug, salt, active metabolite, or solvate thereof.

19. A compound having the formula II:

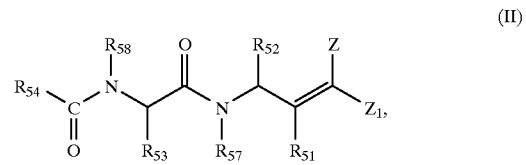

wherein:

$R_{51}$ is H, F, or an alkyl group;

$R_{52}$ is selected from one of the following moieties:

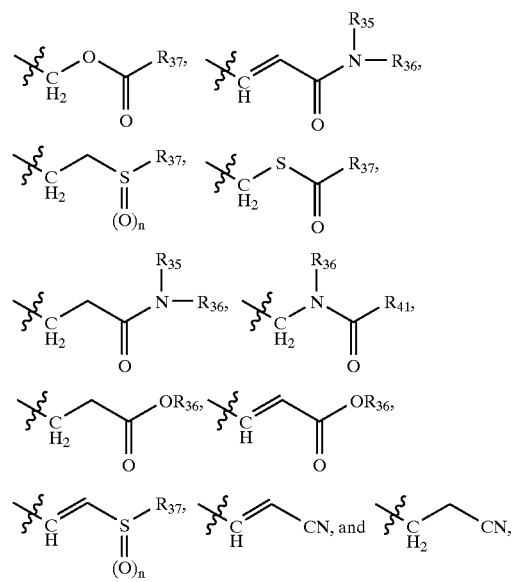

wherein:

$R_{35}$ is H, an alkyl group, an aryl group, $-OR_{38}$, or $-NR_{38}R_{39}$,
wherein $R_{38}$ and $R_{39}$ independently are H, an alkyl group, a cycloalkyl group, a heterocycloalkyl group, an aryl group, a heteroaryl group, or an acyl group; and $R_{36}$ is H or an alkyl group, or $R_{35}$ and $R_{36}$, together with the nitrogen atom to which they are attached, form a heterocycloalkyl group or a heteroaryl group;

$R_{37}$ is an alkyl group, an aryl group, or $-NR_{38}R_{39}$, wherein $R_{38}$ and $R_{39}$ are as defined above;

$R_{41}$ is H, an alkyl group, an aryl group, $-OR_{38}$, $-SR_{39}$, $-NR_{38}R_{39}$, $-NR_{40}NR_{38}R_{39}$, or $-NR_{38}OR_{39}$, or $R_{41}$ and $R_{36}$, together with the atoms to which they are attached, form a heterocycloalkyl group, and
wherein $R_{38}$ and $R_{39}$ are as defined above and $R_{40}$ is H, an alkyl group, a cycloalkyl group, a heterocycloalkyl group, an aryl group, a heteroaryl group, or an acyl group; and n is 0, 1 or 2;

$R_{53}$ is H or an alkyl group;

$R_{54}$ is an alkyl group, a cycloalkyl group, a heterocycloalkyl group, an aryl group, a heteroaryl group, an O-alkyl group, an O-cycloalkyl group, an O-heterocycloalkyl group, an O-aryl group, an O-heteroaryl group, an S-alkyl group, an NH-alkyl group, an NH-aryl group, an N,N-dialkyl group, or an N,N-diaryl group;

or $R_{54}$, together with $R_{58}$ and the nitrogen atom to which they are attached, forms a heterocycloalkyl group or a heteroaryl group;

$R_{57}$ is H or an alkyl group;

$R_{58}$ is H, an alkyl group, a cycloalkyl group, —$OR_{70}$, or —$NR_{70}R_{71}$, wherein $R_{70}$ and $R_{71}$ are independently H or an alkyl group; and Z and $Z_1$ are independently H, F, an alkyl group, a cycloalkyl group, a heterocycloalkyl group, an aryl group, a heteroaryl group, —C(O)$R_{21}$, —CO$_2R_{21}$, —CN, —C(O)NR$_{21}R_{22}$, —C(O)NR$_{21}$OR$_{22}$, —C(S)R$_{21}$, —C(S)NR$_{21}R_{22}$, —NO$_2$, —SOR$_{21}$, —SO$_2R_{21}$, —SO$_2$NR$_{21}R_{22}$, —SO(NR$_{21}$)(OR$_{22}$), —SONR$_{21}$, —SO$_3R_{21}$, —PO(OR$_{21}$)$_2$, —PO(R$_{21}$)(R$_{22}$), —PO(NR$_{21}R_{22}$)(OR$_{23}$), —PO(NR$_{21}R_{22}$)(NR$_{23}R_{24}$), —C(O)NR$_{21}$NR$_{22}R_{23}$, or —C(S)NR$_{21}$NR$_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group, or wherein Z and $Z_1$, together with the atoms to which they are bonded, form a heterocycloalkyl group;

with the proviso that when $R_{57}$ is H, $R_{58}$ is a moiety other than H;

or a pharmaceutically acceptable prodrug, salt, active metabolite, or solvate thereof.

20. A compound according to claim 1, having the formula Ia:

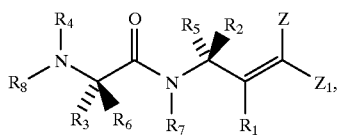

(Ia)

wherein $R_1$, $R_5$, $R_6$, and $R_7$ are H, $R_2$ is CH$_2$CH$_2$C(O)NH$_2$, $R_4$ is CH$_3$, and $R_3$, Z, $Z_1$, and $R_8$ are selected from one of the following groups:

$R_3$ is CH$_2$Ph, Z is H, $Z_1$ is CO$_2$CH$_2$CH$_3$, and $R_8$ is

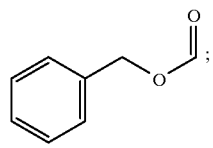

$R_3$ is CH$_2$Ph, Z is H, $Z_1$ is CO$_2$CH$_2$CH$_3$, and $R_8$ is

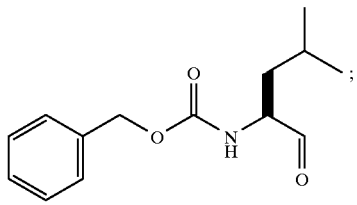

Z is H, $Z_1$ is CO$_2$CH$_2$CH$_3$, $R_3$ is

and $R_8$ is

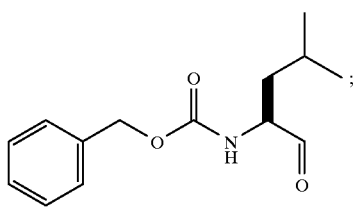

$R_3$ is

Z is H, $Z_1$ is CO$_2$CH$_2$CH$_3$, and $R_8$ is

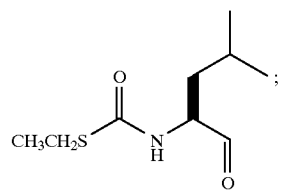

$R_3$ is CH$_2$Ph, Z is H, $Z_1$ is CO$_2$CH$_2$CH$_3$, and $R_8$ is

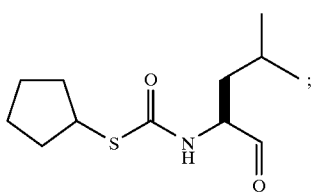

R₃ is CH₂Ph, Z and Z₁ together form

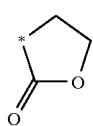

(wherein the C=O is cis to the R₁ group), and R₈ is

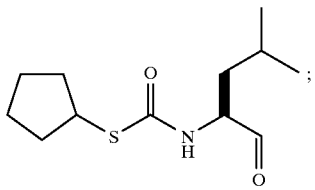

R₃ is CH₂Ph, Z is H, Z₁ is

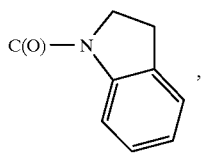

and R₈ is

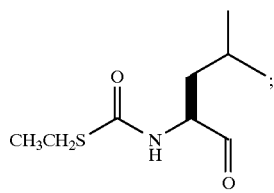

R₃ is CH₂Ph, Z and Z₁ together form

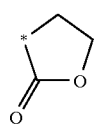

(wherein the C=O group is cis to the R₁ group), and R₈ is

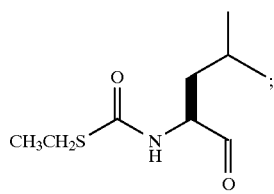

R₃ is CH₂Ph, Z is H, Z₁ is CO₂CH₂CH₃, and R₈ is

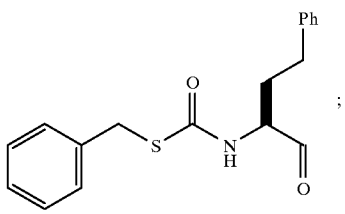

R₃ is CH₂Ph, Z and Z₁ together form

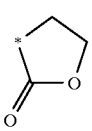

(wherein the C=O group is cis to the R₁ group), and R₈ is

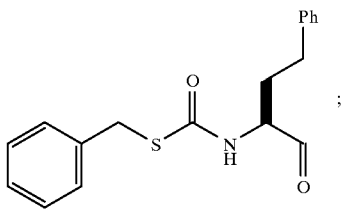

R₃ is CH₂Ph, Z is H, Z₁ is CO₂CH₂CH₃, and R₈ is

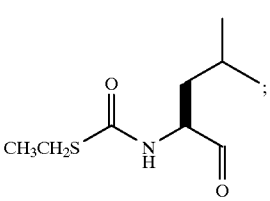

R₃ is CH₂Ph, Z and Z₁ together form

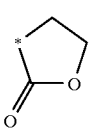

(wherein the C=O group is cis to the R₁ group), and R₈ is

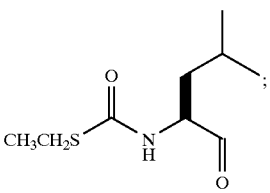

R₃ is

Z is H, Z₁ is CO₂CH₂CH₃, and R₈ is

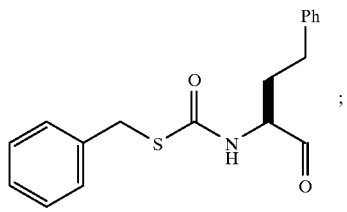

R₃ is

Z is CH₃, Z₁ is CO₂CH₂CH₃, and R₈ is

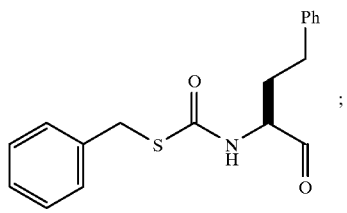

R₃ is CH₂Ph, Z is H, Z₁ is CO₂CH₂CH₃, and R₈ is

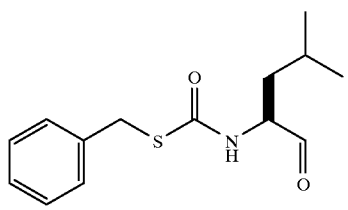

R₃ is CH₂Ph, Z is CH₃, Z₁ is CO₂CH₂CH₃, and R₈ is

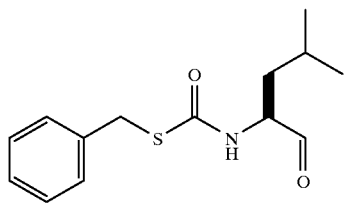

and

R₃ is CH₂Ph, Z is H, Z₁ is

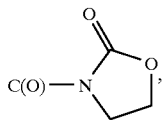

and R₈ is

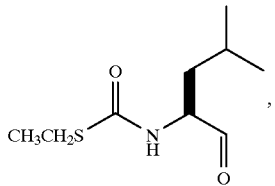

or a pharmaceutically acceptable prodrug, salt, active metabolite, or solvate thereof.

21. A compound according to claim 1, having the formula Ib:

(Ib)

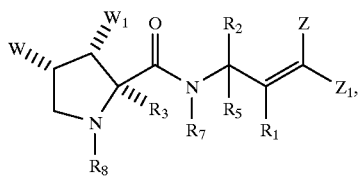

wherein R₁, R₃, R₅, R₇, and Z are H, R₂ is CH₂CH₂C(O)NH₂, and Z₁, W, W₁, and R₈ are selected from one of the following groups:

Z₁ is CO₂CH₂CH₃, W is H, W₁ is Ph, and R₈ is

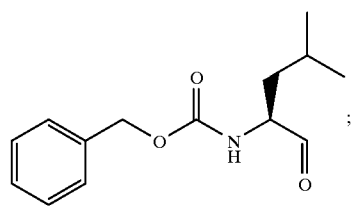

Z₁ is CO₂CH₂CH₃, W is H, W₁ is H, and R₈ is

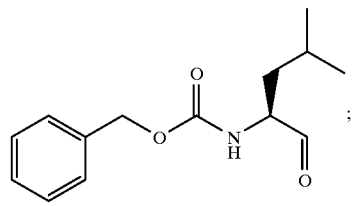

$Z_1$ is $CO_2CH_2CH_3$, W is $OCH_2Ph$, $W_1$ is H, and $R_8$ is

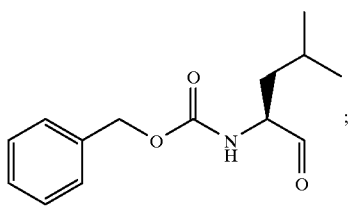

$Z_1$ is $CO_2CH_2CH_3$, W is H, $W_1$ is $CH_3$, and $R_8$ is

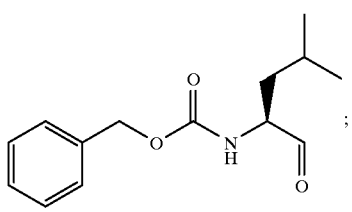

$Z_1$ is $CO_2CH_2CH_3$, W is $OC(CH_3)_3$, $W_1$ is H, and $R_8$ is

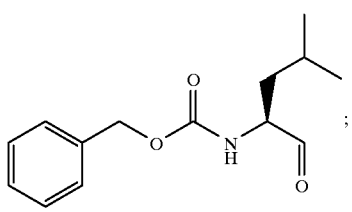

and $Z_1$ is $CO_2CH_2CH_3$, W is H, $W_1$ is H, and $R_8$ is

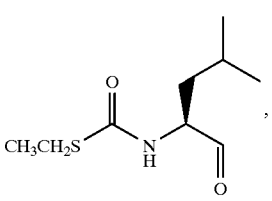

or a pharmaceutically acceptable prodrug, salt, active metabolite, or solvate thereof.

22. A compound according to claim 1, having the formula Ic:

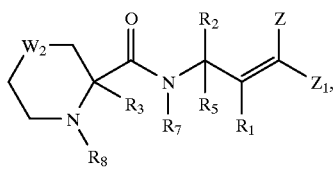

(Ic)

wherein $R_1$, $R_3$, $R_5$, $R_7$, and Z are H, $R_2$ is $CH_2CH_2C(O)NH_2$, $R_8$ is

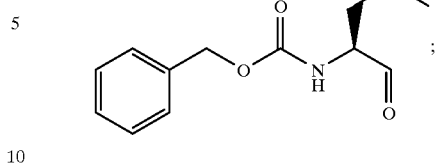

and $W_2$ and $Z_1$ are selected from one of the following groups:
  $W_2$ is $CH_2$ and $Z_1$ is $CO_2CH_2CH_3$;
  $W_2$ is $CH_2$ and $Z_1$ is

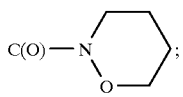

$W_2$ is $NCH_2Ph$ and $Z_1$ is $CO_2CH_2CH_3$; and
$W_2$ is $NSO_2Ph$ and $Z_1$ is $CO_2CH_2CH_3$, or a pharmaceutically acceptable prodrug, salt, active metabolite, or solvate thereof.

23. A compound according to claim 1, having the formula Id:

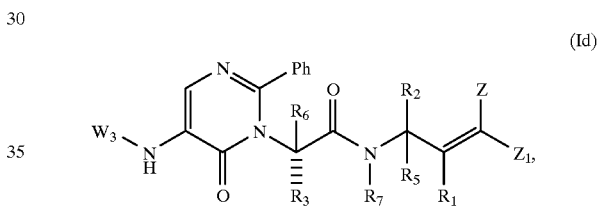

(Id)

wherein $R_1$, $R_3$, $R_5$, $R_6$, $R_7$, and Z are H, $R_2$ is $CH_2CH_2C(O)NH_2$, $Z_1$ is $CO_2CH_2CH_3$, and $W_3$ is H or

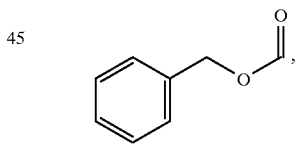

or a pharmaceutically acceptable prodrug, salt, active metabolite, or solvate thereof.

24. A compound according to claim 1, having the formula Ia:

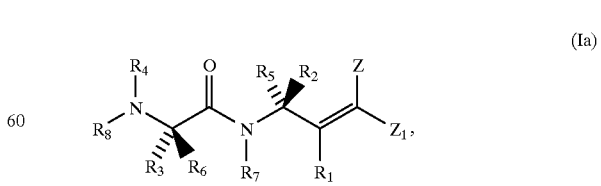

(Ia)

wherein $R_1$, $R_5$, $R_6$, and $R_7$ are each H, $R_2$ is $CH_2CH_2C(O)NH_2$, $R_4$ is $CH_3$, and $R_3$, Z, $Z_1$, and $R_8$ are selected from one of the following groups:

99

R$_3$ is CH$_2$Ph, Z is H, Z$_1$ is CO$_2$CH$_2$CH$_3$, and R$_8$ is

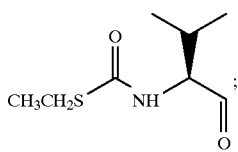

R$_3$ is CH$_2$Ph, Z is H, Z$_1$ is CO$_2$CH$_2$CH$_3$, and R$_8$ is

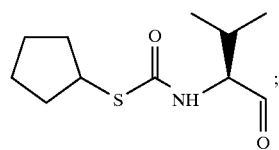

R$_3$ is CH$_2$Ph, Z is H, Z$_1$ is C(O)N(CH$_3$)OCH$_3$, and R$_8$ is

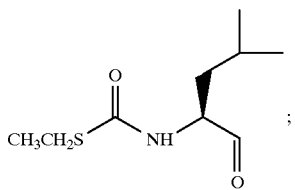

R$_3$ is CH$_2$Ph, Z is H, Z$_1$ is CO$_2$CH$_2$CH$_3$, and R$_8$ is

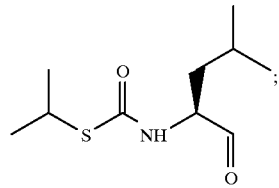

R$_3$ is CH$_2$Ph, Z is CH$_3$, Z$_1$ is CO$_2$CH$_2$CH$_3$, and R$_8$ is

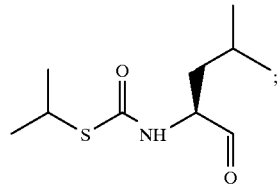

R$_3$ is CH$_2$Ph, Z is H, Z$_1$ is CO$_2$CH$_2$CH$_3$, and R$_8$ is

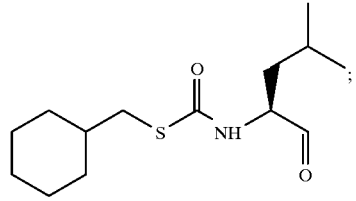

100

R$_3$ is CH$_2$Ph, Z is CH$_3$, Z$_1$ is CO$_2$CH$_2$CH$_3$, and R$_8$ is

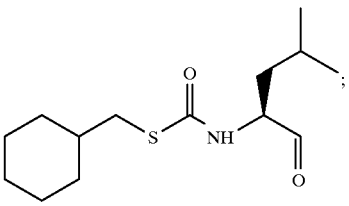

R$_3$ is CH$_2$Ph, Z is H, Z$_1$ is CO$_2$CH$_2$CH$_3$, and R$_8$ is

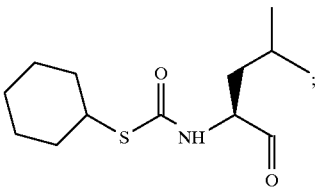

R$_3$ is CH$_2$Ph, Z is CH$_3$, Z$_1$ is CO$_2$CH$_2$CH$_3$, and R$_8$ is

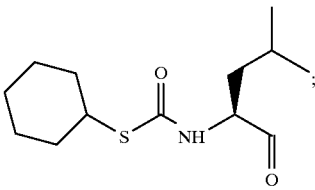

R$_3$ is CH$_2$Ph, Z is H, Z$_1$ is CO$_2$CH$_2$CH$_3$, and R$_8$ is

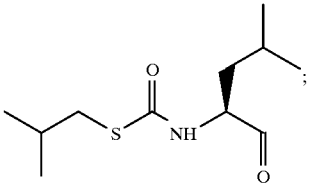

R$_3$ is CH$_2$Ph, Z is CH$_3$, Z$_1$ is CO$_2$CH$_2$CH$_3$, and R$_8$ is

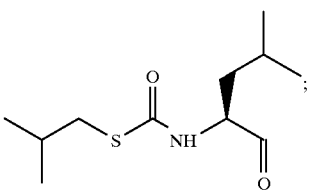

R$_3$ is CH$_2$Ph, Z is H, Z$_1$ is CO$_2$CH$_2$CH$_3$, and R$_8$ is

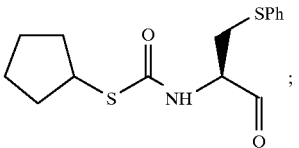

$R_3$ is $CH_2Ph$, Z is $CH_3$, $Z_1$ is $CO_2CH_2CH_3$, and $R_8$ is

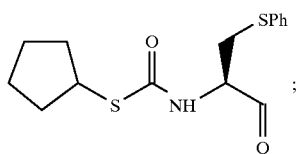

$R_3$ is

Z is H, $Z_1$ is $CO_2CH_2CH_3$, and $R_8$ is

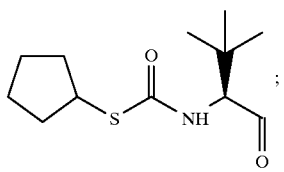

$R_3$ is

Z is $CH_3$, $Z_1$ is $CO_2CH_2CH_3$, and $R_8$ is

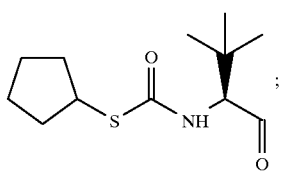

$R_3$ is $CH_2Ph$, Z is H, $Z_1$ is $CO_2CH_2Ph$, and $R_8$ is

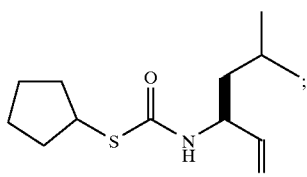

$R_3$ is $CH_2Ph$, Z is H, $Z_1$ is $CO_2CH_2CH_2CH_3$, and $R_8$ is

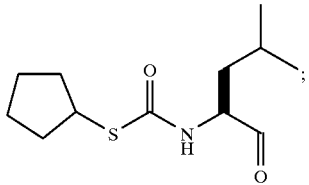

and
$R_3$ is $CH_2Ph$, Z is H, $Z_1$ is $CO_2CH_2CH_2OCH_3$, and $R_8$ is

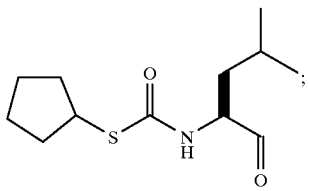

or a pharmaceutically acceptable prodrug, salt, active metabolite, or solvate thereof.

25. A compound according to claim 1, having the formula Ig:

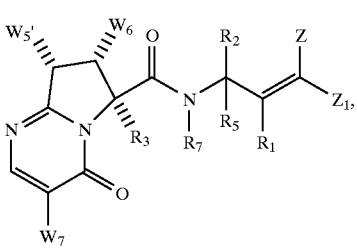

(Ig)

wherein $R_1$, $R_3$, $R_5$, $R_7$, $W_5$, $W_6$, and Z are H, $R_2$ is $CH_2CH_2C(O)NH_2$, $Z_1$ is $CO_2CH_2CH_3$, and $W_7$ is

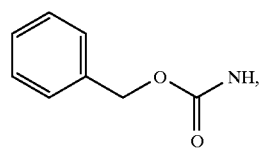

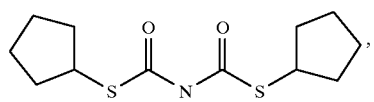

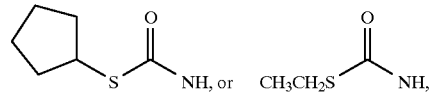

or a pharmaceutically acceptable prodrug, salt, active metabolite, or solvate thereof.

26. A compound according to claim 1, having the formula Ih:

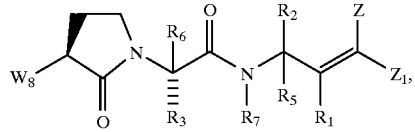
(Ih)

wherein $R_1$, $R_5$, $R_6$, and $R_7$ are H, $R_2$ is $CH_2CH_2C(O)NH_2$, $R_3$ is $CH_2Ph$, Z is H, $Z_1$ is $CO_2CH_2CH_3$, and $W_8$ is

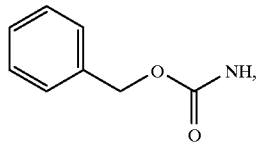

or a pharmaceutically acceptable prodrug, salt, active metabolite, or solvate thereof.

27. A compound according to claim 1, having the formula Ij:

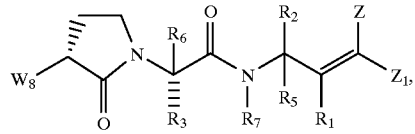
(Ij)

wherein $R_1$, $R_5$, $R_6$, and $R_7$ are H, $R_2$ is $CH_2CH_2C(O)NH_2$, $R_3$ is $CH_2Ph$, Z is H, $Z_1$ is $CO_2CH_2CH_3$, and $W_8$ is

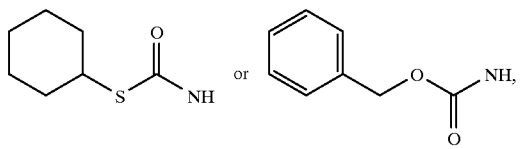

or a pharmaceutically acceptable prodrug, salt, active metabolite, or solvate thereof.

28. A compound according to claim 1, having the following formula X:

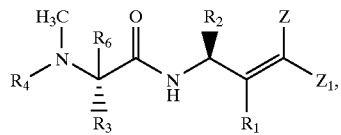
(X)

wherein $R_1$, $R_6$, and Z are H, $R_2$ is $CH_2CH_2C(O)NH_2$, $R_3$ is $CH_2Ph$, $Z_1$ is $CO_2CH_2CH_3$, and $R_4$ is selected from one of the following:

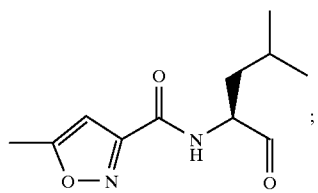

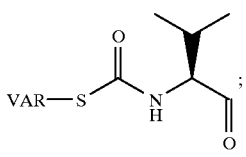

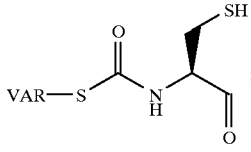

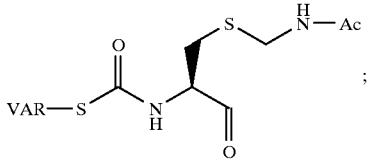

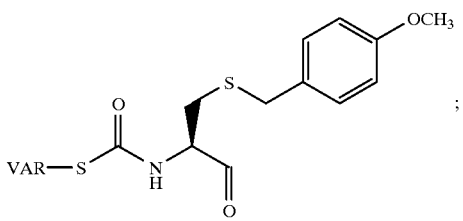

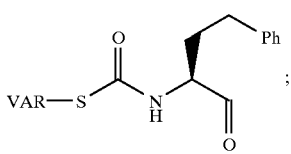

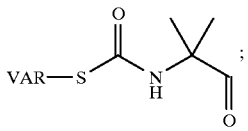

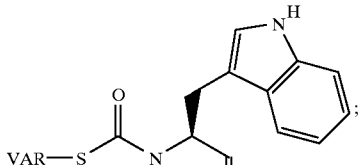

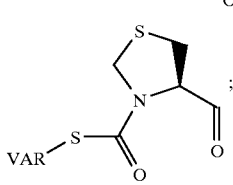

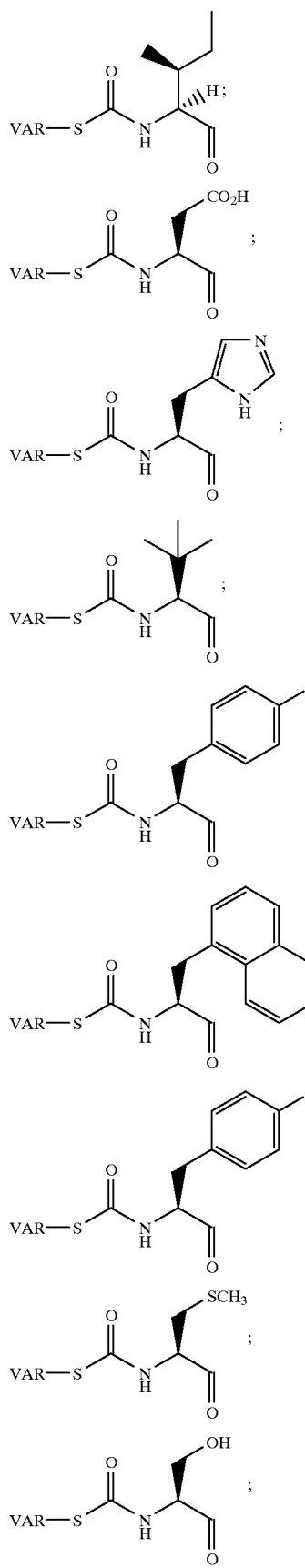
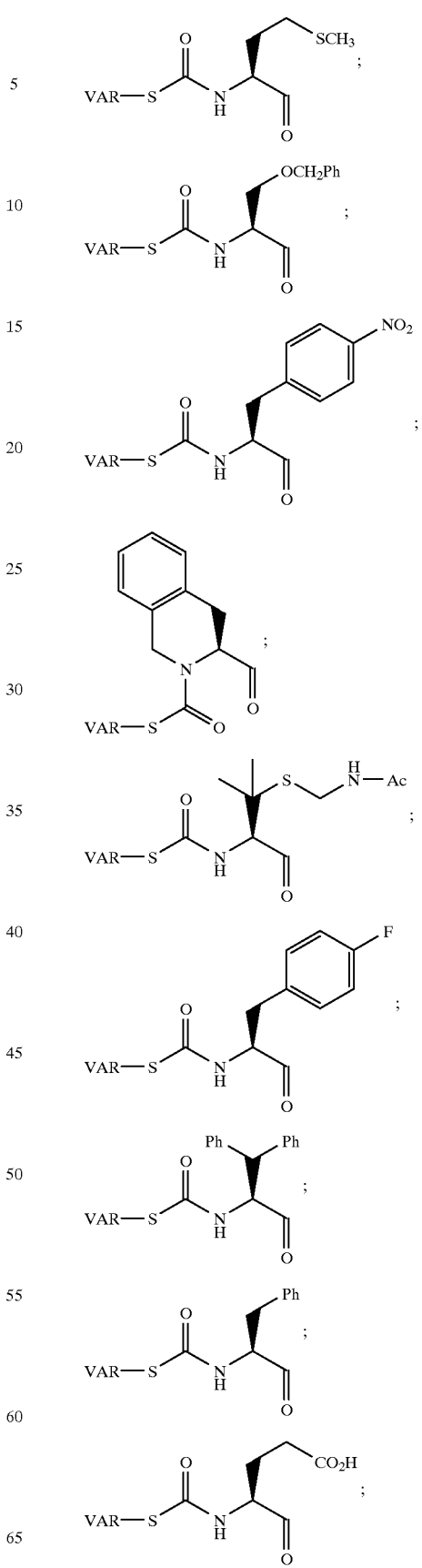

-continued

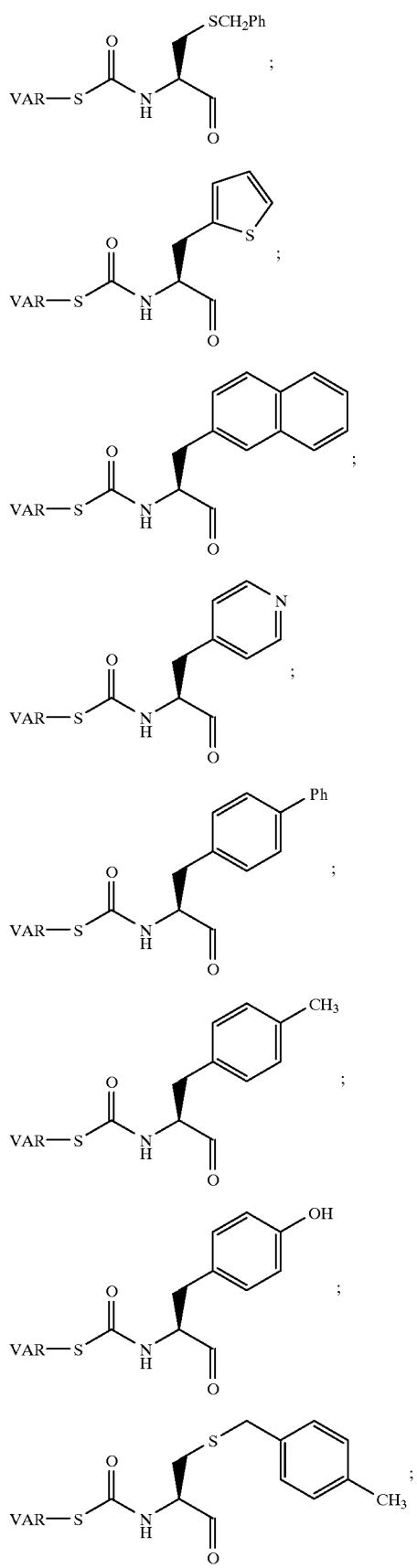

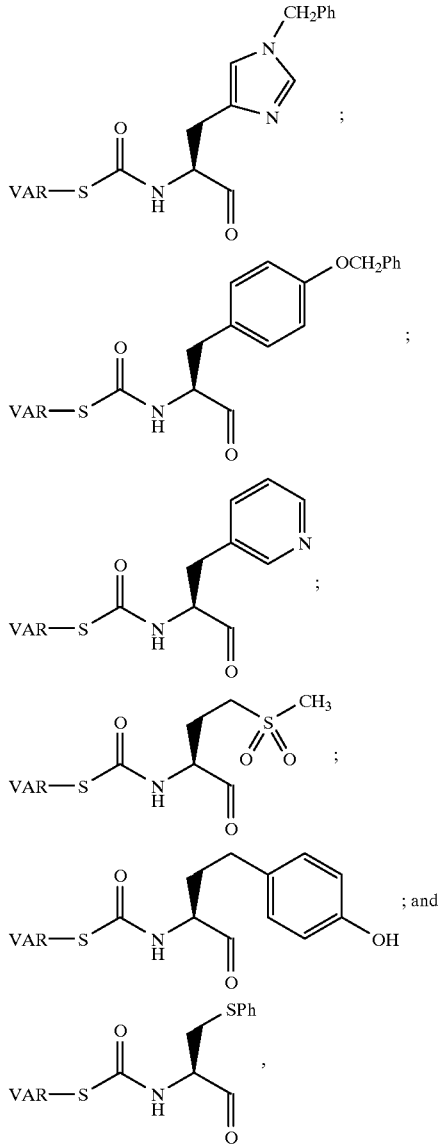

wherein VAR is selected from the group consisting of —$CH_2CH_3$, —$CH(CH_3)_2$, —$CH_2CH(CH_3)_2$, —$CH_2Ph$, or a pharmaceutically acceptable prodrug, salt, active metabolite, or solvate thereof.

29. A pharmaceutical composition comprising:
   (a) a therapeutically effective amount of a compound as defined in claim 1 or a pharmaceutically acceptable prodrug, salt, active metabolite, or solvate thereof; and
   (b) a pharmaceutically acceptable carrier, diluent, vehicle, or excipient.

30. A method of treating a mammalian disease condition mediated by picornaviral protease activity, comprising: administering to a mammal for the purpose of said treating a therapeutically effective amount of a compound as defined in claim 1 or a pharmaceutically acceptable prodrug, salt, active metabolite, or solvate thereof.

31. A method of inhibiting the activity of a picornaviral 3C protease, comprising:

contacting the picornaviral 3C protease for the purpose of said inhibiting with an effective amount of a compound as defined in claim 1 or a pharmaceutically acceptable prodrug, salt, active metabolite, or solvate thereof.

32. A method of inhibiting the activity of a rhinoviral protease, comprising:

contacting the rhinoviral protease for the purpose of said inhibiting with an effective amount of a compound as defined in claim 1 or a pharmaceutically acceptable prodrug, salt, active metabolite, or solvate thereof.

33. A compound according to claim 1, or a pharmaceutically acceptable prodrug, salt, active metabolite, or solvate thereof, wherein said antipicornaviral activity is antirhinoviral activity.

34. A compound according to claim 1, or a pharmaceutically acceptable prodrug, salt, active metabolite, or solvate thereof, wherein said antipicornaviral activity is anticoxsackieviral activity.

* * * * *

UNITED STATES PATENT AND TRADEMARK OFFICE
CERTIFICATE OF CORRECTION

Page 1 of 2

PATENT NO. : 5,962,487

DATED : October 5, 1999

INVENTORS : STEPHEN E. WEBBER, ET AL.

It is certified that error appears in the above-identified patent and that said Letters Patent is hereby corrected as shown below:

COVER PAGE:
  [56], "References Cited", "OTHER PUBLICATIONS",
    under Hammerle et al., "Traid" should read:  --Triad--;
    under Kaldor et al., "*Bioorganic&*" should read:
    --*Bioorganic &*--.

PAGE 3:
  [56], "OTHER PUBLICATIONS",
    under "Wellink, et al., "1-26.-" should read --1-26.--.

COLUMN 1:

Line 19, "Ru Zhou" should read --Ru Zhou.--; and
    "Attorney Docket No." should be deleted;
  Line 20, "1074.0176-01)." should be deleted.

COLUMN 34:
  Line 16, "An" should read:  --¶An--.

COLUMN 38:
  Line 67, "($C_{46}H_{47}N_3$.0.5 $H_2O$)" should read:
    --($C_{46}H_{47}N_3O_6 \cdot 0.5\ H_2O$)--.

COLUMN 40:
  Line 44, "Na2SO4" should read:  --$Na_2SO_4$--;
  Line 57, "C53H60N4O8.0.5 $H_2O$" should read:
    --$C_{53}H_{60}N_4O_8 \cdot 0.5\ H_2O$--.

UNITED STATES PATENT AND TRADEMARK OFFICE
CERTIFICATE OF CORRECTION

Page 2 of 2

PATENT NO. : 5,962,487

DATED : October 5, 1999

INVENTORS : STEPHEN E. WEBBER, ET AL.

It is certified that error appears in the above-identified patent and that said Letters Patent is hereby corrected as shown below:

<u>COLUMN 87</u>:
Line 47, "ayl" should read: --aryl--.

Signed and Sealed this

Twenty-fourth Day of October, 2000

Attest:

Q. TODD DICKINSON

*Attesting Officer*     *Director of Patents and Trademarks*